(12) United States Patent
Heaton et al.

(10) Patent No.: US 8,367,659 B2
(45) Date of Patent: Feb. 5, 2013

(54) OXAZINYL ISOFLAVONOID COMPOUNDS, MEDICAMENTS AND USE

(75) Inventors: Andrew Heaton, Forest Lodge (AU); Naresh Kumar, Maroubra (AU); Catherine Walker, Balmain (AU)

(73) Assignee: Marshall Edwards, Inc., San Diego, CA (US)

( * ) Notice: Subject to any disclaimer, the term of this patent is extended or adjusted under 35 U.S.C. 154(b) by 382 days.

(21) Appl. No.: 12/528,208

(22) PCT Filed: Feb. 29, 2008

(86) PCT No.: PCT/AU2008/000267
§ 371 (c)(1),
(2), (4) Date: Nov. 9, 2010

(87) PCT Pub. No.: WO2008/106715
PCT Pub. Date: Sep. 12, 2008

(65) Prior Publication Data
US 2011/0046722 A1    Feb. 24, 2011

(30) Foreign Application Priority Data

Mar. 2, 2007 (AU) ............................. 2007901105
Aug. 17, 2007 (AU) ............................. 2007904434

(51) Int. Cl.
*A61F 2/82* (2006.01)
*A61K 31/5365* (2006.01)
*A61P 9/00* (2006.01)
*A61P 31/00* (2006.01)
*A61P 39/06* (2006.01)
*C07D 498/04* (2006.01)

(52) U.S. Cl. ....................... 514/229.8; 544/95; 623/1.42
(58) Field of Classification Search ............... 514/229.8; 544/95; 623/1.42
See application file for complete search history.

(56) References Cited

PUBLICATIONS

International Preliminary Report on Patentability (Chaper I) in PCT/AU2008/000267 Sep. 8, 2009.
Written Opinion of the International Searching Authority in PCT/AU2008/000267 Apr. 17, 2008.
Fukai, T. et al. "An Isoprenylated Favonanone from *Glycrrhiza glabra* and Ree Assay of Licorice Phenols", Phytochemistry, 49(7), 2005-2013, (1998).
Tsukamoto, S. et al. "CYP3A4 Inhibitors Isolated from Licorice." Biol. Pharm. Bull., 28(10), 2000-2002, (2005).

*Primary Examiner* — Sreeni Padmanabhan
*Assistant Examiner* — Sahar Javanmard
(74) *Attorney, Agent, or Firm* — Wilson, Sonsini, Goodrich & Rosati

(57) ABSTRACT

The invention provides oxazinyl isoflavonoid compounds and compositions containing same, methods for their preparation and their use as therapeutic agents particularly as cardioprotective, anti-inflammatory, anti-oxidant and chemotherapeutic agents.

21 Claims, 20 Drawing Sheets

OXAZINYL ISOFLAVONOID COMPOUNDS, MEDICAMENTS AND USE

CROSS REFERENCE TO RELATED APPLICATIONS

This application is a national phase application under 35 U.S.C. §371 of International Application No. PCT/AU2008/000267, filed Feb. 29, 2008, which claims the benefit of Australian Patent Application Nos. 2007901105, filed Mar. 2, 2007 and 2007904434, filed Aug. 17, 2007, each of which is incorporated by reference.

FIELD OF THE INVENTION

The present invention relates to oxazinyl isoflavonoid compounds and compositions containing same. The invention further relates to methods for preparation of said compounds and uses thereof as therapeutic agents particularly as cardioprotective, anti-inflammatory and anti-oxidant agents finding particular utility in the treatment or prevention of atherosclerosis, restenosis and related diseases and conditions. The compounds also show utility as chemotherapeutic agents.

BACKGROUND OF THE INVENTION

Over 700 different naturally occurring isoflavones are known some of which have biological properties with potential therapeutic benefit. However, despite the considerable research and accumulated knowledge in relation to isoflavones and derivatives thereof, the full ambit of therapeutically useful isoflavonoid compounds and their activities is yet to be realised. Moreover, there is a continual need for new, improved or at least alternative active agents for the treatment, prophylaxis, amelioration, defence against and/or prevention of various diseases and disorders.

A requirement accordingly exists for new generation compounds that exhibit physiological properties important to the health and well-being of animals, particularly humans, and to find new methods which exploit these properties for the treatment, amelioration and prophylaxis of disease. Importantly, there is a strong need to identify new, improved, better and/or alternative pharmaceutical compositions, agents and regimes for the treatment, amelioration or prophylaxis of vascular and inflammatory diseases, and in particular restenosis associated with vascular intervention. Further requirements exist for compounds as cardioprotective agents and methods for inhibiting expression of adhesion molecules in endothelial cells and related activities.

There also exists a requirement for compounds active against the proliferation of cells including cancer and related diseases. There is a further need for chemotherapeutic agents which address some of the undesirable side effects of known agents. There is also a need for different therapies to be available to physicians to combat the numerous and various types of cancers and to provide new options for treatment to address issues of tolerance of proliferating cells to the existing chemotherapeutic agents and treatment regimes. Agents which can at synergistically with other chemotherapeutics are highly sought after.

SUMMARY OF THE INVENTION

Surprisingly, the present inventors have found a novel group of [6,7-e]-1,3-oxazinyl isoflavonoid compounds of the general formula (I) which exhibit important therapeutic activities including strong anti-inflammatory and anti-oxidant activity. The compounds of the invention are therefore indicated for the treatment of atherosclerosis, restenosis, atherogenesis, coronary artery disease and related conditions.

Thus according to an aspect of the present invention there is provided an oxazinyl isoflavonoid compound of the general formula (I):

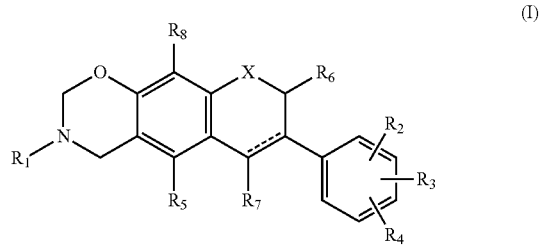

(I)

wherein
$R_1$ is alkyl, cycloalkyl, arylalkyl, alkenyl, alkynyl, aryl or alkylaryl,
$R_2$, $R_3$ and $R_4$ are independently hydrogen, hydroxy, $OR_9$, $OC(O)R_9$, $OSi(R_{10})_3$, alkyl, alkyl, cycloalkyl, aryl, arylalkyl, thiol, alkylthio, nitro, cyano or halo,
$R_5$ is hydrogen, alkyl, cycloalkyl, aryl, arylalkyl, nitro, cyano or halo,
$R_6$ is hydrogen, alkyl, cycloalkyl, aryl, arylalkyl, nitro, cyano or halo,
$R_7$ is hydrogen, alkyl, cycloalkyl, aryl or arylalkyl,
$R_8$ is hydrogen, alkyl, cycloalkyl, aryl, arylalkyl, nitro, cyano or halo,
$R_9$ is alkyl, aryl or arylalkyl,
$R_{10}$ is independently alkyl or aryl,
X is O, $N_{12}$ where $R_{12}$ is alkyl, aryl or arylalkyl, or S, preferably O, and the drawing "═" represents either a single bond or a double bond,
which hydrocarbon substituents can be optionally substituted by one or more of alkyl, halo, acyloxy, hydroxy, halo, alkoxy, silyloxy, nitro and cyano, and
which compounds include pharmaceutically acceptable salts thereof.

According to further aspects and embodiments of the invention there is provided oxazinyl isoflavonoid compounds including those of sub-formulae (I-I) and (I-II) as herein defined below.

According to another aspect of the present invention there is provided a process for the preparation of a compound of formula (I):

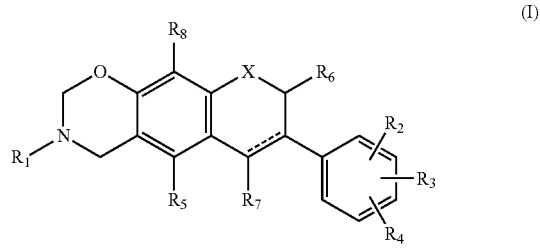

(I)

wherein
$R_1$ is alkyl, cycloalkyl, arylalkyl, alkenyl, alkynyl, aryl or alkylaryl,
$R_2$, $R_3$ and $R_4$ are independently hydrogen, hydroxy, $OR_9$, $OC(O)R_9$, $OSi(R_{10})_3$, alkyl, alkyl, cycloalkyl, aryl, arylalkyl, thiol, alkylthio, nitro, cyano or halo, $R_5$ is hydrogen, alkyl, cycloalkyl, aryl, arylalkyl, nitro, cyano or halo, $R_6$ is hydrogen, alkyl, cycloalkyl, aryl, arylalkyl, nitro, cyano or halo, $R_7$ is hydrogen, alkyl, cycloalkyl, aryl or arylalkyl, $R_8$ is hydrogen, alkyl, cycloalkyl, aryl, arylalkyl, nitro, cyano or halo, $R_9$ is alkyl, aryl or arylalkyl, $R_{10}$ is independently alkyl or aryl, X is O, $N_{12}$ where $R_{12}$ is alkyl, aryl or arylalkyl, or S, preferably O, and the drawing "═" represents either a single bond or a double bond, which hydrocarbon substituents can be optionally substituted by one or more of alkyl, halo, acyloxy, hydroxy, halo, alkoxy, silyloxy, nitro and cyano, comprising the step of reacting an isoflavonoid compound of formula (II):

(II)

wherein $R_2$, $R_3$, $R_4$, $R_5$, $R_6$, $R_7$, $R_8$ and X are as defined above and the drawing "═" represents a single bond or a double bond, with formaldehyde and a primary amine, $R_1$—$NH_2$, wherein $R_1$ is alkyl, cycloalkyl, arylalkyl, alkenyl, alkynyl, aryl or alkylaryl which can be optionally substituted, to form a compound of the general formula (I).

According to another aspect of the present invention there is provided a method for the treatment, prevention or amelioration of a disease or disorder, which comprises administering to a subject one or more compounds of the formula (I) or a pharmaceutically acceptable salt or derivative thereof optionally in association with a carrier and/or excipient.

According to another aspect of the present invention there is provided the use of one or more compounds of formula (I) or a pharmaceutically acceptable salt or derivative thereof in the manufacture of a medicament for the treatment of a disease or disorder.

According to another aspect of the present invention there is provided an agent for the treatment, prophylaxis or amelioration of a disease or disorder which agent comprises one or more compounds of formula (I) or a pharmaceutically acceptable salt or derivative thereof.

According to another aspect of the present invention there is provided a pharmaceutical composition which comprises one or more compounds of formula (I) or a pharmaceutically acceptable salt or derivative thereof in association with one or more pharmaceutical carriers, excipients, auxiliaries and/or diluents.

According to another aspect of the invention there is provided an implantable medical device for delivering an active agent wherein said device comprises an oxazinyl compound of the present invention optionally in association with one or more additional active agents. In an embodiment, the implantable medical device is a drug-eluting stent.

These and other aspects of the invention will become evident from the description and claims which follow, together with the accompanying drawings.

DETAILED DESCRIPTION OF THE INVENTION

Figure 1A:
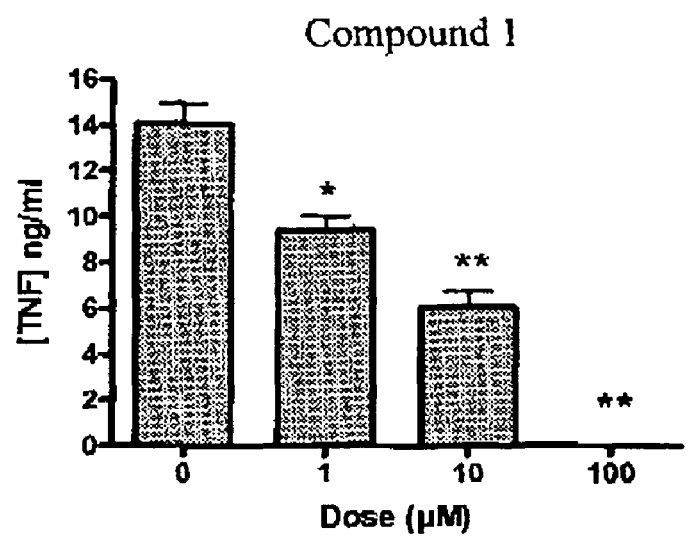
FIGS. 1a and 1b depict the effect of compounds (1) and (2) on the synthesis of TNFα by the human monocytes stimulated with LPS.

The present inventors have found that a class of 1,3-oxazinyl isoflavonoid compounds of the general formula (I) show surprising and unexpected biological and pharmaceutical properties.

The oxazinyl isoflavonoid compounds of the invention also find utility as anti-oxidants, anti-inflammatory agents, cardioprotective agents and for the treatment of vascular disease including restenosis.

As used herein the term "stenosis" is taken in its broadest sense to mean a narrowing or constriction of the diameter of a bodily passage or orifice, such as in particular a blood vessel or artery, and generally leads to reduced blood flow and the concomitant problems of vessel occlusion. Typically stenosis occurs as a result of the focal accumulation and deposit of lipids and other blood derivatives, as well as neointimal proliferation including vascular smooth muscle cells (VSMC).

The term "restenosis" or re-stenosis or secondary stenosis is taken in its broadest sense to mean a recurrence of stenosis typically after vascular intervention, injury or surgery, including balloon angioplasty. Stenosis and restenosis can occur in blood vessels throughout the body, and of particular medical importance is the life threatening and often fatal effects of stenosis in the coronary arteries.

There is now clear evidence for a contributory role of inflammatory processes to restenosis following vascular balloon injury and stent implantation (Schiele 2005). The inflammatory response to acute vessel wall causes monocyte infiltration which aggravates neointimal growth (Schober and Weber 2005).

It is now considered that the oxidant-sensitive regulatory pathway involving nuclear factor κ B (NFκB) plays a central role in the transcription of several atherosclerosis-related genes. Exposure to superoxide ions activates the NFκB regulatory complex and triggers the transcription of genes that encode certain leukocyte adhesion molecules, chemoattractant cytokines and an enzyme that can influence extracellular matrix metabolism. Experimental arterial injury activates NFκB and augments the expression of such genes (Libby and Ganz 1997). The inhibition of NFκB may suppress endothelial activation and induce VSMC apoptosis in atherosclerotic lesions, as well as in developing neointima following angioplasty (Weber and Erl 2000).

Atherosclerosis is a specific example of a chronic inflammatory response mainly to dyslipidaemia and other risk factors. Oxidation of retained lipoproteins may be produced by ROS generated by the cells of inflammatory infiltrates or by enzymes such as lipoxygenases produced by infiltrating macrophages (Getz 2005). Oxidized lipoproteins are thought to provoke a number of changes in cell functions that promote atherogenesis. Oxidized low density lipoprotein (OxLDL) is pro-inflammatory, it can cause endothelial dysfunction and it readily accumulates within the arterial wall (Rosenson 2004).

Oxidative stress also occurs early after angioplasty or stenting (Tardif et al. 2002). Studies in animals have provided evidence of the release of oxidants in response to arterial injury, and macrophages and VSMC, the major types of cell left in the atherosclerotic lesion after angioplasty, can both increase ROS and induce endothelial dysfunction and macrophage activation, resulting in the release of cytokines and growth factors that stimulate matrix remodeling and smooth muscle cell proliferation (Libby and Ganz 1997). The antioxidant Probucol has demonstrated strong activity in reducing post-stenting restenosis and progression of carotid atherosclerosis in clinical trials (Tardif 2005).

Consequently, the antioxidant activity of a compound may contribute to its ability to reduce atherosclerosis as well as restenosis. The robust anti-oxidant activity of the compounds of the invention makes them suitable as free radical scavengers and inhibitors of LDL oxidation.

Early atherosclerosis involves the recruitment of inflammatory cells from the circulation and their transendothelial migration. This process is predominantly mediated by cellular adhesion molecules, which are expressed on the vascular endothelium and on circulating leukocytes in response to several inflammatory stimuli. Selectins (P, E and L) are involved in the rolling and tethering of leukocytes on the vascular wall. Intercellular adhesion molecules (ICAMs) and vascular cell adhesion molecules (VCAM-1), as well as some of the integrins, induce firm adhesion of inflammatory cells at the vascular surface. VCAM-1 expression is restricted to lesions and lesion-predisposed regions whilst ICAM-1 expression is broader and extends into uninvolved aorta and lesion-protected regions.

Increased adhesion molecule expression also plays a part in restenosis. In a prospective study of 46 patients who underwent elective percutaneous transluminal coronary angioplasty (PCTA), those with coronary restenosis at 6-months follow-up showed a significant increase in adhesion molecules on the surface of their circulating monocytes, compared with patients without restenosis (Navarro-Lopez et al. 2003). It has also been surprisingly discovered that the compounds of the invention block the induced expression of the endothelial cell surface adhesion molecules, in particular E-selectin and VCAM-1, in response to many signals known to be active in atherosclerosis, restenosis, inflammatory response and other diseases mediated by cell adhesion molecule expression. This result indicates that the compounds are useful in the treatment or prophylaxis of restenosis, coronary artery diseases, angina and other vascular and cardiovascular diseases, inflammatory diseases mediated by adhesion molecules E-selectin and VCAM-1. The specific molecular mechanisms by which the compounds function in inhibiting cell adhesion molecule expression are not fully understood.

VSMC proliferation is an important step in the atherosclerotic process, as well as a component of the response to vascular injury which occurs with the placement of a stent (McNamara et al. 1996; Rivard and Andres 2000) Consequently, an agent which inhibits proliferation of VSMC is likely to have anti-atherogenic properties. It has further been shown that the compounds of the invention inhibit cellular proliferation of human VSMC. This activity shows the potential for the compounds to prevent the development and progression of atherosclerotic lesions, providing a potential benefit in vascular protection The endothelium regulates VSMC contractility by the production of relaxing and constricting factors in response to physiologic stimuli. Endothelial dysfunction is characterised by impairment of endothelium-dependent vasodilation (EDV) and by pro-coagulant/pro-inflammatory endothelial activities, so the assessment of EDV is a common parameter for testing endothelial function (Patti et al. 2005). Endothelial dysfunction has been associated with a higher risk of restenosis after coronary stent implantation (Patti et al. 2005), perhaps because of failure to maintain a nonadhesive luminal surface (Nabel 1991). DES implantation appears to have an adverse effect on local EDV compared with BMS implantation, which may contribute to the long term problems associated with coated stents (Hofma et al. 2006; Fuke et al. 2007).

The compounds of the invention have also been shown to have potent vascular regulatory capacity. Thus the compounds are capable of antagonising contractile activity, antagonising direct vasodilatation, and protecting against endothelium damage by oxidised low density lipoprotein. Their activities also appear to be unique in their mechanism of action. Thus the compounds again show potential for use as cardioprotective therapeutics including the treatment, amelioration or prophylaxis of restenosis after vascular intervention.

The immune system is an important component of atherosclerotic inflammation (Hansson and Libby 2006). Both T- and B-lymphocytes can modulate the progression of atherogenesis, primarily through cytokine secretion and immunoglobulin production respectively (Vanderlaan and Reardon 2005). Atherosclerotic plaques contain numerous T cells, the majority of which are CD4+ cells, although smaller numbers of CD8+ cells have been detected (Getz 2005; Hansson and Libby 2006). Among the CD4+ cells are several subgroups, including Th1 cells which mainly secrete proinflammatory cytokines eg INFγ, and Th2 cells which may be anti-inflammatory and do not produce INFγ. The pattern of cell and cytokine involvement suggests a Th1 dominance in atherosclerotic lesions. INFγ would appear to have a pro-atherogenic role—atherosclerotic lesions are increased in both INFγ$^{-/-}$ mice and where recombinant INFγ is injected into hyperchlolesterolaemic mice (Getz 2005). IFNγ activates macrophages (the most prominent cell type in plaques), thereby increasing their production of NO, pro-inflammatory cytokines, and pro-thrombotic and vasoactive mediators.

T cells also produce TNFα, another pro-inflammatory cytokine which can activate the NFκB pathway, in turn causing the production of ROS (Hansson et al. 2002). TNFα also has marked metabolic effects that include the suppression of lipoprotein lipase, which leads to the accumulation of triglyceride-rich lipoproteins in the blood. Increases in both lipoproteins and the TNFα have been associated with heart disease in clinical studies (Hansson and Libby 2006).

Experimentally, B cells have been shown to be atheroprotective, because eliminating them either genetically or through splenectomy increases atherosclerosis, and this action may be because of the production of α-OxLDL antibodies (Vanderlaan and Reardon 2005). B cells can regulate the immune response directly through cytokine secretion as well. Under certain conditions, B cells are able to produce a variety of cytokines once thought to be restricted to T-cells, including IL-6, IFN-γ and TNFα. T cells are found within the actual plaque; B cells are rarely present, but they are common among the neighbouring adventitia.

As with primary atherosclerosis, restenosis following stenting is also associated with inflammatory and immunological activity. Restenotic lesions are infiltrated with inflammatory cells (monocytes and macrophages) and T cells (Navarro-Lopez et al. 2003). In the prospective study of patients with elective PCTA cited earlier, those with coronary restenosis at 6-months follow-up also showed a significant increase in circulating cytotoxic T-lymphocytes compared to baseline figures; reaching higher levels than patients without restenosis (Navarro-Lopez et al. 2003).

IL-6 is a pro-inflammatory cytokine associated with the acute phase response. IL-6 levels are also associated with subclinical atherosclerotic lesions independently of traditional risk factors, and the influence of IL-6 on ICAM-1 secretion may play a role in this association (Amar et al. 2006). An increased level of IL-6 sampled from the area surrounding the coronary artery occlusion/stent has also been associated with restenosis following percutaneous coronary intervention (PCI) and PCTA (Hojo et al. 2000; Funayama et al. 2006). As well, patients with restenosis have increased levels of circulating 1L-6 and TNFα (Navarro-Lopez et al. 2003).

The oxazinyl isoflavonoid compounds can also be administered to treat small vessel disease that is not treatable by surgery or angioplasty, or other vessel disease in which surgery is not an option, and to stabilise patients prior to and after revascularisation therapy. The active compounds can also be administered in the period immediately prior to and following vascular intervention such as coronary or vascular angioplasty as a means to reduce or eliminate the abnormal proliferative and inflammatory response that currently leads to clinically significant restenosis. Further, the compounds can also be used in the treatment of cardiac transplant rejection and vascular graft and transplant procedures.

The methods of this invention represent a significant advance in treating vascular conditions and disease, in that they go beyond well known therapies designed simply to inhibit the progression of disease. The experimental data provided herein has unexpectedly shown that restenosis after vascular intervention or angioplasty is inhibited or at least markedly reduced in various mammalian animal models. Thus, when used appropriately, the present methods demonstrate the potential of isoflavone compounds and derivatives thereof to medically address restenosis, and possibly to cure atherosclerosis by preventing new lesions from developing and causing established lesions to stabilise or regress.

The compounds of formula (I) of the invention are shown to have favourable toxicity profiles with normal cells and good bioavailability. The compounds of the invention exhibit anti-cancer activity significantly better than, comparable to or at least as a useful alternative to existing cancer treatments.

The compounds of formula (I) are cytostatic and cytotoxic against a broad range of cancer cells of human and animal origin. By cancer cells, it is meant cells that display malignant characteristics and which are distinguished from non-cancer cells by unregulated growth and behaviour which usually ultimately is life-threatening unless successfully treated.

The cancer cells that have been found to be responsive to compounds of formula (I) are of epithelial origin (for example, prostate, ovarian, cervical, breast, gall-bladder, pancreatic, colorectal, renal, and non-small lung cancer cells), of mesenchymal origin (for example, melanoma, mesothelioma and sarcoma cancer cells), and of neural origin (for example glioma cancer cells). It is highly unusual and surprising to find a related group of compounds that display such potent cytotoxicity against cancer cells, but with low toxicity against non-cancer cells such as keratinocytes derived from human foreskin. Such cancer cell selectivity is highly unusual and unexpected.

Advantageously the compounds of formula (I) show cytotoxicity against cancer cells that are well recognised for being poorly sensitive to standard anti-cancer drugs. It is highly unusual and unexpected to find such potent activity against cancers, for example, melanoma, colon adenocarcinoma and ovarian, breast and lung cancers.

Thus, the invention also provides the use of compounds of formula (I) to treat patients with cancer by either reducing the rate of growth of such tumours or by reducing the size of such tumours through therapy with said compounds alone, and/or in combination with each other, and/or in combination with other anti-cancer agents, and/or in combination with radiotherapy.

The use of compounds of the present invention either alone or in combination therapy as described above may reduce the adverse side-effects often experienced by patients when treated with standard anti-cancer treatments. The use of compounds of the invention may mean that lower doses can be employed in such therapy which represents an important advance for cancer sufferers.

The properties described above offer significant clinical advantages.

In a preferred embodiment of the invention there is provided and oxazinyl isoflavonoid compound of the formula (I-I):

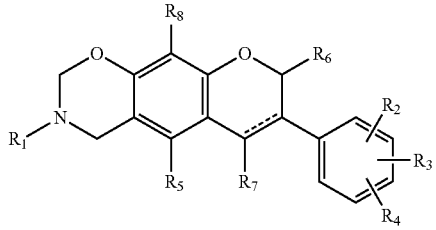

wherein $R_1$ is alkyl, cycloalkyl, arylalkyl, alkenyl, alkynyl, aryl or alkylaryl, $R_2$, $R_3$ and $R_4$ are independently hydrogen, hydroxy, $OR_9$, $OC(O)R_9$, $OSi(R_{10})_3$, alkyl, alkyl, cycloalkyl, aryl, arylalkyl, thiol, alkylthio, nitro, cyano or halo, $R_5$ is hydrogen, alkyl, cycloalkyl, aryl, arylalkyl, nitro, cyano or halo, $R_6$ is hydrogen, alkyl, cycloalkyl, aryl, arylalkyl, nitro, cyano or halo, $R_7$ is hydrogen, alkyl, cycloalkyl, aryl or arylalkyl, $R_8$ is hydrogen, alkyl, cycloalkyl, aryl, arylalkyl, nitro, cyano or halo, $R_9$ is alkyl, aryl or arylalkyl, $R_{10}$ is independently alkyl or aryl, and the drawing "$\equiv$" represents either a single bond or a double bond, which hydrocarbon substituents can be optionally substituted by one or more of alkyl, halo, acyloxy, hydroxy, halo, alkoxy, silyloxy, nitro and cyano, and which compounds include pharmaceutically acceptable salts thereof.

More preferably, there is provided a compound of the formula (I-II):

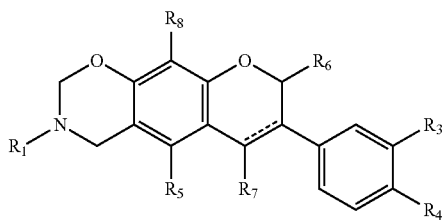

wherein $R_1$ is alkyl, arylalkyl, aryl or alkylaryl, $R_3$ and $R_4$ are independently hydrogen, hydroxy, $OR_9$, $OC(O)R_9$, $OSi(R_{10})_3$, alkyl, alkyl, arylalkyl, nitro, cyano or halo, $R_5$ is hydrogen, alkyl or halo, $R_6$ is hydrogen or alkyl, $R_7$ is hydrogen, alkyl or aryl, $R_8$ is hydrogen, alkyl or halo, $R_9$ is alkyl or arylalkyl, $R_{10}$ is independently alkyl, and the drawing "$\equiv$" represents either a single bond or a double bond, which hydrocarbon substituents can be optionally substituted by one or more of alkyl, halo, acyloxy, hydroxy, halo, alkoxy, silyloxy, nitro and cyano, and which compounds include pharmaceutically acceptable salts thereof;

more preferably wherein $R_1$ is alkyl, phenylalkyl, phenyl, naphthylalkyl, naphthyl or alkylphenyl, $R_3$ and $R_4$ are independently hydrogen, hydroxy, $OR_9$, $OC(O)R_9$, alkyl, nitro, cyano or halo, and where at least one of $R_3$ and $R_4$ is not hydrogen, $R_5$ is hydrogen, alkyl or halo, $R_6$ is hydrogen or alkyl, $R_7$ is hydrogen or phenyl, $R_8$ is hydrogen, alkyl or halo, $R_9$ is alkyl, and the drawing "$\equiv$" represents either a single bond or a double bond, which hydrocarbon substituents can be optionally substituted by one or more of alkyl, halo, acyloxy, hydroxy, halo, alkoxy, nitro and cyano, and which compounds include pharmaceutically acceptable salts thereof;

still more preferably wherein $R_1$ is methyl, ethyl, propyl, isopropyl, butyl, phenylmethyl, 1-phenylethyl, phenyl, naphthylmethyl, naphthyl or alkylphenyl optionally substituted by alkyl, halo, hydroxy, acetyloxy, methoxy, ethoxy, nitro or cyano, $R_3$ and $R_4$ are independently hydrogen, hydroxy and methoxy, and where at least one of $R_3$ and $R_4$ is not hydrogen, $R_5$ is hydrogen, methyl or halo, $R_6$ is hydrogen, methyl or ethyl, $R_7$ is hydrogen or phenyl optionally substituted by alkyl, halo, hydroxy, methoxy, nitro or cyano, $R_8$ is hydrogen, methyl or halo, the drawing "$\equiv$" represents either a single bond or a double bond, and which compounds include pharmaceutically acceptable salts thereof; and more preferably wherein $R_1$ is methyl, ethyl, propyl, phenylmethyl, 1-phenylethyl, phenyl, naphthylmethyl or methylphenyl optionally substituted by methyl, halo, hydroxy, methoxy, nitro or cyano, $R_3$ and $R_4$ are independently hydrogen, hydroxy and methoxy, and where at least one of $R_3$ and $R_4$ is not hydrogen, $R_5$ is hydrogen, $R_6$ is hydrogen, $R_7$ is hydrogen or phenyl optionally substituted by methoxy, $R_8$ is hydrogen, the drawing "$\equiv$" represents either a single bond or a double bond, and which compounds include pharmaceutically acceptable salts thereof.

In a preferred embodiment, halo is chloro or bromo.

In another preferred embodiment, $R_1$ is benzyl (phenylmethyl).

In another preferred embodiment, $R_1$ is 1-phenylethyl.

In another preferred embodiment, $R_1$ is alkyl or alkoxyalkyl, more preferably methyl, propyl or 3-methoxypropyl.

In another preferred embodiment, $R_1$ is phenyl or benzyl substituted with nitro, alkyl, alkoxy, preferably methoxy, or halo, preferably chloro.

In another preferred embodiment, $R_1$ is naphthylmethyl.

In another preferred embodiment, $R_3$ is hydroxyl.

In another preferred embodiment, $R_4$ is hydroxyl.

In another preferred embodiment, $R_3$ and $R_4$ are methoxy.

In another preferred embodiment, $R_8$ is alkyl, more preferably methyl.

In another preferred embodiment, $R_8$ is halo, more preferably bromo.

In another preferred embodiment, the drawing "═" represents a double bond.

In another preferred embodiment, the drawing "═" represents a single bond.

Especially preferred compounds of formula (I) are compounds (1) to (32):

4-(3-Benzyl-2,3,4,8-tetrahydrochromeno[6,7-e][1,3]oxazin-7-yl)phenol (1)
4-(3-(1-Phenylethyl)-2,3,4,8-tetrahydrochromeno[6,7-e][1,3]oxazin-7-yl)phenol (2)
4-(3-Propyl-2,3,4,8-tetrahydrochromeno[6,7-e][1,3]oxazin-7-yl)phenol (3)
4-(3-methyl-2,3,4,8-tetrahydrochromeno[6,7-e][1,3]oxazin-7-yl)phenol (4)
7-(3,4-Dimethoxyphenyl)-3-propyl-2,3,4,8-tetrahydrochromeno[6,7-e][1,3]oxazine (5)
4-(3-(4-Methoxybenzyl)-2,3,4,8-tetrahydrochromeno[6,7-e][1,3]oxazin-7-yl)phenol (6)
4-(3-Phenyl-2,3,4,8-tetrahydrochromeno[6,7-e][1,3]oxazin-7-yl)phenol (7)
4,4'-(Chromeno[6,7-e][1,3]oxazine-3,7 (2H,4H,8H)-diyl)diphenol (8)
7-(3,4-Dimethoxyphenyl)-3-(4-methoxybenzyl)-2,3,4,8-tetrahydrochromeno[6,7-e][1,3]oxazine (9)
3-(3-Benzyl-2,3,4,8-tetrahydrochromeno[6,7-e][1,3]oxazin-7-yl)phenol (10)
3-(3-Phenyl-2,3,4,8-tetrahydrochromeno[6,7-e][1,3]oxazin-7-yl)phenol (11)
7-(3,4-Dimethoxyphenyl)-3-phenyl-2,3,4,8-tetrahydrochromeno[6,7-e][1,3]oxazine (12)
3-Benzyl-7-(3,4-dimethoxyphenyl)-10-methyl-2,3,4,8-tetrahydrochromeno[6,7-e][1,3]oxazine (13)
7-(3,4-Dimethoxyphenyl)-10-methyl-3-propyl-2,3,4,8-tetrahydrochromeno[6,7-e][1,3]oxazine (14)
4-(3-(4-Chlorobenzyl)-2,3,4,8-tetrahydrochromeno[6,7-e][1,3]oxazin-7-yl)phenol (15)
4-(3-(3-Methoxypropyl)-2,3,4,8-tetrahydrochromeno[6,7-e][1,3]oxazin-7-yl)phenol (16)
3-(3-(3-Methoxypropyl)-2,3,4,8-tetrahydrochromeno[6,7-e][1,3]oxazin-7-yl)phenol (17)
4-(3-p-Tolyl-2,3,4,8-tetrahydrochromeno[6,7-e][1,3]oxazin-7-yl)phenol (18)
7-(3,4-Dimethoxyphenyl)-10-methyl-3-p-tolyl-2,3,4,8-tetrahydrochromeno[6,7-e][1,3]oxazine (19)
3-(3-p-Tolyl-2,3,4,8-tetrahydrochromeno[6,7-e][1,3]oxazin-7-yl)phenol (20)
4-(7-(3-Hydroxyphenyl)chromeno[6,7-e][1,3]oxazin-3(2H,4H,8H)-yl)benzonitrile (21)
4-(3-m-Tolyl-2,3,4,8-tetrahydrochromeno[6,7-e][1,3]oxazin-7-yl)phenol (22)
4-(3-(3-Nitrophenyl)-2,3,4,8-tetrahydrochromeno[6,7-e][1,3]oxazin-7-yl)phenol (23)
4-(3-(4-Chlorobenzyl)-6-(4-methoxyphenyl)-2,3,4,8-tetrahydrochromeno[6,7-e][1,3]oxazin-7-yl)-phenol (24)
4-(10-Bromo-3-propyl-2,3,4,8-tetrahydrochromeno[6,7-e][1,3]oxazin-7-yl)phenol (25)
3,4'-(10-Methyl-chromeno[6,7-e][1,3]oxazine-3,7(2H,4H,8H)-diyl)diphenol (26)
4-(8-Ethyl-3-propyl-2,3,4,8-tetrahydrochromeno[6,7-e][1,3]oxazin-7-yl)phenol (27)
4-(3-(4-tert-Butylphenyl)-2,3,4,8-tetrahydrochromeno[6,7-e][1,3]oxazin-7-yl)phenol (28)
4-(3-(4-tert-Butylbenzyl)-2,3,4,8-tetrahydrochromeno[6,7-e][1,3]oxazin-7-yl)phenol (29)
4-(3-(Naphth-1-yl-methyl)-2,3,4,8-tetrahydrochromeno[6,7-e][1,3]oxazin-7-yl)phenol (30)
4-(3-(3,4-Dimethylphenyl)-2,3,4,8-tetrahydrochromeno[6,7-e][1,3]oxazin-7-yl)phenol (31)
4-(3-(4-Methoxyphenyl)-2,3,4,8-tetrahydrochromeno[6,7-e][1,3]oxazin-7-yl)phenol (32)

or a pharmaceutically acceptable salt thereof.

Particularly preferred compounds of the present invention as antioxidants and free radical scavengers are compounds (1), (2), (3), (8), (16) and (17).

Particularly preferred compounds of the present invention as inhibitors of VSMC are compounds (1), (7), (8), (17), (18), (19) and (20).

Particularly preferred compounds of the present invention as anticancer agents are compounds (1), (2), (6), (16) and (17).

Particularly preferred compounds of the present invention as PPARγ agonists are compounds (1), (2), (6), (7), (18), (20), (22), (23), (27) and (29).

The compounds of formula (I) according to the invention can have chiral centres. The present invention includes all the enantiomers and diastereoisomers as well as mixtures thereof in any proportions. The invention also extends to isolated enantiomers or pairs of enantiomers. Methods of separating enantiomers and diastereoisomers are well known to person skilled in the art.

The term "isoflavone" or isoflavonoid compound" as used herein is to be taken broadly to include as isoflavones, isoflavenes, isoflavans, isoflavanones, isoflavanols and the like where a specific meaning is not intended.

The term "alkyl" is taken to include straight chain and branched chain saturated alkyl groups of 1 to 6 carbon atoms, such as methyl, ethyl, propyl, isopropyl, butyl, isobutyl, secbutyl, tertiary butyl, pentyl and the like. The alkyl group more preferably contains preferably from 1 to 4 carbon atoms, especially methyl, ethyl, propyl or isopropyl.

Cycloalkyl includes cyclic alkyl groups of 3 to 6 carbon atoms such as cyclopropyl, cyclobutyl, cyclopentyl and cyclohexyl.

The alkyl, alkenyl or allynyl groups or cycloalkyl group may optionally be substituted by one or more of alkyl, halo, acyloxy, hydroxy, halo, alkoxy, silyloxy, nitro and cyano.

The term "aryl" is taken to include phenyl, benzyl, biphenyl and naphthyl and may be optionally substituted by one or more of alkyl, halo, acyloxy, hydroxy, halo, alkoxy, silyloxy, nitro and cyano.

The term "halo" is taken to include fluoro, chloro, bromo and iodo, preferably fluoro and chloro. Reference to for example "haloalkyl" will include monohalogenated, dihalogenated and up to perhalogenated alkyl groups. Preferred perhaloalkyl groups are trifluoromethyl and pentafluoroethyl.

The term "silyloxy" group typically refers to peralkylsilyloxy such as trimethylsilyloxy or t-butyldimethylsilyloxy.

The compounds of the invention include all salts, such as acid addition salts, anionic salts and zwitterionic salts, and in particular include pharmaceutically acceptable salts as would be known to those skilled in the art. The term "pharmaceutically acceptable salt" refers to an organic or inorganic moiety that carries a charge and that can be administered in association with a pharmaceutical agent, for example, as a counter-cation or counter-anion in a salt. Pharmaceutically acceptable cations are known to those of skilled in the art, and include but are not limited to sodium, potassium, calcium, zinc and quaternary amine. Pharmaceutically acceptable anions are known to those of skill in the art, and include but are not limited to chloride, acetate, tosylate, citrate, bicarbonate and carbonate.

Pharmaceutically acceptable salts include those formed from: acetic, ascorbic, aspartic, benzoic, benzenesulphonic, citric, cinnamic, ethanesulphonic, fumaric, glutamic, glutaric, gluconic, hydrochloric, hydrobromic, lactic, maleic, malic, methanesulphonic, naphthoic, hydroxynaphthoic, naphthalenesulphonic, naphthalenedisulphonic, naphthaleneacrylic, oleic, oxalic, oxaloacetic, phosphoric, pyruvic, p-toluenesulphonic, tartaric, trifluoroacetic, triphenylacetic, tricarballylic, salicylic, sulphuric, sulphamic, sulphanilic and succinic acid.

The term "pharmaceutically acceptable derivative" or "prodrug" refers to a derivative of the active compound that upon administration to the recipient is capable of providing directly or indirectly, the parent compound or metabolite, or that exhibits activity itself and includes for example phosphate derivatives and sulphonate derivatives. Thus, derivatives include solvates, pharmaceutically active esters, prodrugs or the like. This also includes derivatives with physiologically cleavable leaving groups that can be cleaved in vivo to provide the compounds of the invention or their active moiety. The leaving groups may include acyl, phosphate, sulfate, sulfonate, and preferably are mono-, di- and per-acyl oxy-substituted compounds, where one or more of the pendant hydroxy groups are protected by an acyl group, preferably an acetyl group. Typically acyloxy substituted compounds of the invention are readily cleavable to the corresponding hydroxy substituted compounds.

Chemical functional group protection, deprotection, synthons and other techniques known to those skilled in the art may be used where appropriate to aid in the synthesis of the compounds of the present invention, and their starting materials.

The protection of functional groups on the compounds and derivatives of the present invention can be carried out by well established methods in the art, for example as described in T. W. Greene, *Protective Groups in Organic Synthesis*, John Wiley & Sons, New York, 1981.

Hydroxyl protecting groups include but are not limited to carboxylic acid esters, eg acetate esters, aryl esters such as benzoate, acetals/ketals such as acetonide and benzylidene, ethers such as o-benzyl and p-methoxy benzyl ether, tetrahydropyranyl ether and silyl ethers such as t-butyldimethyl silyl ether.

Protecting groups can be removed by, for example, acid or base catalysed hydrolysis or reduction, for example, hydrogenation. Silyl ethers may require hydrogen fluoride or tetrabutylammonium fluoride to be cleaved.

It will be clear to persons skilled in the art of medicinal chemistry that compounds of formula (I) may be converted into other compounds of formula (I), for example, where a compound of formula (I) bears one or more hydroxyl substituents then one or more of these substituents can be converted in to a halo substituent such as bromo, chloro or iodo by treating the alcohol with a halogenating agent. Halogenating agents include compounds like NBS, hydrobromic acid, chlorine gas etc. It may be necessary during processes such as halogenation to use protecting groups to protect other functionality in the molecule.

Phenolic type hydroxyls may not be readily convertible to the corresponding halogen compound by treatment with a halogenating agent. However, the desired halogen compound may be prepared by, for example, treating an appropriate aryl amine starting material with $NaNO_2$ in the presence of HCl under reduced temperature conditions such as 0° C., to form the corresponding azide salt. Subsequent treatment with CuCl, CuBr, KI or $HBF_4$ may be used to convert the azide into the required halo-compound.

A general process for preparing compounds of formula (I) comprises the step of treating a compound of formula (II):

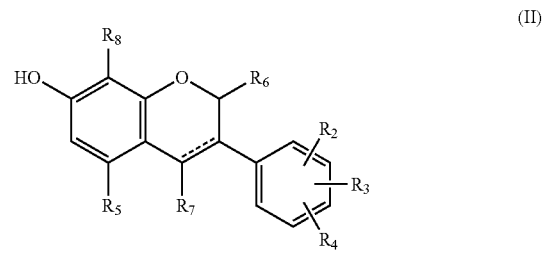

(II)

wherein $R_1$, $R_2$, $R_3$, $R_4$, $R_5$, $R_6$, $R_7$, $R_8$ and X are as defined above and the drawing "═" represents a single bond or a double bond, preferably a double bond, with formaldehyde and a primary amine, $R_1$—$NH_2$, wherein $R_1$ is alkyl, cycloalkyl, arylalkyl, alkenyl, alkynyl, aryl or alkylaryl which can be optionally substituted to form the compound of the general formula (I).

These conditions are generally referred to as a Mannich reaction and also involve a ring closure to form the 1,3-oxazine ring onto the isoflavonoid A-ring. Similar methods and variations as known in the art may also be employed to bring about the oxazine synthesis such as is described in Shigernasa, et al., *Tetrahedron Letters*, 42 (2001) 7273-7275.

When the drawing "═" represents a double bond standard hydrogenation methods with hydrogen and a catalyst may be used to make the corresponding oxazine isoflavan compounds where "═" now represents a single bond. Reducing agents are well known to persons skilled in the art and can include hydride sources like borohydrides and alkali metal borohydrides, but would include hydrogen in catalytic hydrogenation where a suitable catalyst such as palladium on carbon may be used. Other suitable hydride sources include sodium triacetoxyborohydride tetrabutyl ammonium triacetoxyborohydride and sodium cyanoborohydride. Preferably the double bond when present is reduced by hydrogenation over Palladium-on-Carbon.

Access to isoflavone compounds of general formula (III) may be derived from any number of sources readily identifiable to a person skilled in the art. For example, daidzein (4',7-dihydroxyisoflavone) and analogues are readily available or can be synthesised by the general synthetic method as set out in Scheme I below and as described in published International application Nos. WO 98/08503 and WO01/17986, and references cited therein, the disclosures of which are incorporated herein by reference. A typical synthesis is depicted in Scheme 1

Scheme 1

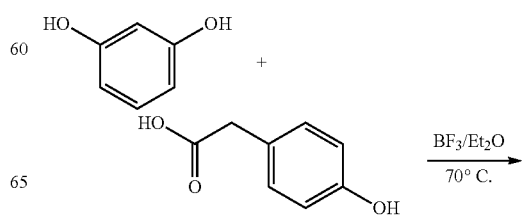

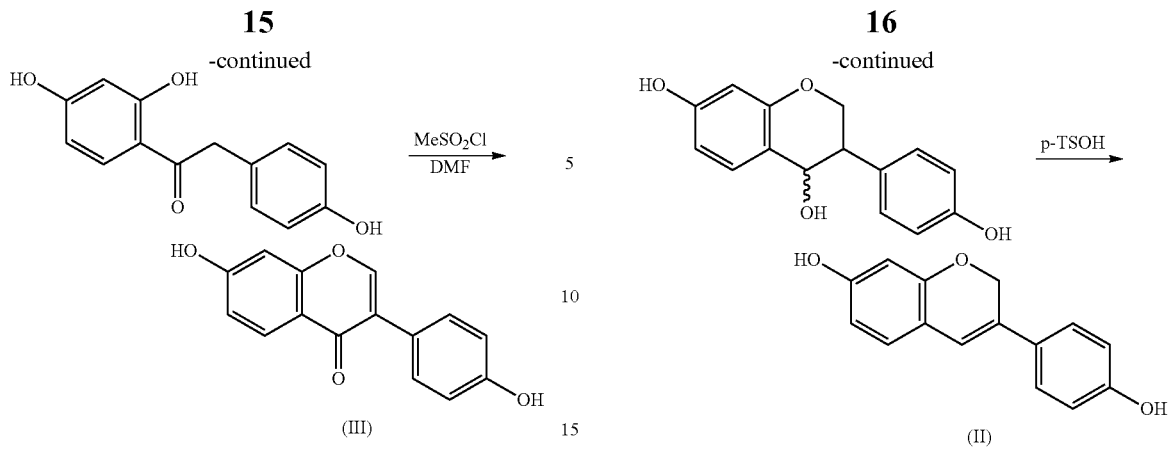

Access to the various 3-phenyl substituted isoflavones is available by varying the substitution pattern on the phenylacetic acid derived group, or chemical modification thereof with protecting groups and synthons as known in the art.

Likewise, access to the 5- and/or the 8-substituted isoflavones is available by varying the substitution pattern on the resorcinol group.

Access to isoflav-3-ene and isoflavan compounds of general formula (II) is available by the general synthetic method as set out in Scheme 2 below and as described in published International application Nos. WO 00/49009 and WO01/17986, and references cited therein, the disclosures of which are incorporated herein by reference. A typical synthesis is depicted in Scheme 2

Scheme 2

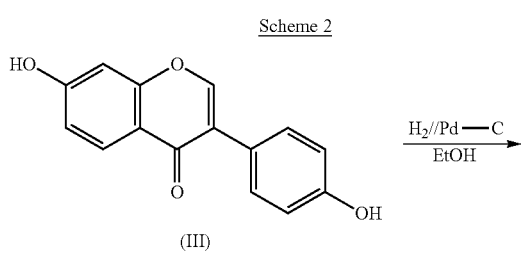

The hydrogenation and dehydration reactions generally work better when the phenol moieties when present are first protected, such as for example as acyloxy or silyloxy groups. The products can then be readily deprotected to generate the corresponding hydroxy-substituted compounds.

Access to 4-substituted isoflavonoid compounds is available for example by Grignard reactions on isoflavans-4-one compounds such as the protected 4',7-disilyloxy dihydrodaidzein according to the general synthetic method as set out in Scheme 3 below and as described in published International application No. WO 2006/032086, and references cited therein, the disclosures of which are incorporated herein by reference. A typical synthesis is depicted in Scheme 3

Scheme 3

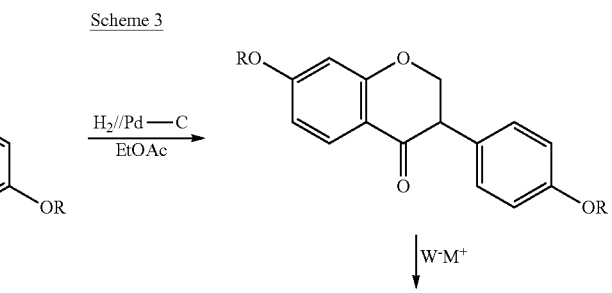

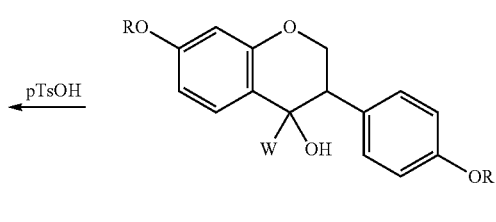

Access to 2-substituted isoflavonoid compounds is available for example from a suitably protected isoflav-3-ene compound. The corresponding isoflavylium salt intermediate is formed with trityl hexafluorophosphate followed by nucleophilic addition. Nucleophiles can include trimethyl silyl (TMS) derivatives, tributyl tin ((Bu)$_3$Sn) derivatives, alcohols, amines and the like. A general synthesis is depicted in Scheme 4

Scheme 4

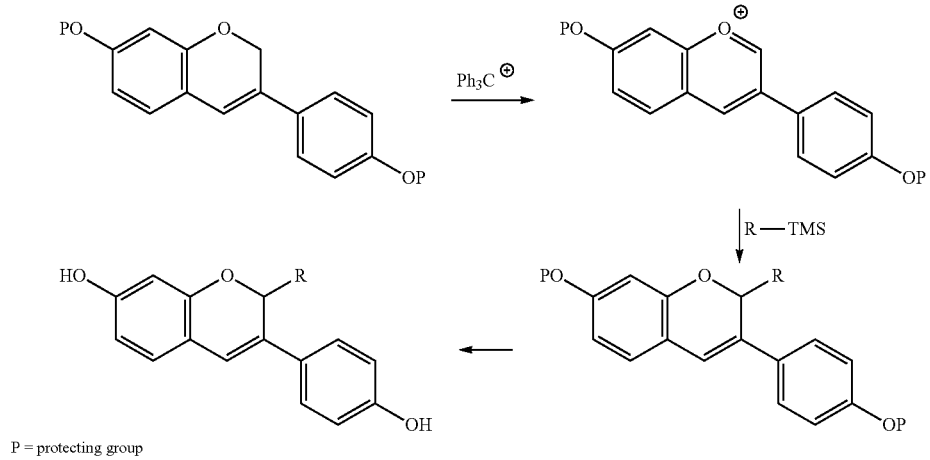

P = protecting group

As used herein, the terms "treatment", "prophylaxis" or "prevention", "amelioration" and the like are to be considered in their broadest context. In particular, the term "treatment" does not necessarily imply that an animal is treated until total recovery. Accordingly, "treatment" includes amelioration of the symptoms or severity of a particular condition or preventing or otherwise reducing the risk of developing a particular condition.

The amount of one or more compounds of formula (I) which is required in a therapeutic treatment according to the invention will depend upon a number of factors, which include the specific application, the nature of the particular compound used, the condition being treated, the mode of administration and the condition of the patient.

Compounds of formula (I) may be administered in a manner and amount as is conventionally practised. See, for example, Goodman and Gilman, "The pharmacological basis of therapeutics", 7th Edition, (1985). The specific dosage utilised will depend upon the condition being treated, the state of the subject, the route of administration and other well known factors as indicated above. In general, a daily dose per patient may be in the range of 0.1 mg to 5 g; typically from 0.5 mg to 1 g; preferably from 50 mg to 200 mg. The length of dosing may range from a single dose given once every day or two, to twice or thrice daily doses given over the course of from a week to many months to many years as required, depending on the severity of the condition to be treated or alleviated.

It will be further understood that for any particular subject, specific dosage regimens should be adjust over time according to the individual need and the professional judgment of the person administering or supervising the administration of the compositions.

Relatively short-term treatments with the active compounds can be used to cause stabilisation or shrinkage or remission of cancers. Longer-term treatments can be employed to prevent the development of cancers in high-risk patients.

The production of pharmaceutical compositions for the treatment of the therapeutic indications herein described are typically prepared by admixture of the compounds of the invention (for convenience hereafter referred to as the "active compounds") with one or more pharmaceutically or veterinary acceptable carriers and/or excipients as are well known in the art.

The carrier must, of course, be acceptable in the sense of being compatible with any other ingredients in the formulation and must not be deleterious to the subject. The carrier or excipient may be a solid or a liquid, or both, and is preferably formulated with the compound as a unit-dose, for example, a tablet, which may contain up to 100% by weight of the active compound, preferably from 0.5% to 59% by weight of the active compound.

One or more active compounds may be incorporated in the formulations of the invention, which may be prepared by any of the well known techniques of pharmacy consisting essentially of admixing the components, optionally including one or more accessory ingredients. The preferred concentration of active compound in the drug composition will depend on absorption, distribution, inactivation, and excretion rates of the drug as well as other factors known to those of skill in the art.

The formulations of the invention include those suitable for oral, rectal, ocular, buccal (for example, sublingual), parenteral (for example, subcutaneous, intramuscular, intradermal, or intravenous), transdermal administration including mucosal administration via the nose, mouth, vagina or rectum, and as inhalants, although the most suitable route in any given case will depend on the nature and severity of the condition being treated and on the nature of the particular active compound which is being used.

Formulation suitable for oral administration may be presented in discrete units, such as capsules, sachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture such as to form a unit dosage. For example, a tablet may be prepared by compressing or moulding a powder or granules containing the active compound, optionally with one or more other ingredients.

Compressed tablets may be prepared by compressing, in a suitable machine, the compound of the free-flowing, such as a powder or granules optionally mixed with a binder, lubricant, inert diluent, and/or surface active/dispersing agent(s). Moulded tablets may be made by moulding, in a suitable machine, the powdered compound moistened with an inert liquid binder.

Formulations suitable for buccal (sublingual) administration include lozenges comprising the active compound in a flavoured base, usually sucrose and acacia or tragacanth; and pastilles comprising the compound in an inert base such as gelatine and glycerin or sucrose and acacia.

Formulations suitable for ocular administration include liquids, gels and creams comprising the active compound in an ocularly acceptable carrier or diluent.

Compositions of the present invention suitable for parenteral administration conveniently comprise sterile aqueous preparations of the active compounds, which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the compound with water or a glycine buffer and rendering the resulting solution sterile and isotonic with the blood. Injectable formulations according to the invention generally contain from 0.1% to 60% w/v of active compound and can be administered at a rate of 0.1 ml/minute/kg.

Formulations for infusion, for example, may be prepared employing saline as the carrier and a solubilising agent such as a cyclodextrin or derivative thereof. Suitable cyclodextrins include α-cyclodextrin, β-cyclodextrin, γ-cyclodextrin, dimethyl-β-cyclodextrin, 2-hydroxyethyl-β-cyclodextrin, 2-hydroxypropyl-cyclodextrin, 3-hydroxypropyl-β-cyclodextrin and tri-methyl-β-cyclodextrin. More preferably the cyclodextrin is hydroxypropyl-β-cyclodextrin. Suitable derivatives of cyclodextrins include Captisol® a sulfobutyl ether derivative of cyclodextrin and analogues thereof as described in U.S. Pat. No. 5,134,127.

Formulations suitable for rectal administration are preferably presented as unit dose suppositories. Formulations suitable for vaginal administration are preferably presented as unit dose pessaries. These may be prepared by admixing the active compound with one or more conventional solid carriers, for example, cocoa butter, and then shaping the resulting mixture.

Formulations or compositions suitable for topical administration to the skin preferably take the form of an ointment, cream, lotion, paste, gel, spray, aerosol, or oil. Carriers which may be used include Vasoline, lanoline, polyethylene glycols, alcohols, and combination of two or more thereof. The active compound is generally present at a concentration of from 0.1% to 5% w/w, more particularly from 0.5% to 2% w/w. Examples of such compositions include cosmetic skin creams.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 M to 0.2 M concentration with respect to the said active compound. See for example Brown, L., a al. (1998).

Formulations suitable for transdermal administration may also be delivered by iontophoresis (see, for example, Panchagnula R, et al., 2000) and typically take the form of an optionally buffered aqueous solution of the active compound. Suitable formulations comprise citrate or Bis/Tris buffer (pH 6) or ethanol/water and contain from 0.1 M to 0.2 M active ingredient.

Formulations suitable for inhalation may be delivered as a spray composition in the form of a solution, suspension or emulsion. The inhalation spray composition may further comprise a pharmaceutically acceptable propellant such as carbon dioxide or nitrous oxide or a hydrogen containing fluorocarbon such as 1,1,1,2-tetrafluoroethane, 1,1,1,2,3,3,3-heptafluoro-n-propane or mixtures thereof.

The active compounds may be provided in the form of food stuffs, such as being added to, admixed into, coated, combined or otherwise added to a food stuff. The term food stuff is used in its widest possible sense and includes liquid formulations such as drinks including dairy products and other foods, such as health bars, desserts, etc. Food formulations containing compounds of the invention can be readily prepared according to standard practices.

Therapeutic methods, uses and compositions may be for administration to humans or other animals, including mammals such as companion and domestic animals (such as dogs and cats) and livestock animals (such as cattle, sheep, pigs and goats), birds (such as chickens, turkeys, ducks), marine animals including those in the aquaculture setting (such as fish, crustaceans and shell fish) and the like.

The active compound or pharmaceutically acceptable derivatives prodrugs or salts thereof can also be co-administered with other active materials that do not impair the desired action, or with materials that supplement the desired action, such as antibiotics, antifungals, antiinflammatories, or antiviral compounds. The active agent can comprise two or more isoflavones or derivatives thereof in combination or synergistic mixture. The active compounds can also be administered with lipid lowering agents such as probucol and nicotinic acid; platelet aggregation inhibitors such as aspirin; antithrombotic agents such as coumadin; calcium channel blockers such as verapamil, diltiazem, and nifedipine; angiotensin converting enzyme (ACE) inhibitors such as captopril and enalapril, and β-blockers such as propanolol, terbutalol, and labetalol. The compounds can also be administered in combination with nonsteriodal antiinflammatories such as ibuprofen, indomethacin, aspirin, fenoprofen, mefenamic acid, flufenamic acid and sulindac. The compounds can also be administered with corticosteroids or an anti-emetic such as Zofran®.

Compounds of formula (I) seem to be particularly suitable for co-administration with one or more anti-cancer drugs such as cisplatin, dehydroequol, taxol (paclitaxel), gemcitabine, doxorubicin, topotecan and/or camptothecin. This may result in improved effects in the treatment, for example in the form of synergistic effects, in comparison to when only one of the medicaments is employed. Particularly the compounds of the presently claimed invention seem to be chemosensitisers and increase the cytotoxicity of the one or more anticancer drug co-administered therewith. This seems to be the case even though said anticancer drugs work through a variety of different mechanisms, for example cisplatin is thought to work by interacting with nuclear DNA, taxol is thought to work by blocking cells in the G2/M phase of the cell cycle and prevent them forming normal mitotic apparatus, gemcitabine is thought to work by incorporating itself into the DNA of the cell, ultimately preventing mitosis, doxorubicin is though to be a topoisomerase II inhibitor thereby preventing DNA replication and transcription and topotecan is thought to be a topoisomerase I inhibitor.

Interestingly, in some situations this increased cytotoxicity to cancerous cells is not associated with a corresponding increase in toxicity to non-cancerous cells. Whilst this observation has important implications for the treatment of many cancers, it is especially important to the treatment of cancers such as melanoma, which are extremely difficult to treat.

The co-administration may be simultaneous or sequential. Simultaneous administration may be effected by the compounds being in the same unit dose, or in individual and discrete unit doses administered at the same or similar time. Sequential administration may be in any order as required and typically will require an ongoing physiological effect of the first or initial active agent to be current when the second or later active agent is administered, especially where a cumulative or synergistic effect is desired.

The invention also extends to a pack comprising the combination therapy.

The oxazinyl compounds of the invention are also particularly suited as active agents used with implantable medical devices. These implantable medical devices are adapted to be used in various settings including vascular applications and as drug-eluting stents. Stents and catheters in particular are adapted to be implanted into a patient's body lumen, such as a blood vessel e.g. coronary artery, bile ducts, oesophagus, colon, trachea or large bronchi, ureters and urethra. Stents are particularly useful in the treatment of atherosclerotic stenosis and aneurysms.

Stents are typically implanted within a vessel or lumen in a contracted state, and can be expanded when in place in the vessel in order to maintain the patency of the vessel to allow fluid flow through the vessel. Stents have a support structure such as a metallic structure to provide the strength required and are often provided with an exterior surface coating to provide a biocompatible and/or hemocompatible surface. The coating is typically a polymeric material loaded with therapeutically active agents for release at a specific intravascular site for action on the surrounding vessel or downstream thereof.

Drug-eluting stent devices have shown great promise in treating coronary artery disease, specifically in terms of reopening and restoring blood flow in arteries stenosed by atherosclerosis. Restenosis rates after using drug-eluting stents during percutaneous intervention are significantly lower compared to bare metal stenting and balloon angioplasty.

As will be appreciated by those having ordinary skill in the art, the drug-eluting stent used in accordance with the present invention can be virtually of any type. The drug-eluting stent may be formed at least in part of a medical grade metallic material such as stainless steel, platinum, titanium, tantalum, nickel-titanium, cobalt-chromium, and alloys thereof.

The stents may also be made of bioabsorbable material. Typically these stents are fully resorbable structures having metal-like scaffolding, generally use standard balloon deployment, and can be loaded with drug. Examples of the materials with which bioabsorbable stents can be made is polylactic acid (PLA), a biodegradable, thermoplastic, aliphatic polyester (Ormiston et al. 2007) or polylactic-co-glycolic acid (PLGA), a biodegradable biocompatible copolymer. Another example is stents made using magnesium (Erbel et al. 2007).

The active agent can be attached to the implantable medical devices surface by any means that provide a drug-releasing platform. Binding can be achieved covalently, ionically, or through other molecular interactions including hydrogen bonding and van der Waals forces. Coating methods include, but are not limited to precipitation, coacervation, and crystallization. More typically, the active agent is complexed with a suitable biocompatible polymer. The polymer-drug complex is then used to either form a controlled-release medical device, integrated into a preformed medical device or used to coat a medical device as would be well known to a person skilled in the art. The coatings can be applied as a liquid polymer/solvent matrix. The liquid coating can be applied by pad printing, inkjet printing, rolling, painting, spraying, micro-spraying, dipping, wiping, electrostatic deposition, vapour deposition, epitaxial growth, combinations thereof and other methods of achieving controlled drug release with the active agents are contemplated as being part of the present invention.

Examples of suitable polymers for use in coating the implantable medical devices include poly(ethylene-co-vinyl alcohol) (EVAL), poly(N-vinylpyrrolidone) (PVP), ethyl cellulose, cellulose acetate, carboxymethyl cellulose, cellulosics, chitin, chitosan, poly(vinyl alcohol), heparin, dextran, dextrin, dextran sulfate, collagen, gelatin, hyaluronic acid, chondroitan sulfate, glycosaminoglycans, poly[(2-hydroxyethyl)methylmethacrylate], polyurethanes, poly(ether urethanes), poly(ester urethanes), polycarbonate urethanes), thermoplastic polyesters, solvent soluble nylons, poly(acrylamide), poly(acrylic acid), copolymers of acrylic acid and acrylates, poly(methacrylic acid), copolymers of methacrylic acid and methacrylates, and blends thereof.

Persons skilled in the art will appreciate that different polymers are better suited to different solvents in the formation of the medical device coatings. Examples of suitable solvents include acetone, ethyl acetate, chloroform, dichloromethane, DMAC, DMSO, DMF, THF, formamide, N-methyl-2-pyrrolidone (NMP), sulfolane, benzyl alcohol, cyclohexanol, phenol, formic acid, m-cresol, p-cresol, trifluoroacetic acid, glycerol, ethylene glycol, propylene glycol, ethanol, propanols and mixtures thereof. The active agent must also be suitably soluble or dispersible in the polymer/solvent mixture and retain its activity during the coating process.

The polymer is adhered to the stent using conventional metal-polymer adhesion techniques, such as by dipping, spraying, wiping, and brushing, which are known in the art. These processes may be followed by web clearing operations that can include blowing air or spinning and drying operations including evaporation, heating and subjecting the coating to reduced pressure to remove the solvent and set the drug containing polymer. The polymer coating can have a thickness in the range of about 1 micron to about 10 microns or more and more that one coating may be desired including primer coatings and protective layer coatings.

The active agent loading is typically between about 0.1 and about 10 mass % of the total mass of the formulation used to make the drug-polymer layer. The drug can include additional substances capable of exerting a therapeutic or prophylactic effect for a patient or for use in increasing drug delivery, as a preservative, stabiliser or the like.

The oxazinyl compounds of the present invention are particularly suited as the active agent with the implantable medical devices. The active agent produces a therapeutic effect against one or more conditions including inflammation, restenosis including vascular restenosis, atherosclerosis, hyperplasia and other diseases and conditions. The oxazinyl compound may be present either alone or in combination with additional active agents. The additional active agents may be selected from antiplatelets, anticoagulants, antifibrins, anti-inflammatories, antithrombins, immunosuppressives and antiproliferaties amongst others.

Therapeutic drugs suitable for co-application onto the stents include, but are not limited to, antiproliferatives including paclitaxel and rapamyacin, antithrombins, immunosuppressants including sirolimus, antilipid agents, anti-inflammatory agents, antineoplastics, antiplatelets, angiogenic agents, anti-angiogenic agents, vitamins, antimitotics, metalloproteinase inhibitors, NO donors, estradiols, anti-sclerosing agents; and vasoactive agents, endothelial growth factors, estrogen, beta blockers, AZ blockers, hormones, statins, insulin growth factors, antioxidants, membrane stabilizing agents, calcium antagonists, retenoid, bivalirudin, phenoxodiol, etoposide, ticlopidine, dipyridamole and trapidil alone or in combinations with any therapeutic agent mentioned herein. Therapeutic agents also include peptides, lipoproteins, polypeptides, polynucleotides encoding polypeptides, lipids, protein-drugs, protein conjugate drugs, enzymes, oligonucleotides and their derivatives, ribozymes, other genetic material, cells, antisense, oligonucleotides, monoclonal antibodies, platelets, prions, viruses, bacteria, and eukaryotic cells such as endothelial cells, stem cells, ACE inhibitors, monocyte/macrophages or vascular smooth muscle cells to name but a few examples. The therapeutic agent may also be a pro-drug, which metabolizes into the desired drug when administered to a host. In addition, therapeutic agents may be pre-formulated as microcapsules, microspheres, microbubbles, liposomes, niosomes, emulsions, dispersions or the like before they are incorporated into the therapeutic layer. Therapeutic agents may also be radioactive isotopes or agents activated by some other form of energy such as light or ultrasonic energy, or by other circulating molecules that can be systemically administered. Therapeutic agents may perform multiple functions including modulating angiogenesis, restenosis, cell proliferation, thrombosis, platelet aggregation, clotting and vasodilation. Anti-inflammatories include non-steroidal anti-inflammatories (NSAID), such as aryl acetic acid derivatives, e.g., Diclofenac; aryl propionic acid derivatives, e.g., Naproxen; and salicylic acid derivatives, e.g., aspirin and Diflunisal. Anti-inflammatories also include glucocoriticoids (steroids), such as dexamethasone, prednisolone and triamcinolone. Anti-inflammatories may be used in combination with antiproliferatives to mitigate the reaction of the tissue to the antiproliferative.

Some of the agents described herein may be combined with additives which preserve their activity. For example additives including surfactants, antacids, antioxidants, and detergents may be used to minimize denaturation and aggregation of a protein drug. Anionic, cationic or nonionic detergents may be used. Examples of nonionic additives include but are not limited to sugars including sorbitol, sucrose, trehalose; dextrans including dextral', carboxy methyl (CM) dextran, diethylamino ethyl (DEAE) dextran; sugar derivatives including D-glucosaminic acid, and D-glucose diethyl mercaptal; synthetic polyethers including polyethylene glycol (PEO) and polyvinyl pyrrolidone (PVP); carboxylic acids including ID-lactic acid, glycolic acid, and propionic acid; detergents with affinity for hydrophobic interfaces including n-dodecyl-β-D-maltoside, n-octyl-β-D-glucoside, PEO-fatty acid esters (e.g. stearate (myrj 59) or oleate), PEO-sorbitan-fatty acid esters (e.g. Tween 80, PEO-20 sorbitan monooleate), sorbitan-fatty acid esters (e.g. SPAN 60, sorbitan monostearate), PEO-glyceryl-fatty acid esters; glyceryl fatty acid esters (e.g. glyceryl monostearate), PEO-hydrocarbon-ethers (e.g. PEO-10 oleyl ether; triton X-100; and Lubrol. Examples of ionic detergents include but are not limited to fatty acid salts including calcium stearate, magnesium stearate, and zinc stearate; phospholipids including lecithin and phosphatidyl choline; CM-PEG; cholic acid; sodium dodecyl sulfate (SDS); docusate (AOT); and taumocholic acid.

The drug-eluting stents and catheters of the present invention may be utilised in any part of the vasculature including neurological, carotid, coronary, renal, aortic, iliac, femoral or other peripheral vasculature. The stents can deliver the active agents to the site of implantation or downstream of the site.

The drug-eluting stents can have multiple layers created independently and as such individual chemical compositions and pharmacokinetic properties can be imparted to each layer. Each of the layers may include one or more agents in the same or different proportions from layer to layer. Changes in the agent concentration between layers can be used to achieve a desired delivery profile. For example, a decreasing release of drug for about 24 hours can be achieved. In another example, an initial burst followed by a constant release for about one week can be achieved. Other examples can deliver an agent over a sustained period of time, such as several days to several months. Substantially constant release rates over time period from a few hours to months can be achieved. The layers may be solid, porous, or filled with other drugs or excipients and the like.

Whilst not wishing to be bound by theory the compounds of the present invention are thought to regulate a wide variety of signal transduction processes within animal cells and that these signal transduction processes are involved in a wide range of functions that are vital to the survival and function of all animal cells. Therefore, these compounds have broad-ranging and important health benefits in animals including humans, and in particular have the potential to prevent and treat important and common human diseases, disorders and functions, which represent a substantial unexpected benefit.

The invention is further illustrated by the following non-limiting Examples and accompanying drawings.

EXAMPLES 1.0. Synthesis

The numbering system as shown below for the 2,3,4,8-tetrahydrochromeno[6,7-e][1,3]oxazine base structure is used throughout this specification for consistency.

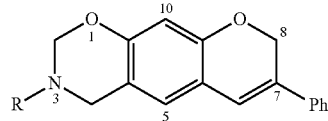

Example 1

4-(3-Benzyl-2,3,4,8-tetrahydrochromeno[6,7-e][1,3]oxazin-7-yl)phenol

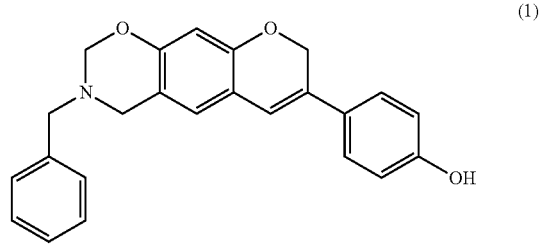 [SMILES: Oc1ccc(C2=Cc3cc4c(cc3OC2)OCN(Cc2ccccc2)C4)cc1]

(1)

4',7-Dihydroxyisoflav-3-ene (0.47 g, 1.97 mmol) was dissolved in ethanol (ca. 40 mL) and heated to 80-90° C. A solution of benzylamine (0.44 mL, 3.5 mmol) and 37% formaldehyde (0.35 mL, 12.7 mmol) in ethanol (ca. 20 mL) was added to the dehydroequol solution. The reaction mixture was refluxed for approximately 7 hours and after cooling to room temperature the volume was concentrated in vacuo. The mixture was left in the fridge to crystallise. The yellow solid was collected under suction and the filtrate evaporated to dryness to obtain a second crop of the title compound, (combined yield 0.17 g, 23%).

$^1$H NMR (400 MHz, ($d_6$-DMSO) δ 73 (7H, m), 6.75 (2H, d, 7 Hz), 6.71 (1H, s), 6.70 (1H, s) 6.22 (1H, s), 5.0 (2H, s), 4.80 (2H, s) 3.80 (2H, s), 3.77 (2H, s).

Example 2

4-(3-(1-Phenylethyl)-2,3,4,8-tetrahydrochromeno[6,7-e][1,3]oxazin-7-yl)phenol

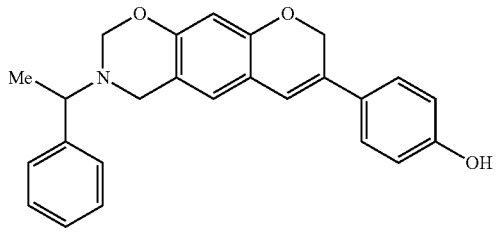

(2)

4',7-Dihydroxyisoflav-3-ene (0.45 g, 1.87 mmol) was dissolved in ethanol (ca 40 mL) and heated to 80-90° C. A solution of methylbenzylamine (0.44 mL, 4.03 mmol) and 37% formaldehyde (0.35 mL, 123 mmol) in ethanol (ca. 20 mL) was added to the dehydroequol solution. The reaction mixture was refluxed for approximately 7 hours and after cooling to room temperature the volume was concentrated in vacuo. The mixture was left in the fridge to crystallise. The yellow solid was collected under suction and the filtrate evaporated to dryness to obtain a second crop of the title compound, (combined yield 0.17 g, 23%).

$^1$H NMR (400 MHz, $d_6$-DMSO) δ 7.4 (7H, m), 6.75 (2H, d, 7 Hz), 6.65 (1H, s), 6.63 (1H, s) 6.22 (1H, s), 5.0 (2H, s), 4.99 (1H, d, 6 Hz), 4.81 (1H, d, 6 Hz), 4.01 (1H, d, 8 Hz), 3.95 (1H, q, 7 Hz), 3.55 (1H, d, 8 Hz), 1.44 (3H, d, 7 Hz).

Example 3

4-(3-Propyl-2,3,4,8-tetrahydrochromeno[6,7-e][1,3]oxazin-7-yl)phenol (3)

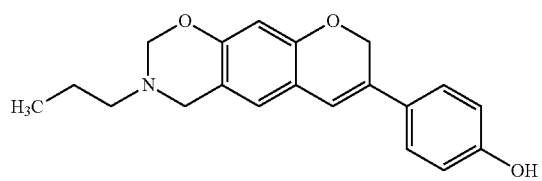

4',7-Dihydroxyisoflav-3-ene (503 mg, 2.09 mmol) was dissolved in ethanol (20 ml). Propylamine (0.25 ml, 3.04 mmol) was added followed by formaldehyde solution (2 ml, 0.03 mol, 37% wt.). The reaction was stirred at room temperature for 1 day. The white precipitate was collected to afford the title compound (362 mg, 53%).

$^1$H NMR (400 MHz, $d_6$-DMSO) δ 0.89 (3H, t, J=7.2 Hz, $CH_3$), 1.55 (2H, m, CH2$CH_3$), 2.66 (2H, t, J=7.2 Hz, $NCH_2CH_2$), 3.88 (2H, s, $NCH_2$Ar), 4.80 (2H, s, $NCH_2$O), 5.04 (2H, s, H8), 6.16 (1H, s, H10), 6.71 (1H, bs, H6), 6.72 (1H, s, H5), 6.85 (2H, d, J=8.8 Hz, H3', H5'), 7.35 (2H, d, J=8.8 Hz, H2', H6').

Example 4

4-(3-Methyl-2,3,4,8-tetrahydrochromeno[6,7-e][1,3]oxazin-7-yl)phenol

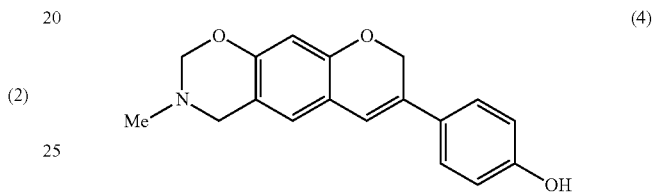

(4)

4',7-Dihydroxyisoflav-3-ene (507 mg, 2.11 mmol) was dissolved in ethanol (20 ml). Methylamine solution (0.6 ml, 4.82 mmol, 33% wt. in ethanol) was added followed by formaldehyde solution (2 ml, 0.03 mol, 37% wt.). The reaction was stirred at room temperature for 1 day. The white precipitate was collected to afford the title compound (490 mg, 79%).

$^1$H NMR (400 MHz, $d_6$-DMSO) δ 2.44 (3H, s, $CH_3$), 3.78 (2H, s, $NCH_2$Ar), 4.70 (2H, s, $NCH_2$O), 4.99 (2H, s, H8), 6.18 (1H, s, H10), 6.74 (4H, m, H4, H5, H3', H5'), 7.31 (2H, d, J=8.8 Hz, H2', H6'), 9.58 (1H, bs, OH).

Example 5

7-(3,4-Dimethoxyphenyl)-3-propyl-2,3,4,8-tetrahydrochromeno[6,7-e][1,3]oxazine (5)

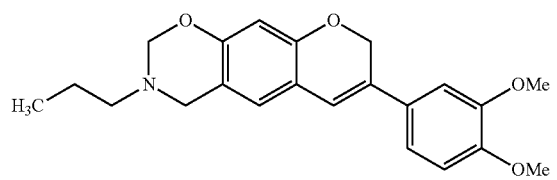

7-Hydroxy-3',4'-dimethoxyisoflav-3-ene (99 mg, 3.48 mmol) was dissolved in ethanol (10 ml). Propylamine (0.1 ml, 4.25 mmol) was added followed by formaldehyde solution (0.4 ml, 5.37 mmol, 37% wt.). The reaction was stirred at room temperature for 8 days. The precipitate was collected to afford the title compound (6 mg, 1%).

$^1$H NMR (400 MHz, $d_6$-acetone) δ 0.89 (3H, t, J=7.4 Hz, $CH_3$), 1.53 (2H, m, $CH_2CH_3$), 2.66 (2H, t, J=7.4 Hz, $NCH_2CH_2$), 3.81 (3H, s, $OCH_3$), 3.85 (3H, s, $OCH_3$), 3.89 (2H, s, $NCH_2$Ar), 4.81 (2H, s, $NCH_2$O), 5.06 (2H, s, H8), 6.17

(1H, s, H10), 6.74 (1H, s, H6), 6.79 (1H, s, H5), 6.95 (1H, d, J=8.4 Hz, H5'), 7.00 (1H, dd, J=2.4 Hz, 8.4 Hz, H6'), 7.13 (1H, d, J=2.4 Hz, H2')

Example 6

4-(3-(4-Methoxybenzyl)-2,3,4,8-tetrahydrochromeno[6,7-e][1,3]oxazin-7-yl)phenol

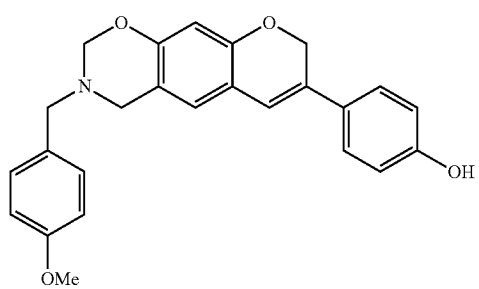

(6)

4',7-Dihydroxyisoflav-3-ene (501 mg, 2.09 mmol) was dissolved in ethanol (15 ml). 4-Methoxybenzylamine (0.35 ml, 2.68 mmol) was added followed by formaldehyde solution (2 ml, 0.03 mol, 37% wt.). The reaction was stirred at room temperature for 1 day. The white precipitate was collected to afford the title compound (555 mg, 66%).

$^1$H-NMR (400 MHz, $d_6$-acetone) δ 2.78 (3H, s, OCH$_3$), 3.82 (2H, s, NCH$_2$Ar), 3.84 (2H, s, NCH$_2$Ar), 4.83 (2H, s, NCH$_2$O), 5.06 s, H8), 6.22 (1H, s, H10), 6.71 (2H, bs, H4, H5), 6.85 (2H, d, J=8.8 Hz, H3', H5'), 6.89 (2H, d, J=8.8 Hz, ArH), 7.25 (2H, d, J=8.8 Hz, ArH), 7.35 (2H, d, J=8.8 Hz, H2', H6'), 8.59 (1H, bs, OH)

Example 7

4-(3-Phenyl-2,3,4,8-tetrahydrochromeno[6,7-e][1,3]oxazin-7-yl)phenol

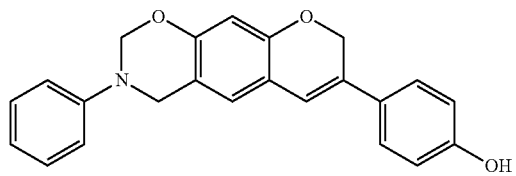

(7)

4',7-Dihydroxyisoflav-3-ene (501 mg, 2.09 mmol) was dissolved in ethanol (15 ml). Aniline (0.25 ml, 2.74 mmol) was added followed by formaldehyde solution (2 ml, 0.03 mol, 37% wt.). The reaction was stirred at room temperature for 3 days. The white precipitate was collected to afford the title compound (53 mg, 7%).

$^1$H NMR (400 MHz, $d_6$-acetone) δ 4.60 (2H, s, NCH$_2$Ar), 5.04 (2H, s, H8), 5.40 (2H, s, NCH$_2$O), 6.19 (1H, s, H10), 6.72 (1H, s, H6), 6.85 (3H, m, H5, H3', H5'), 7.14 (2H, m, ArH), 7.22 (3H, m, ArH), 7.35 (2H, d, J=8.8 Hz, H2', H6'), 8.49 (1H, s, OH).

Example 8

4,4'-(Chromeno[6,7-e][1,3]oxazine-3,7(2H,4H,8H)-diyl)diphenol

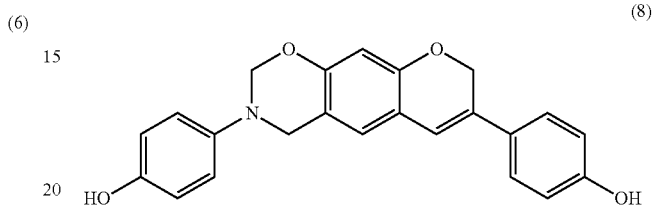

(8)

4',7-Dihydroxyisoflav-3-ene (509 mg, 2.12 mmol) and 4-aminophenol (307 mg, 2.81 mmol) were dissolved in ethanol (15 ml). Formaldehyde solution (2 ml, 0.03 mol, 37% wt.) was added and the reaction stirred at room temperature for 3 days. The resulting precipitate was collected to afford the title compound (178 mg, 79%).

$^1$H NMR (400 MHz, $d_6$-acetone) δ 4.46 (2H, s, NCH$_2$Ar), 5.03 (2H, s, H8), 527 (2H, s, NCH$_2$O), 6.18 (1H, s, H10), 6.70 (3H, m, H4, ArH), 6.80 (1H, s, H5), 6.85 (2H, d, J=8.8 Hz, H3', H5'), 6.99 (2H, d, J=8.8 Hz, ArH), 7.35 (2H, d, J=8.8 Hz, H2', H6') 7.91 (1H, bs, OH), 8.46 (1H, bs, OH).

Example 9

7-(3,4-Dimethoxyphenyl)-3-(4-methoxybenzyl)-2,3,4,8-tetrahydro-chromeno[6,7-e][1,3]oxazine

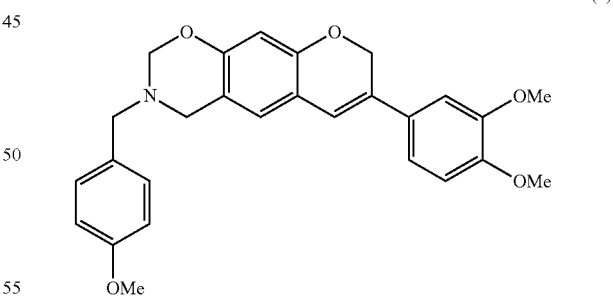

(9)

7-Hydroxy-3',4'-dimethoxyisoflav-3-ene (152 mg, 0.53 mmol) was dissolved in ethanol (2 ml). 4-Methoxybenzylamine (0.1 ml, 0.77 mmol) was added followed by formaldehyde solution (0.6 ml, 8.06 mmol, 37% wt.). The reaction was stirred at room temperature for 2 days. The resulting precipitate was collected to afford the title compound (102 mg, 43%).

$^1$H NMR (400 MHz, 4-acetone) δ 3.80 (15H, m, NCH$_2$Ar, NCH$_2$Ar, OCH$_3$, OCH$_3$, OCH$_3$), 4.83 (2H, s, NCH$_2$O), 5.08 (2H, s, H8), 6.23 (1H, s, H10), 6.71 (1H, s, H6), 6.79 (1H, s, ArH), 6.89 (2H, d, J=8.4 Hz, ArH), 6.94 (1H, d, J=8.4 Hz, ArH), 7.00 (1H, d, J=8.4 Hz, ArH), 7.14 (1H, s, ArH), 7.25 (2H, d, J=8.4 Hz, ArH).

Example 10

3-(3-Benzyl-2,3,4,8-tetrahydrochromeno[6,7-e][1,3]oxazin-7-yl)phenol

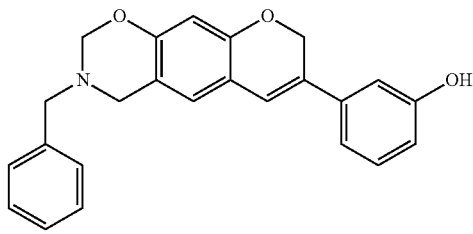

(10)

3',7-Dihydroxyisoflav-3-ene (100 mg, 0.42 mmol) was dissolved in ethanol (4 ml). Benzylamine (0.14 ml, 1.28 mmol) was added followed by formaldehyde solution (0.42 ml, 5.59 mmol, 37% wt.). The reaction was stirred at room temperature for 1 day. Reaction mixture was poured into water (50 ml) then extracted with ethyl acetate (3×30 ml) and the combined organic layers reduced. The solid was flash chromatographed using 100% dichloromethane. Fractions 6-12 were combined and reduced to afford the title compound.

$^1$H NMR (400 MHz, d$_6$-acetone) δ 3.85 (2H, s, NCH$_2$Ar), 3.89 (2H, s, NCH$_2$Ph), 4.85 (2H, s, NCH$_2$O), 5.06 (2H, s, H8), 6.25 (1H, s, H10), 6.72 (1H, s, ArH), 6.80 (1H, m, H6), 6.95 (2H, m, ArH), 7.19 (1H, t, J=8.0 Hz, H5'), 7.34 (5H, m, ArH).

Example 11

3-(3-Phenyl-2,3,4,8-tetrahydrochromeno[6,7-e][1,3]oxazin-7-yl)phenol

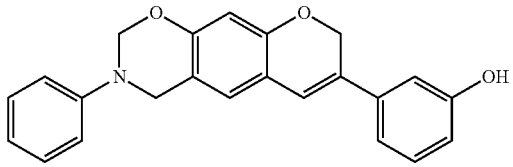

(11)

3',7-Dihydroxyisoflav-3-ene (175 mg, 0.73 mmol) was dissolved in ethanol (1 ml). Aniline (0.08 ml, 0.88 mmol) was added followed by formaldehyde solution (0.6 ml, 8.06 mmol, 37% wt.). The reaction was stirred at room temperature for 3 days. The resulting precipitate was collected to afford the title compound (160 mg, 61%).

$^1$H NMR (400 MHz, d$_6$-acetone) δ 4.61 (2H, s, NCH$_2$Ar), 5.04 (2H, s, H8), 5.42 (2H, s, NCH$_2$O), 6.20 (1H, s, H10), 6.78 (1H, m, ArH), 6.82 (1H, s, H6), 6.89 (1H, s, H5), 6.95 (1H, m, Aril), 7.05 (2H, m, ArH), 7.18 (5H, m, ArH).

Example 12

7-(3,4-Dimethoxyphenyl)-3-phenyl-2,3,4,8-tetrahydrochromeno[6,7-e][1,3]oxazine

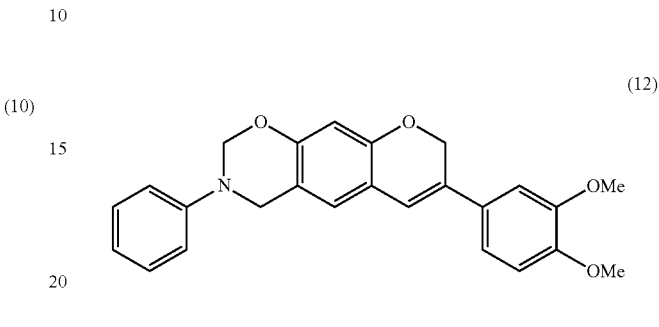

(12)

7-Hydroxy-3',4'-dimethoxyisoflav-3-ene (148 mg, 0.52 mmol) was dissolved in ethanol (2 ml). Aniline (0.6 ml, 0.66 mmol) was added followed by formaldehyde solution (0.6 ml, 8.06 mmol, 37% wt.). The reaction was stirred at room temperature for 3 days. The precipitate was collected to afford the title compound (11 mg, 5%).

$^1$H NMR (400 MHz, d$_6$-acetone) δ 3.81 (3H, s, OCH$_3$), 3.85 (3H, s, OCH$_3$), 4.61 (2H, s, NCH$_2$Ar), 5.06 (2H, s, H8), 5.41 (2H, s, NCH$_2$O), 6.19 (1H, s, H10), 6.80 (1H, s, H6), 6.86 (1H, s, ArH), 6.94 (1H, d, J=8.0 Hz., ArH), 7.00 (1H, dd, J=22 Hz, 8.2 Hz, H6'), 7.14 (3H, m, ArH), 7.21 (3H, m, ArH).

Example 13

3-Benzyl-7-(3,4-dimethoxyphenyl)-10-methyl-2,3,4,8-tetrahydro-chromeno[6,7-e][1,3]oxazine

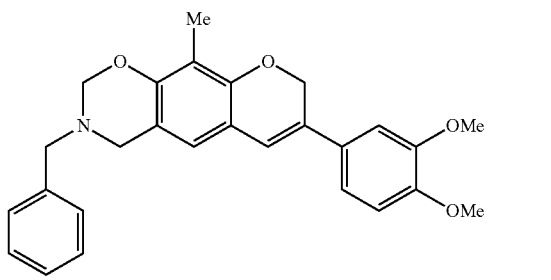

(13)

7-Hydroxy-3',4'-dimethoxy-8-methylisoflav-3-ene (155 mg, 0.52 mmol) was dissolved in ethanol (2.5 ml). Benzylamine (0.07 ml, 023 mmol) was added followed by formaldehyde solution (0.6 ml, 8.06 mmol, 37% wt.). The reaction was stirred at room temperature for 2 days. The precipitate was collected to afford the title compound (33 mg, 15%).

$^1$H NMR (400 MHz, d$_6$-acetone) δ 2.02 (3H, s, CH$_3$Ar), 3.82 (3H, s, OCH$_3$), 3.86 (5H, s, OCH$_3$, CH$_2$Ph), 3.89 (2H, s, NCH$_2$Ar), 4.91 (2H, s, NCH$_2$O), 5.11 (2H, s, H8), 6.58 (1H, s, H6), 6.79 (1H, s, ArH), 6.95 (1H, d, J=8.4 Hz, ArH), 7.01 (1H, dd, J=2.0 Hz, 8.4 Hz, H6), 7.15 (1H, d, J=2.0 Hz, ArH), 7.30 (5H, m, ArH).

Example 14

7-(3,4-Dimethoxyphenyl)-10-methyl-3-propyl-2,3,4,8-tetrahydro-chromeno[6,7-e][1,3]oxazine

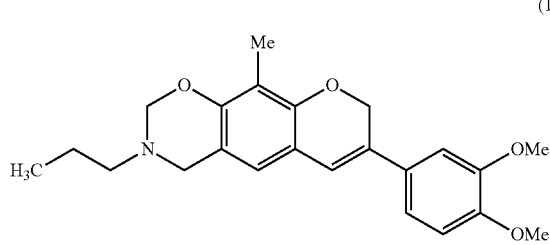

(14)

7-Hydroxy-3',4'-dimethoxy-8-methylisoflav-3-ene (159 mg, 0.53 mmol) was dissolved in ethanol (2.5 ml). Propylamine (0.05 ml, 0.61 mmol) was added followed by formaldehyde solution (0.6 ml, 8.06 mmol, 37% wt.). The reaction was stirred at room temperature for 2 days. The precipitate was collected to afford the title compound (7 mg, 3%).

$^1$H NMR (400 MHz, $d_6$-acetone) δ 0.90 (3H, t, J=7.4 Hz, CH$_3$), 1.54 (2H, m, CH$_2$), 1.98 (3H, s, CH$_3$Ar), 2.66 (2H, t, J=7.4 Hz, NCH$_2$), 3.82 (3H, s, OCH$_3$), 3.86 (3H, s, OCH$_3$), 3.89 (2H, s, NCH$_2$Ar), 4.86 (2H, s, NCH$_2$O), 5.09 (2H, s, H8), 6.61 (1H, s, H6), 6.78 (1H, s, 1-H5), 6.96 (1H, s, ArH), 7.00 (1H, dd, J=2.4 Hz, 8.4 Hz, H6'), 7.14 (1H, d, J=1.6 Hz, ArH).

Example 15

4-(3-(4-Chlorobenzyl)-2,3,4,8-tetrahydrochromeno[6,7-e][1,3]oxazin-7-yl)phenol

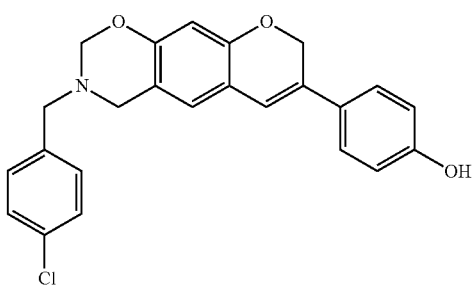

(15)

4',7-Dihydroxyisoflav-3-ene (506 mg, 2.11 mmol) was dissolved in ethanol (8 ml). 4-Chlorobenzylamine (0.33 ml, 2.70 mmol) was added followed by formaldehyde solution (2 ml, 0.03 mol, 37% wt.). The reaction was stirred at room temperature for 4 days. The white precipitate was collected to afford the title compound (748 mg, 88%).

$^1$H NMR (400 MHz, $d_6$-acetone) δ 3.86 (2H, s, CH$_2$Ph), 3.90 (2H, s, NCH$_2$Ar), 4.86 (2H, s, NCH$_2$O), 5.06 (2H, s, H8), 6.23 (1H, s, H10), 6.72 (2H, bs, H4, H5), 6.85 (2H, d, J=8.8 Hz, H3', H5'), 7.37 (m, 6H, H2', H6', H2", H3", H5", H6").

Example 16

4-(3-(3-Methoxypropyl)-2,3,4,8-tetrahydrochromeno[6,7-e][1,3]oxazin-7-yl)phenol

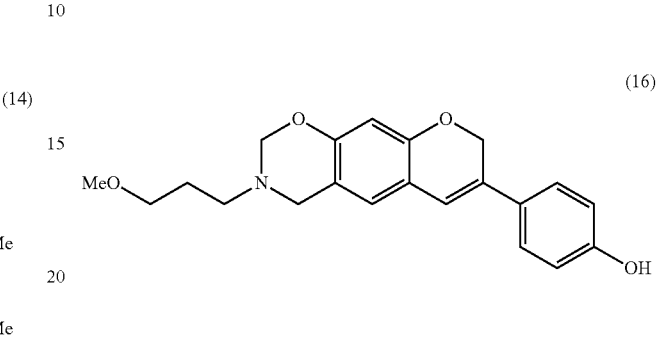

(16)

4',7-Dihydroxyisoflav-3-ene (509 mg, 2.12 mmol) was dissolved in ethanol (8 ml). 3-methoxypropylamine (0.28 ml, 2.74 mmol) was added followed by formaldehyde solution (2 ml, 0.03 mol, 37% wt.). The reaction was stirred at room temperature for 4 days. The precipitate was collected to afford the title compound (657 mg, 88%).

$^1$H NMR (400 MHz $d_6$-acetone) δ 1.76 (2H, m, CH$_2$), 2.77 (2H, t, J=7.41 Hz, NCH$_2$), 3.24 (3H, s, OCH$_3$), 3.39 (2H, t, J=6.4 Hz, OCH$_2$), 3.89 (2H, s, NCH$_2$Ar), 4.81 (2H, s, NCH$_2$O), 5.04 (2H, s, H8), 6.17 (1H, s, H10), 6.72 (1H, s, H6), 6.74 (1H, s, H5), 6.86 (2H, d, J=8.8 Hz, H3', H5'), 7.35 (2H, d, J=8.8 Hz, H2', H6').

Example 17

3-(3-(3-Methoxypropyl)-2,3,4,8-tetrahydrochromeno[6,7-e][1,3]oxazin-7-yl)phenol

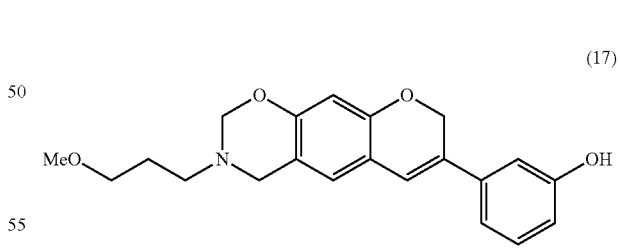

(17)

3',7-Dihydroxyisoflav-3-ene (198 mg, 0.82 mmol) was dissolved in ethanol (3 ml). 3-methoxypropylamine (0.11 ml, 1.08 mmol) was added followed by formaldehyde solution (0.6 ml, 8.06 mmol, 37% wt.). The reaction was stirred at room temperature for 4 days. The resulting precipitate was collected to afford the title compound (69 mg, 24%).

$^1$H NMR (400 MHz, $d_6$-acetone) δ 1.76 (2H, m, CH$_2$), 2.77 (2H, t, J=7.6 Hz, NCH$_2$), 3.24 (3H, s, OCH$_3$), 3.39 (2H, t, J=6.4 Hz, OCH$_2$), 3.91 (2H, s, NCH$_2$Ar), 4.82 (2H, s, NCH₂O), 5.05 (2H, s, H8), 6.18 (1H, s, H10), 6.79 (3H, m, ArH), 6.94 (2H, m, ArH), 7.18 (1H, t, J=8 Hz, ArH).

Example 18

4-(3-p-Tolyl-2,3,4,8-tetrahydrochromeno[6,7-e][1,3]oxazin-7-yl)phenol

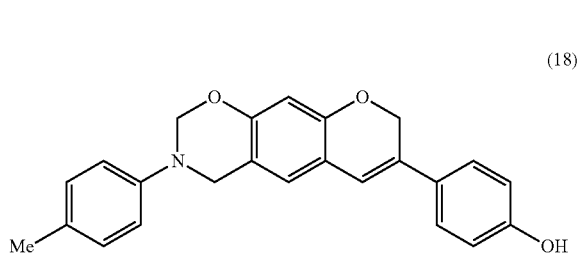 [SMILES: Oc1ccc(C2=Cc3cc4c(cc3OC2)OCN(c2ccc(O)cc2)C4)cc1]

(18)

4',7-Dihydroxyisoflav-3-ene (499 mg, 2.08 mmol) and p-toluidine (290 mg, 2.71 mmol) were dissolved in ethanol (8 ml). Formaldehyde solution (2 ml, 0.03 mol, 37% wt) was added and the reaction stirred at room temperature for 2 days. The resulting precipitate was collected to afford the title compound (167 mg, 22%).

$^1$H NMR (400 MHz, d₆-DMSO) δ 2.16 (3H, s, CH₃), 4.50 (2H, s, NCH₂Ar), 4.98 (2H, s, H8), 5.36 (2H, s, NCH₂O), 6.15 (1H, s, H10), 6.72 (1H, s, ArH), 6.75 (2H, d, J=8.8 Hz, ArH), 6.83 (1H, s, ArH), 7.00 (4H, d, J=3.6 Hz; ArH), 7.31 (2H, d, J=8.8 Hz, ArH).

Example 19

7-(3,4-Dimethoxyphenyl)-10-methyl-3-p-tolyl-2,3,4,8-tetrahydrochromeno[6,7-e][1,3]oxazine

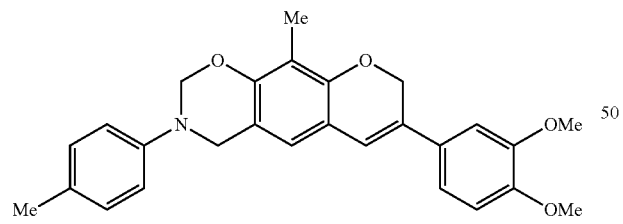

(19)

7-Hydroxy-3',4'-dimethoxy-8-methylisoflav-3-ene (173 mg, 0.58 mmol) and p-toluidine (167 mg, 1.56 mmol) were dissolved in ethanol (2 ml). Formaldehyde solution (0.6 ml, 8.06 mmol, 37% wt.) was added and the reaction stirred at mom temperature for 2 days. The resulting precipitate was collected to afford the title compound (36 mg, 14%).

$^1$H NMR (400 MHz, d₆-DMSO) δ 1.90 (3H, s, CH₃Ar), 2.16 (3H, s, CH₃ArN), 3.74 (3H, s, OCH₃), 3.79 (3H, s, OCH₃), 4.50 (2H, s, NCH₂Ar), 5.04 (2H, s, H8), 5.41 (2H, s, NCH₂O), 6.74 (1H, s, H6), 6.84 (2H, m, ArH), 6.92 (2H, d, J=8.8 Hz, ArH), 6.97 (1H, d, J=2 Hz, ArH), 7.00 (2H, d, J=2.4 Hz, ArH), 7.10 (1H, d, J=2 Hz, ArH).

Example 20

3-(3-p-Tolyl-2,3,4,8-tetrahydrochromeno[6,7-e][1,3]oxazin-7-yl)phenol

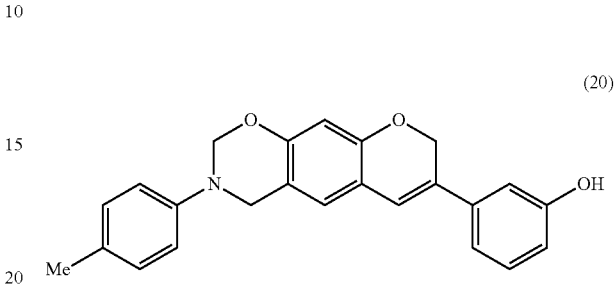

(20)

3',7-Dihydroxyisoflav-3-ene (196 mg, 0.82 mmol) and p-toluidine (130 mg, 1.21 mmol) were dissolved in ethanol (1 ml). Formaldehyde solution (0.6 ml, 8.06 mmol, 37% wt.) was added and the reaction stirred at room temperature for 2 days. The resulting precipitate was collected to afford the title compound (99 mg, 30%).

$^1$H NMR (400 MHz, d₆-DMSO) δ 2.16 (3H, s; CH₃), 4.51 (2H, s, NCH₂Ar), 4.99 (2H, s, H8), 5.37 (2H, s, NCH₂O), 6.17 (1H, s, H10), 6.69 (1H, dd, J=1.4 Hz, 8.2 Hz, H6'), 6.83 (2H, bs, H4, ArH), 6.90 (1H, s, ArH), 6.99 (5H, m, ArH), 7.16 (1H, t, J=8 Hz, H5').

Example 21

4-(7-(3-Hydroxyphenyl)chromeno[6,7-e][1,3]oxazin-3(2H,4H,8H)-yl)benzonitrile

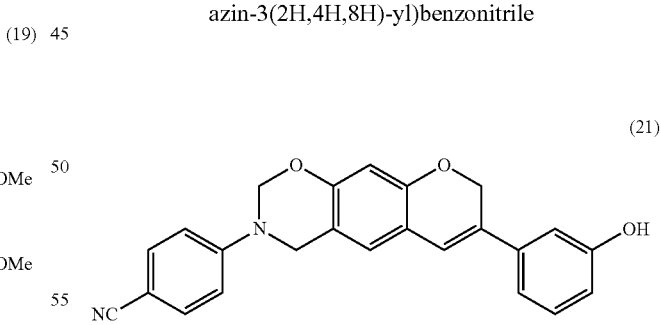

(21)

3',7-Dihydroxyisoflav-3-ene (196 mg, 0.82 mmol) and 4-aminobenzonitrile (120 mg, 1.02 mmol) were dissolved in ethanol (1 ml). Formaldehyde solution (0.6 ml, 8.06 mmol, 37% wt.) was added and the reaction stirred at room temperature for 2 days. The resulting precipitate was collected to afford the title compound (23 mg, 7%).

$^1$H NMR (400 MHz, d₆-DMSO) δ 4.67 (2H, s, NCH₂Ar), 5.00 (2H, s, H8), 5.51 (2H, s, NCH₂O), 6.24 (1H, s, H10), 6.70 (1H, dd, J=2.0 Hz, 8.4 Hz, ArH), 6.84 (1H, m, ArH), 6.85

(1H, bs, H6), 6.91 (1H, d, J=7.6 Hz, ArH), 7.16 (1H, t, J=8 Hz, H5'), 7.25 (2H, d, J=8.8 Hz, ArH), 7.65 (2H, d, J=92 Hz, ArH), 9.47 (1H, bs, OH).

Example 22

4-(3-m-Tolyl-2,3,4,8-tetrahydrochromeno[6,7-e][1,3]oxazin-7-yl)phenol

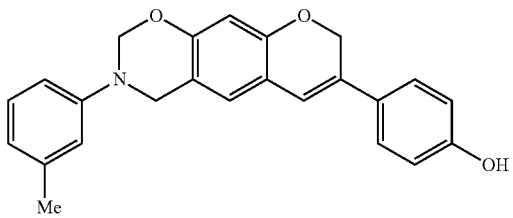

(22)

4',7-Dihydroxyisoflav-3-ene (522 mg, 2.17 mmol) was dissolved in ethanol (8 ml). m-Toluidine (0.3 ml, 2.77 mmol) and formaldehyde solution (2 ml, 0.03 mol, 37% wt.) were added and the reaction stirred at room temperature for 3 days. The resulting precipitate was collected to afford the title compound (386 mg, 48%).

$^1$H NMR (400 MHz, $d_6$-DMSO) δ 2.22 (3H, s, CH$_3$), 4.54 (2H, s, NCH$_2$Ar), 4.98 (2H, s, H8), 5.38 (2H, s, NCH$_2$O), 6.17 (1H, s, H10), 6.65 (1H, d, J=7.6 Hz, ArH), 6.73 (1H, bs, H6), 6.75 (2H, d, J=8.8 Hz, H3', H5'), 6.85 (1H, s, ArH), 6.88 (1H, dd, J=2.0 Hz, 8.0 Hz, ArH), 6.93 (1H, bs, ArH), 7.08 (1H, t, J=7.6 Hz, H5"), 7.31 (2H, d, J=8.8 Hz, H2', H6'), 9.60 (1H, bs, OH).

Example 23

4-(3-(3-Nitrophenyl)-2,3,4,8-tetrahydrochromeno[6,7-e][1,3]oxazin-7-yl)phenol

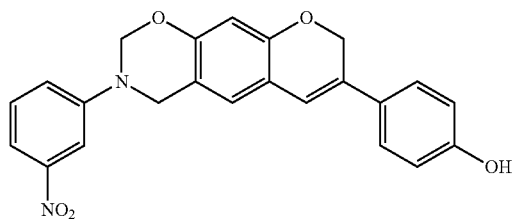

(23)

4',7-Dihydroxyisoflav-3-ene (527 mg, 2.19 mmol) and 3-nitroaniline (333 mg, 2.41 mmol) were dissolved in ethanol (8 ml). Formaldehyde solution (2 ml, 0.03 mol, 37% wt) was added and the reaction stirred at room temperature for 3 days. The resulting precipitate was collected to afford the title compound (35 mg, 4%).

$^1$H NMR (400 MHz, $d_6$-DMSO) δ 4.68 (2H, s, NCH$_2$Ar), 4.99 (2H, s. H8), 5.51 (2H; s, NCH$_2$O), 6.22 (1H, s, H10), 6.75 (3H, m, H4, H3', H5'), 6.90 (1H, s, H5), 7.32 (2H, d, J=8.8 Hz, H2', H6'), 7.51 (1H, t, J=8.0 Hz, H5"), 7.60 (1H, dd, J=2.0 Hz, 8.0 Hz, ArH), 7.67 (1H, dd, J=1.4 Hz, 7.8 Hz, ArH), 7.87 (1H, t, J=2.2 Hz, ArH), 9.61 (1H, bs, OH).

Example 24

4-(3-(4-Chlorobenzyl)-6-(4-methoxyphenyl)-2,3,4,8-tetrahydro-chromeno[6,7-e][1,3]oxazin-7-yl)phenol

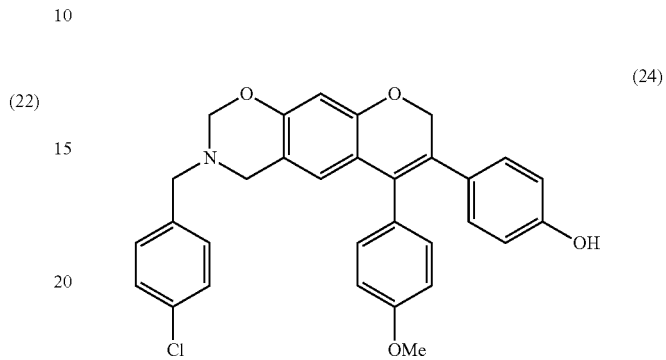

(24)

4',7-Dihydroxy-4-(4-methoxyphenyl)isoflav-3-ene (205 mg, 0.59 mmol) was dissolved in ethanol (1 ml). 4-Chlorobenzylamine (0.09 ml, 0.74 mmol) was added followed by formaldehyde solution (0.6 ml, 8.06 mmol, 37% wt.). The reaction stirred at room temperature for 3 days. The resulting precipitate was collected to afford the title compound (90 mg, 30%).

$^1$H NMR (400 MHz, $d_6$-benzene) δ 3.29 (3H, s, OCH$_3$), 3.47 (2H, s, CH$_2$Ph), 3.62 (2H, s, NCH$_2$Ar), 4.56 (2H, s, NCH$_2$O), 5.06 (2H, s, H8), 6.37 (2H, d, J=8.4 Hz, ArH), 6.72 (1H, s, H10), 6.77 (2H, d, J=8.8 Hz, ArH), 6.85 (2H, d, J=8.4 Hz, ArH), 6.96 (2H, d, J=8.8 Hz, ArH), 7.02 (1H, s, H5), 7.15 (4H, dd, J=2.2 Hz, 8.6 Hz, ArH).

Example 25

4-(10-Bromo-3-propyl-2,3,4,8-tetrahydrochromeno[6,7-e][1,3]oxazin-7-yl)phenol

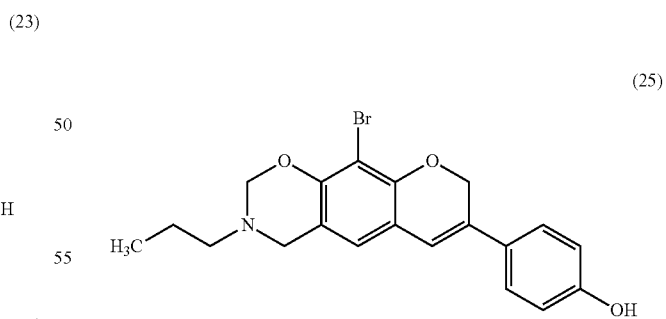

(25)

8-Bromo-4',7-dihydroxyisoflav-3-ene (198 mg, 0.62 mmol) was dissolved in EtOH ml). Propylamine (0.1 ml, 1.22 mmol) and formaldehyde solution (0.3 ml, 4.03 mmol, 37% wt.) were added and the reaction stirred at RT for 24 h. The precipitate was collected to afford the title compound.

$^1$H NMR (400 MHz, $d_6$-DMSO) δ 0.84 (3H, t, J=7.3 Hz, CH$_3$), 1.48 (2H, m, CH$_2$CH$_3$), 2.57 (2H, t, J=7.3 Hz, NCH$_2$CH$_2$), 3.88 (2H, s, NCH$_2$Ar), 4.92 (2H, s, NCH$_2$O), 5.13 (2H, s, H8), 6.74 (1H, s, H6), 6.77 (2H, d, J=8.8 Hz, H3', H5'), 6.78 (1H, s, H5), 7.34 (2H, d, J=8.8 Hz, H2', H6), 9.62 (1H, bs, OH).

Example 26

3,4'-(10-Methyl-chromeno[6,7-e][1,3]oxazine-3,7 (2H,4H,8H)-diyl)diphenol

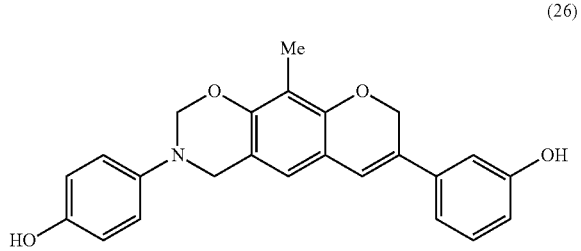 [SMILES: Cc1c2c(cc3c1OCN(c1ccc(O)cc1)C3)C=C(c1cccc(O)c1)CO2]

(26)

3',7-Dihydroxy-8-methylisoflav-3-ene (204 mg, 0.802 mmol) and 4-aminophenol (103 mg, 0.944 mmol) were dissolved in EtOH (1 ml), and formaldehyde solution (0.3 ml, 4.03 mmol, 37% wt.) was added. The reaction was stirred at RT for 3 days, after which no precipitation occurred. The reaction mixture was poured into rapidly stirring distilled water (10 ml), and the resultant precipitate was collected to afford the title compound (143 mg).

$^1$H NMR (400 MHz, $d_6$-DMSO) δ 1.91 (3H, s, CH$_3$), 4.41 (2H, s, NCH$_2$Ar), 5.02 (2H, s, H8), 5.31 (2H, s, NCH$_2$O), 6.53-7.19 (10H, m, Ar, H5, H6), 8.93 (1H, bs, OH), 9.45 (1H, bs, OH).

Example 27

4-(8-Ethyl-3-propyl-2,3,4,8-tetrahydrochromeno[6,7-e][1,3]oxazin-7-yl)phenol

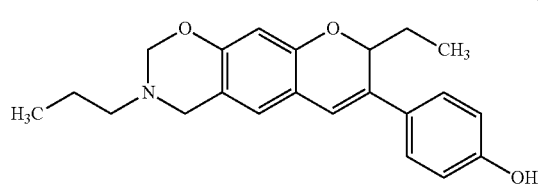

(27)

4',7-Dihydroxy-2-ethylisoflav-3-ene (390 mg, 1.45 mmol) was dissolved in ethanol (20 ml). Propylamine (0.16 ml, 1.95 mmol) was added followed by formaldehyde solution (4 ml, 0.054 mol, 37% wt.). The reaction mixture was stirred at room temperature for 16 hours. The yellow precipitate was collected under suction to afford the title compound (217 mg, 43%).

$^1$H NMR (400 MHz, $d_6$-DMSO) δ 9.56 (1H, br s, OH), 7.35 (2H, d, J=8.7 Hz, H-2',6'), 6.76-6.73 (3H, m, H-3',5', H5), 6.67 (1H, s, H6), 6.18 (1H, s, H10), 5.15 (1H, dd, J=3.0 Hz, 9.5 Hz, H8), 4.81-4.76 (2H, m, NCH$_2$O), 3.31 (2H, s, NCH$_2$Ar), 1.65-1.38 (6H, m, CH$_2$CH$_2$CH$_3$, CH$_2$CH$_3$), 0.91 (3H, t, J=7.3 Hz, CH$_2$CH$_3$), 0.84 (3H, t, J=7.3 Hz, CH$_2$CH$_2$CH$_3$).

Example 28

4-(3-(4-tert-Butylphenyl)-2,3,4,8-tetrahydro-chromeno[6,7-e][1,3]oxazin-7-yl)phenol

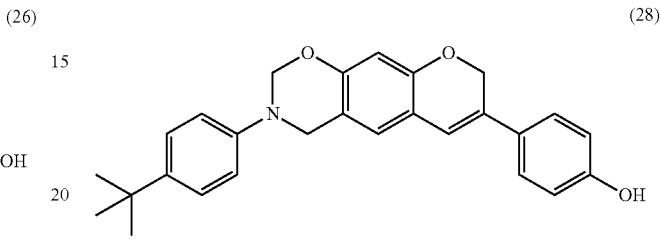

(28)

4',7-Dihydroxyisoflav-3-ene (500 mg, 2.08 mmol) was dissolved in absolute ethanol (10 mL). 4-tert-Butylaniline (311 mg, 2.08 mmol) was added followed by formaldehyde solution (6 mL, 0.04 mol, 37 wt. %). The reaction was stirred at room temperature for 1 day. The white precipitate was collected to afford the title compound (134 mg, 15%).

$^1$H NMR (400 MHz, $d_6$-DMSO) δ 122 (9H, s, CH$_3$, CH$_3$, CH$_3$), 4.53 (2H, s, CH$_2$Ar), 5.00 (2H, s, H8), 5.39 (2H, s NCH$_2$O), 6.18 (1H, s, H10), 6.78 (2H, d, J=8.6 Hz, ArH), 6.86 (1H, s, H6), 7.04 (2H, d J=8.7 Hz, ArH), 7.24 (2H, d, J=8.7 Hz, ArH), 7.33 (2H, d, J=8.6 Hz, ArH), 9.63 (1H, s, OH).

Example 29

4-(3-(4-tert-Butylbenzyl)-2,3,4,8-tetrahydro-chromeno[6,7-e][1,3]oxazin-7-yl)phenol

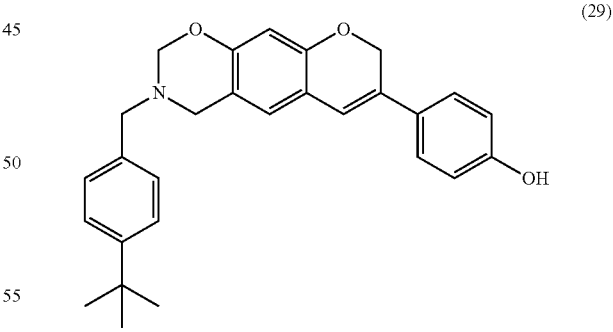

(29)

4',7-Dihydroxyisoflav-3-ene (500 mg, 2.08 mmol) was dissolved in absolute ethanol (10 mL). 4-tert-Butylbenzyl amine (340 mg, 2.08 mmol) was added followed by formaldehyde (6 mL, 0.09 mmol, 37 wt %). The reaction was stirred at room temperature for 1 day. The white precipitate was collected to afford the title compound (407 mg, 43%).

$^1$H NMR (400 MHz, $d_6$-DMSO) δ 1.28 (9H, s, CH$_3$, CH$_3$, CH$_3$), 3.80 (4H, s, CH$_2$Ar, NCH$_2$Ar), 4.84 (2H, s, NCH$_2$O), 5.03 (2H, s, H8), 6.24 (1H, s, H10) 6.73 (1H, s, ArH), 6.76

(1H, s, H6), 6.78 (2H, d, J=8.7, ArH), 7.24 (2H, d, J=8.1, ArH), 7.33 (2H, d, J=8.7, ArH), 7.36 (2H, d, J=8.2, ArH), 9.63 (1H, s, OH).

Example 30

4-(3-(Naphth-1-yl-methyl)-2,3,4,8-tetrahydro-chromeno[6,7-e][1,3]oxazin-7-yl)phenol

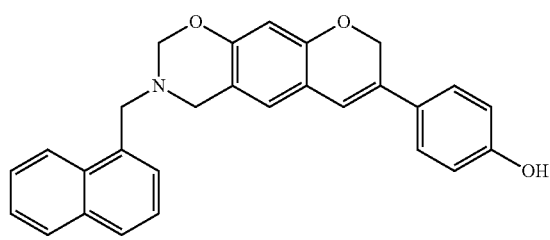

(30)

4',7-Dihydroxyisoflav-3-ene (500 mg, 2.08 mmol) was dissolved in absolute ethanol (10 mL). 1-Naphthalene-methylamine (327 mg, 2.08 mmol) was added followed by formaldehyde (6 mL, 0.09 mmol, 37 wt. %). The reaction was stirred for a day at room temperature. The white precipitate was collected to afford the title compound (337 mg, 38%).

$^1$H NMR (400 MHz, $d_6$-DMSO) δ 3.87 (2H, s, CH$_2$Ar), 4.27 (2H, s, NCH$_2$Ar), 4.90 (2H, s, NCH$_2$O), 5.05 (2H, s, H8), 6.30 (1H, s, H10), 6.76 (1H, s, ArH), 6.78 (1H, s, H6), 7.39 (1H, d, J=6.8, ArH), 7.47 (1H, dd, J=7.6, 7.6, ArH), 7.54 (2H, m, ArH), 7.89 (1H, d, J=8.1, ArH), 7.94 (1H, m, ArH), 8.22 (1H, m, ArH), 9.64 (1H, s, OH).

Example 31

4-(3-(3,4-Dimethylphenyl)-2,3,4,8-tetrahydro-chromeno[6,7-e][1,3]oxazin-7-yl)phenol

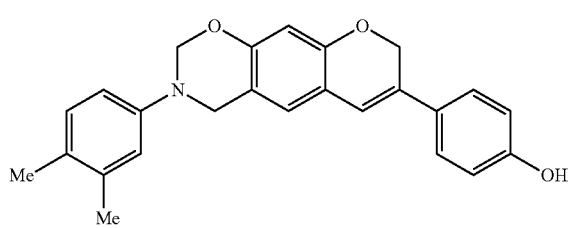

(31)

4',7-Dihydroxyisoflav-3-ene (500 mg, 2.08 mmol) was dissolved in absolute ethanol (10 mL). 3,4-Dimethylaniline (293 mg, 2.08 mmol) was added followed by formaldehyde (6 mL, 0.09 mmol, 37 wt. %). The reaction was stirred for a day at room temperature. The light pink precipitate was collected to afford the title compound (166 mg, 21%).

$^1$H NMR (400 MHz, $d_6$-DMSO) δ 2.10 (3H, s, CH$_3$), 2.15 (3H, s, CH$_3$), 4.52 (2H, s, NCH$_2$Ar), 5.00 (2H, s, H8), 5.37 (2H, s, NCH$_2$O), 6.18 (s, H10), 6.78 (1H, s, H6), 6.81 (1H, dd, J=8.2, 2.4, ArH), 6.85 (1H, s, ArH), 6.93 (1H, d, J=2.0, ArH), 6.97 (1H, d, J=8.2 ArH), 7.33 (1H, d, J=8.6), 9.63 (1H, s, OH).

Example 32

4-(3-(4-Methoxyphenyl)-2,3,4,8-tetrahydrochromeno[6,7-e][1,3]oxazin-7-yl)phenol

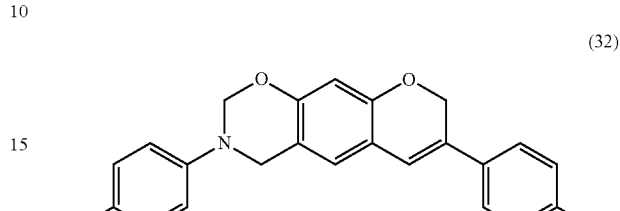

(32)

4',7-Dihydroxyisoflav-3-ene (500 mg, 2.08 mmol) was dissolved in absolute ethanol (10 mL). 4-Methoxy-aniline (271 mg, 2.08 mmol) was added followed by formaldehyde (6 mL, 0.09 mmol, 37 wt. %). The reaction was stirred for a day at room temperature. The pink precipitate was collected to afford the title compound (71 mg, 9%).

$^1$H NMR (400 MHz, $d_6$-DMSO) δ 3.67 (3H, s, OCH$_3$), 4.48 (2H, s, NCH$_2$Ar), 5.01 (2H, s, H8), 5.33 (2H, s, NCH$_2$O), 6.18 (1H, s, H10), 6.75 (1H, s, H6), 6.78 (2H, d, J=8.6, ArH), 6.81 (2H, d, J=9.0, ArH), 6.85 (1H, s, ArH), 7.05 (2H, d, J=9.0, ArH), 7.33 (2H, d, J=8.6, ArH), 9.63 (1H, s, OH).

In the above general methods, the structures may be optionally substituted or protected with appropriate substituents, or synthons or derivatives thereof. The compounds may be present as, for example, their salts, acetates, benzyl or silyloxy derivatives as can be determined by a skilled synthetic chemist and as generally described herein above. Hydroxy groups can be readily alkylated (MeI/base), acylated (Ac$_2$O/Py) or silylated (Cl—SiR$_3$/base) and likewise deprotected by standard methods known in the art.

2.0 Anti-Inflammatory Activity 2.1 Effect on Eicosanoid Synthesis in Human Monocytes Methods U937 cells were thawed and resuspended in RPM1 and 10% FCS at 2×10$^5$ cells per ml. The cells were incubated in 5% CO$_2$ at 37° C. and expanded in growing culture to at least 6.4×10$^7$ total cells. The cells were then resuspended in fresh medium and cultured with 5 retinoic acid (RA) at 2×10$^5$ cells per ml for a further 3 days (72 h). RA treated cells were washed 2× in serum-free RPM and resuspended in serum-free medium at 5×10$^6$ cells per ml. The cells were aliquotted into Teflon tubes at 1 ml per tube. Working stock solutions of each test compound were prepared at 0.1 mM, 1 mM and 10 mM as described above. For each test compound at each working dilution, 10 µl was added to 1 ml cells to achieve a final concentration of 0 (DMSO alone), 1, 10, and 100 µM for each test compound. Cells were incubated in triplicate with each concentration of test compound for 15 min at 37° C. After 15 min pre-incubation, each 1 ml tube of cells received 5 µl of a 100 mM solution of the calcium ionophore A23187 (to achieve 0.5 µM A23187). Incubation at 37° C. was continued for a further 30 min. After incubation, supernatants were collected by centrifugation at 2000 rpm for 10 min and stored at −20° C. until required for assay.

Results

Tables 1 and 2 below show the effect of test compounds (1) and (2) on $PGE_2$ synthesis and on $TXA_2$ synthesis in RA-stimulated U937 cells. Compound (2) is shown to inhibit $PGE_2$ synthesis whilst both compounds (1) and (2) were shown to inhibit $TXA_2$ synthesis at 100 μM.

TABLE 1

Effect of test compounds on $PGE_2$ synthesis in RA-stimulated U937 cells

| | $PGE_2$ (pg) Test compound concentration: | | | |
|---|---|---|---|---|
| | 0 μM | 1 μM | 10 μM | 100 μM |
| Compound 1 | 1.091 ± 0.101 | 1.431 ± 0.154 | 0.702 ± 0.237 | 0.555 ± 0.064 |
| Compound 2 | 1.091 ± 0.101 | 1.303 ± 0.044 | 0.948 ± 0.111 | 0.158 ± 0.027$^a$ |

$^a$Significantly different from control (zero dose)

TABLE 2

Effect of test compounds on $TXA_2$ synthesis in RA stimulated U937 cells

| | $TXA_2$ (pg) Test compound concentration: | | | |
|---|---|---|---|---|
| | 0 μM | 1 μM | 10 μM | 100 μM |
| Compound 1 | 34.284 ± 10.286 | 48.720 ± 2.927 | 17.421 ± 5.747 | 6.397 ± 0.557$^a$ |
| Compound 2 | 34.284 ± 10.286 | 30.680 ± 2.708 | 21.298 ± 0.914 | 2.313 ± 0.113$^a$ |

$^a$Significantly different from control (zero dose)

2.2 Effect on Synthesis of TNFα in Human Monocytes
Methods

Figure 1B:
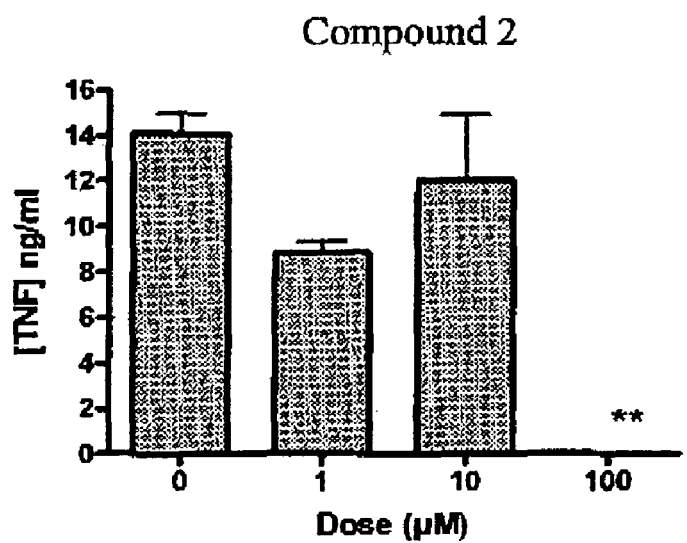

Human peripheral blood monocytes were isolated from buffy coats by lymphoprep gradient separation of mononuclear cells followed by counter-current centrifugal elutriation (Demasi et al. 2000). Test compounds were dissolved in DMSO and added to fresh monocytes to achieve concentrations of 0, 10 and 100 μM. After 30 min, LPS was added to achieve a final concentration of 200 ng/mL. After 1 h, supernatants were removed and TNFα measured by ELISA previously described (Demasi et al. 2003). ANOVA followed by Newman-Keuls multiple comparisons test was used to examine differences between doses and the control values.
Results Compounds (1) and (2) were shown to reduce the synthesis of TNFα by human monocytes stimulated with LPS (see FIGS. 1a and 1b).

2.3 Anti-Inflammatory Effect in the Murine Macrophage Cell Line, Raw 264.7
Methods The mouse macrophage cell line RAW 264.7 was cultured in DMEM supplemented with foetal calf serum (FCS), 2 μM glutamine and 50 U/ml penicillin/streptomycin. Cells were treated with either test compound (in 0.025% DMSO) or vehicle alone, and added one hour before 50 ng/ml LPS. After incubation for 24 h, culture media was collected for $PGE_2$ or $TXB_2$ measurement by ELISA (Cayman Chemical), and TNFα measurement using an ELISA (Becton Dickinson).

Nitrite concentration is a quantitative indicator of NO production and was determined by the Griess Reaction. Briefly, 100 μL of Griess reagent was added to 50 μL of each supernatant in duplicate. The absorbance at 550 nm was measured (Molecular Devices, SpectraMax 250 microplate spectrophotometer, CA, USA), and nitrite concentrations were determined against a standard curve of sodium nitrite. The percentage nitrite inhibition was calculated as:

[100−(nitrite concentration of sample/nitrite of vehicle control LPS cells)×100].

Results

Figure 2:
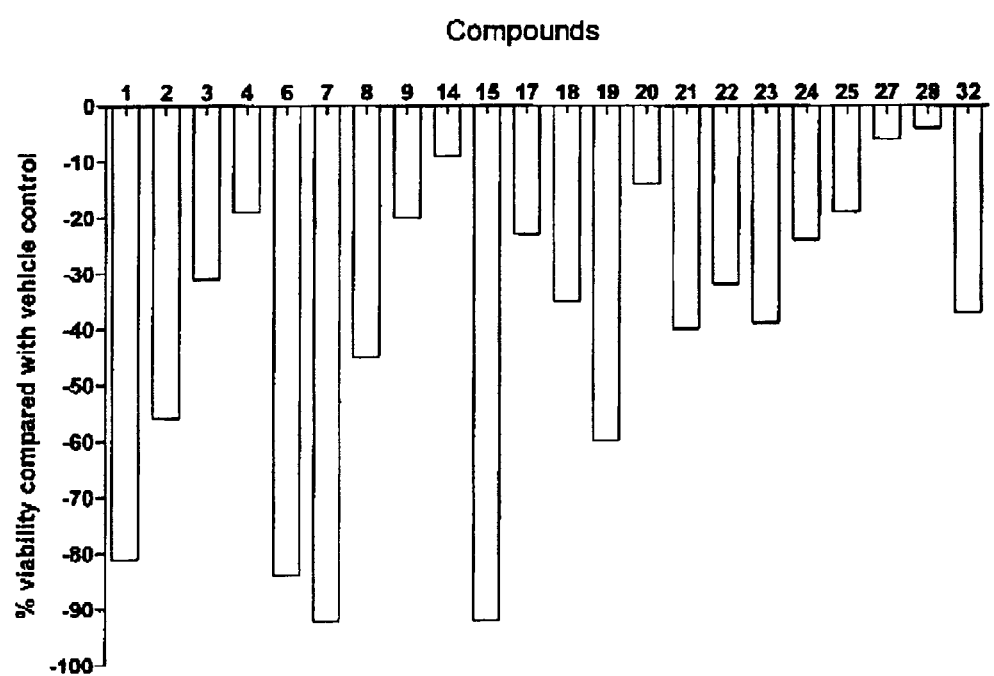
FIG. 2. depicts the effect on cell viability of incubation with 10 μM test compound with LPS-stimulated RAW 264.7 murine macrophages by test compounds relative to treatment with vehicle alone.

Test compounds were examined a concentration of 10 μM. From FIG. 2 it can be seen that some of the compounds exhibited some toxicity, which would have influenced the amount of inhibition they caused for various analytes. Consequently, to assess the effect of test compounds on various analytes, cell viability was taken into consideration with the use of the formula:

Actual effect of test compound=measured effect−(effect on cell viability×measured effect)

Figure 3:
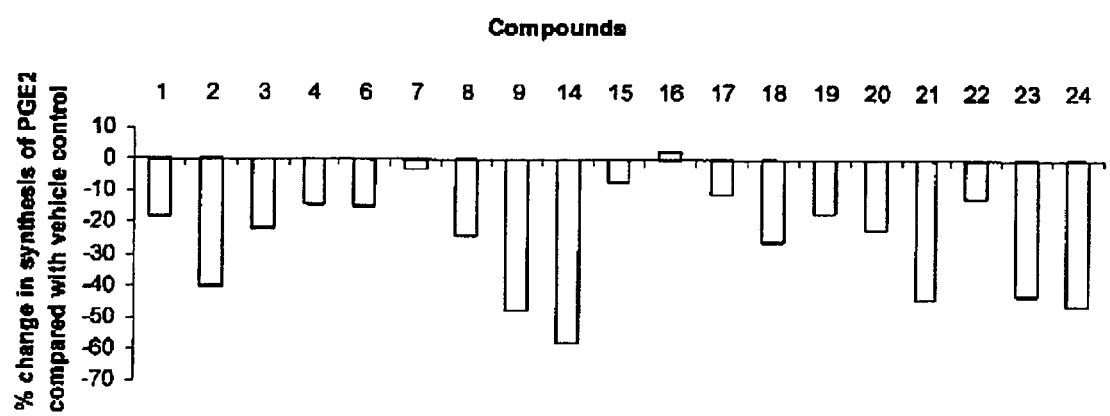
FIG. 3. depicts the mean, change of LPS-induced PGE2 synthesis in RAW 264.7 murine macrophages by test compounds relative to treatment with vehicle alone.
Figure 4:
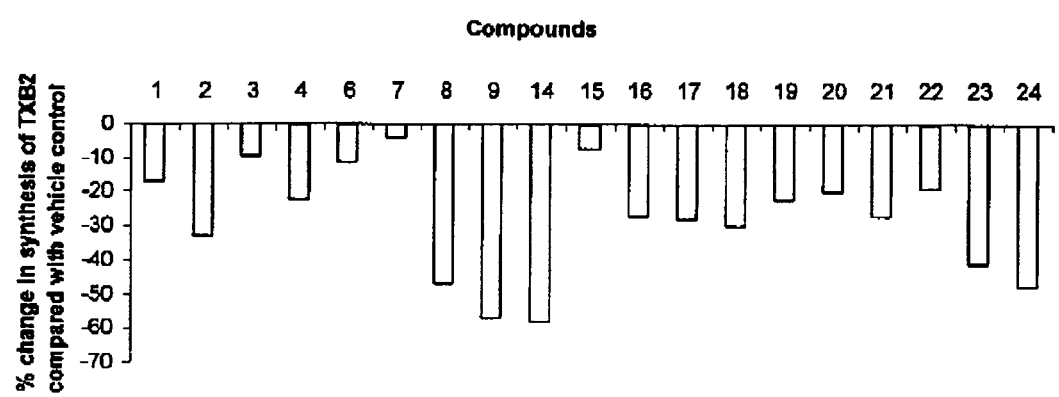
FIG. 4. depicts the mean change of LPS-induced TXB2 synthesis in RAW 264.7 murine macrophages by test compounds relative to treatment with vehicle alone.
Figure 5:
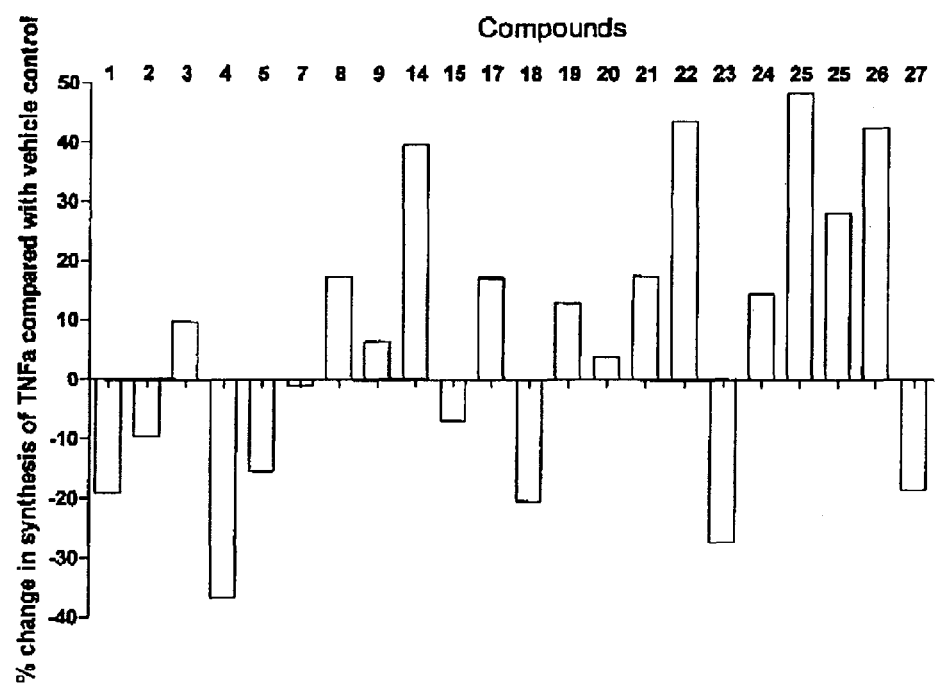
FIG. 5. depicts the mean change of LPS-induced TNFα synthesis RAW 264.7 murine macrophages by test compounds relative to treatment with vehicle alone.
Figure 6:
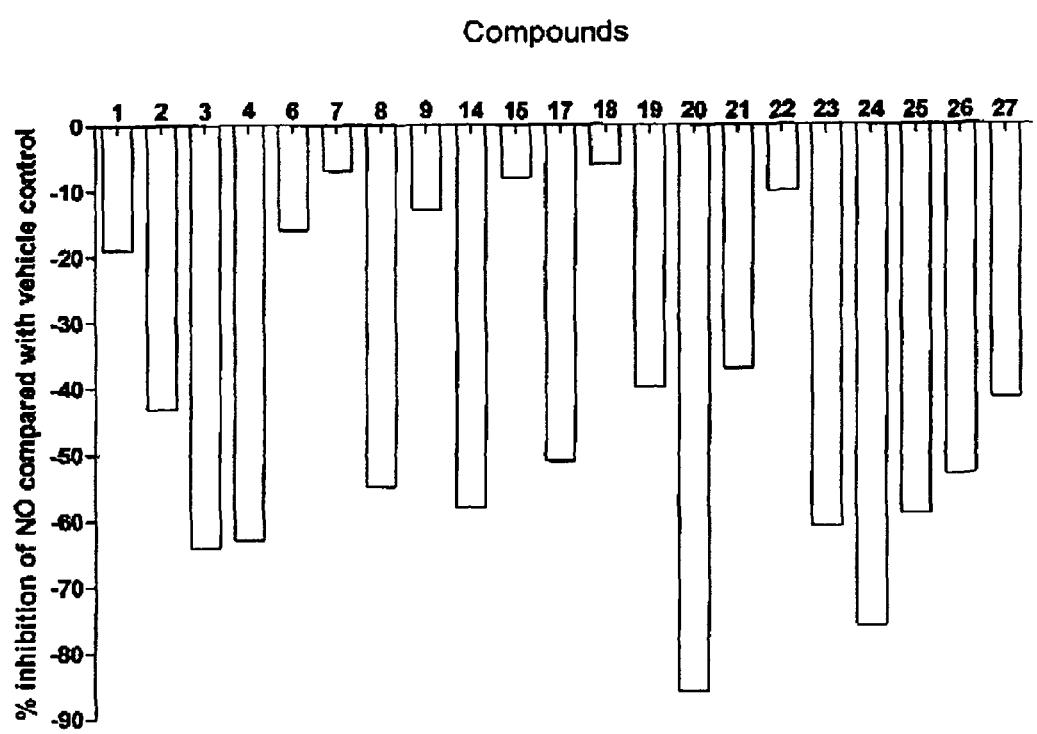
FIG. 6. depicts the mean change of LPS-induced NO synthesis in RAW 264.7 murine macrophages by test compounds relative to treatment with vehicle alone.

Compounds were tested relative to treatment with vehicle alone on RAW 264.7 murine macrophages. The mean change of LPS-induced $PGE_2$ synthesis is shown in FIG. 3 where the greatest inhibition is exhibited by compounds (2), (9), (14), (12), (23) and (24). The mean change of LPS-induced $TXB_2$ synthesis is shown in FIG. 4 where the greatest inhibition is exhibited by compounds (2), (8), (9), (14), (23) and (24). The mean change of LPS-induced TNFα synthesis is shown in FIG. 5 where the greatest inhibition is exhibited by compounds (1), (4), (6), (17) and (22). The mean change of LPS-induced NO synthesis is shown in FIG. 6 where the greatest inhibition is exhibited by compounds (3), (4), (7), (14), (19), (22), (23) and (24).

2.4 Effect on NFκB Production in Transfected Human Macrophage Cell Line, THP-1
Methods The assay utilizes a genetically modified THP-1 cell line and GeneBLAzer® beta-lactamase technology (Invitrogen Corp). The human THP-1 monocyte/macrophages contain a stably-transfected beta-lactamase reporter gene under control of the NFκB response element They respond to stimulation with TNF-a, which leads to activation of the NFκB signaling pathway. Co-incubation of cells with TNF-a and test material allows quantitative determination of the ability of test material to inhibit TNFa-stimulated beta-lactamase production. Inflammatory index is calculated as the ratio of beta-lactamase product to beta-lactamase substrate.

In brief, genetically modified THP-1 cells were seeded into wells of a 96-well plate (50×10$^3$ cells/well) in the presence of RPMI 1640 medium (70 μl). TNFα was added to each well (10 μl) to give a final concentration of 7.5 ng/ml. Dialyzed bovine serum was added (10 μl). Compounds dissolved in DMSO (10 μL) were then added (5 wells for each compound). Each plate contained a no-cell control (4 wells), a no-serum control (4 wells) and two serum controls. Plates were incubated for 5 h at 37° C. to allow for NFκB-stimulated beta-lactamase production. LiveBLAzer™ FRET B/G Substrate (CCF4-AM) substrate was then added to assay. CCF4-AM is a Forster resonance energy transfer (FRET) based substrate for beta-lactamase developed by Invitrogen Corp. Once CCFA-AM enters a cell, it is converted to negatively charged CCF4 by endogenous esterases. Excitation of this substrate at 409 nm leads to efficient FRET between the coumarin and fluorescein moieties, resulting in a green fluorescence detectable at 530 nm. The presence of beta-lactamase leads to cleavage of CCF4 and results in a loss of FRET, resulting in a robust blue fluorescent signal detectable at 460 nm. Thus, activity of beta-lactamase (a marker of NFκB-promoter activity) is measured as a product to substrate ratio (blue/green fluorescence ratio: 460 nm/530 nm). The determination of inflammatory index has a within-plate CV of 2.1% and a between-plate CV of 8.9%

Results

Compounds (1) and (2) were examined in this assay. It was found that 30 μM was the optimal concentration at which to compare the NFκB-inhibitory activity of test compounds. At 50 μM and 100 μM, the compounds reduced cell viability as can be seen from Table 3. Data are presented following incubation with test compound at 30 μM.

TABLE 3

Mean change in NFκB promoter activity in THP-1 cells by test compounds relative to treatment with vehicle alone.

| Compound | Inflammatory index | p value compared to control | % inhibition compared to control |
|---|---|---|---|
| Control | 11.56 ± 0.49 | — | — |
| Compound 1 | 6.31 ± 0.36 | p < 0.001 | 45.5% |
| Compound 2 | 7.54 ± 0.17 | p < 0.001 | 34.8% |

3.0 Anti-Oxidant Activity

Oxidized lipoproteins are thought to provoke a number of changes in cell functions that promote atherogenesis. Oxidized low density lipoprotein (LDL) is pro-inflammatory, it can cause endothelial dysfunction and it readily accumulates within the arterial wall (Rosenson 2004). Studies in animals have provided evidence of the release of oxidants in response to arterial injury, and macrophages and smooth muscle cells, the major types of cell left in the atherosclerotic lesion after angioplasty, can both elaborate active oxygen species (Libby and Ganz 1997). Consequently, the ability of a compound to inhibit the oxidation of LDL may contribute to its ability to reduce atherosclerosis overall. Compounds (1) ands (2) have been demonstrated in a number of assays to have robust antioxidant activity.

3.1 Effect on Free Radical Scavenging

Methods

The antioxidant (free radical trapping) activity of test compounds was assessed using the stable free radical compound 2,2-diphenyl-1-picrylhydrazyl (DPPH). A stock solution of DPPH was prepared at a concentration of 0.1 μmM in ethanol and mixed for 10 minutes prior to use. Test compounds at a concentration of 100 μM were reacted with DPPH for, 20 minutes, alter which time the absorbance at 517 nm was determined. Initial screening of was done at 100 μM. The change in absorbance at 517 nm was compared to a reagent blank (DPPH with ethanol alone). Where a compound was found to have significant free radical scavenging activity ($\Delta_{Abs}$>0.3) at 100 μM and a dose response curve was produced. The $IC_{50}$ values were estimated as the concentration of test compound that caused a 0.6 change in absorbance (with 1.2 absorbance units representing total scavenging of the DPPH radical).

Results

TABLE 4

Free radical scavenging ability of test compounds - $EC_{50}$ (μM)

| Compound | $EC_{50}$ (μM) |
|---|---|
| 1 | 18.8 |
| 2 | 21.4 |
| 3 | 20 |
| 4 | 22.5 |
| 6 | 24 |
| 7 | 22.5 |
| 8 | 16 |
| 9 | 36 |
| 13 | 41 |
| 15 | 22.5 |
| 16 | 22 |
| 17 | 40 |
| 18 | 29 |
| 19 | 41 |
| 20 | 38 |
| 21 | 44 |
| 22 | 21 |
| 23 | 27 |
| 24 | 24 |
| 25 | 23 |
| 26 | 26 |
| 27 | 26 |

3.2 Effect on Inhibiting the Oxidation of Low Density Lipoprotein (LDL).

Methods

Blood was collected by venipuncture and plasma separated by centrifugation. LDL was then isolated from plasma using a 4-step sodium chloride density gradient and ultracentrifuged at 200,000 g for 20 hours at 4° C. The collect LDL was purified by passage through gel filtration PD10 column to remove excess salt and EDTA, and stored in the dark at 4° C. to prevent auto-oxidation and used with two weeks of isolation. The LDL cholesterol content was measure using a standard enzymatic method and protein concentration determined by the Lowry method using BSA as the standard.

One the day of each experiment a 2 mL aliquot of LDL was passed through a second PD10 column and diluted with chelex treated PBS (100 mM) to give a standard protein concentration of 0.1 mg/mL, i.e. final concentration per reaction. Oxidation reactions were initiated by the addition of freshly prepared $Cu^{2+}$ solution, such that the final concentration of $CuSO_4$ was 5 μM. For inhibition studies, LDL was pre-treated with the five compounds, at final concentrations of 0.1, 1.0, 10 and 100 μM, for 2 minutes at room temperature prior to the addition of copper solution and subsequently incubated at 37° C. The extent of lipoprotein oxidation was determined by measuring the formation of lipid-peroxides on aliquots removed every 30-minute over a 3-hour period. Peroxides were determined at each time point by the ferrous oxidation-xylenol orange (FOX) assay using standard hydrogen peroxide curve (5 to 200 μM). Compounds (1) and (2) were examined in at least two separate experiments performed on separate days.

The non-specific binding of test compounds to $Cu^{2+}$ was also examined in duplicate on different days. A stock solution of test compounds was prepared in DMSO at a concentration of 5 mM. The UV/V is absorption spectra of was then determined between 200 and 800 nm after dilution of test compounds to 25 μM in phosphate buffer (10 mM, pH 7.2, chelex treated). Interactions of the compounds with copper(II) were determined by scanning a second overlaying absorption spectrum over 200 to 800 nm, in which 25 μM $CuSO_4$ solution was added to a fresh 25 μM solution of test compounds and mixed for 20 seconds.

Results

The LDL oxidation lag period was approximately 60 minutes and maximum oxidation was achieved by 120-180 minutes. The ability of test compounds to inhibit LDL oxidation increased with increasing concentration from 0.01 to 10 μM. The concentration at which 50% of the oxidation was inhibited, the $EC_{50}$ was calculated as 0.61 μM for compound (1) and 0.63 μM for compound (2).

There were no significant shifts to absorbance bands of test compounds with $Cu^{2+}$ at a 1:1 molar ratio. There was a very small and consistent increase in the absorbance bands of each compound with $Cu^{2+}$ compared to the compounds alone. From these results it can be concluded that the test compounds did not interact with $Cu^{2+}$. This also indicates that the underlying mechanisms of inhibition of LDL oxidation are most likely not due to a direct interaction of $Cu^{2+}$ ions with the test compounds.

TABLE 5

Raw data for time-course lipid peroxide formation in the absence of test compound

| Time (min) | LDL 0.1 mg/ml | $Cu^{++}$ 5 μM | LDL 0.1 mg/ml + $Cu^{++}$ 5 μM |
|---|---|---|---|
| 0 | 9.18 ± 1.32 | 3.76 ± 1.54 | 12.59 ± 1.73 |
| 30 | 9.37 ± 0.50 | 3.35 ± 0.43 | 15.71 ± 0.94 |
| 60 | 8.90 ± 0.93 | 3.29 ± 1.11 | 31.90 ± 1.58 |
| 90 | 8.84 ± 0.60 | 3.26 ± 1.32 | 112.12 ± 3.98 |
| 120 | 8.90 ± 0.29 | 2.53 ± 0.81 | 176.28 ± 6.31 |
| 180 | 9.60 ± 0.07 | 1.70 ± 3.67 | 193.10 ± 17.24 |

TABLE 6

Raw data for time-course lipid peroxide formation in the presence of Compound (1)

| Time (min) | LDL 0.1 mg/ml + Compound (1) + $Cu^{++}$ 5 μM | | | | Compound (1) |
|---|---|---|---|---|---|
| | 0.1 μM | 1.0 μM | 10 μM | 100 μM | 100 μM + $Cu^{++}$ 5 μM |
| 0 | 10.39 ± 1.60 | 10.03 ± 1.40 | 10.08 ± 2.40 | 12.06 ± 2.1 | 6.73 ± 4.21 |
| 30 | 13.26 ± 1.94 | 11.37 ± 2.07 | 10.87 ± 6.04 | 15.95 ± 3.6 | 14.41 ± 1.40 |
| 60 | 24.45 ± 2.91 | 11.33 ± 2.72 | 14.91 ± 3.66 | 17.88 ± 4.7 | 17.99 ± 4.54 |
| 90 | 78.52 ± 5.80 | 16.30 ± 2.60 | 16.54 ± 4.49 | 20.73 ± 4.5 | 21.78 ± 7.78 |
| 120 | 147.9 ± 0.66 | 30.44 ± 1.54 | 18.24 ± 2.12 | 23.57 ± 2.2 | 24.41 ± 5.01 |
| 180 | 171.1 ± 26.7 | 131.5 ± 16.3 | 19.20 ± 5.20 | 23.0 ± 5.9 | 26.70 ± 8.39 |

TABLE 7

Raw data for time-course lipid peroxide formation in the presence of Compound (2)

| Time (min) | LDL 0.1 mg/ml + Compound (2) + $Cu^{++}$ 5 μM | | | | Compound (2) |
|---|---|---|---|---|---|
| | 0.1 μM | 1.0 μM | 10 μM | 100 μM | 100 μM + $Cu^{++}$ 5 μM |
| 0 | 10.5 ± 2.93 | 10.22 ± 2.9 | 10.20 ± 2.6 | 12.09 ± 2.8 | 7.69 ± 3.8 |
| 30 | 13.9 ± 2.51 | 11.62 ± 2.4 | 15.99 ± 0.1 | 15.93 ± 5.4 | 14.97 ± 0.4 |
| 60 | 23.7 ± 4.71 | 12.08 ± 3.2 | 18.26 ± 0.8 | 19.40 ± 7.8 | 19.19 ± 2.1 |
| 90 | 75.1 ± 8.43 | 18.25 ± 3.2 | 20.64 ± 1.3 | 23.27 ± 8.7 | 24.30 ± 4.3 |
| 120 | 138.5 ± 2.94 | 35.12 ± 0.4 | 23.68 ± 1.2 | 28.76 ± 5.0 | 28.31 ± 2.8 |
| 180 | 173.7 ± 34.4 | 133.1 ± 18.3 | 24.6 ± 21.9 | 28.6 ± 12.9 | 33.20 ± 6.7 |

3.3 Effect on Peroxyl Radical-Induced Red Blood Cell (RBC) Lysis

Methods

Freshly collected heparinised venous blood (10 ml, on ice) was aliquotted into 1.8 ml sterile Eppendorf tubes and centrifuged for 10 minutes at 2600 rpm at 4° C. Plasma and buffy coat layers were removed (approximately 900 ml) and packed red blood cells (RBC) were then washed by the addition of 900 ml of sterile, ice cold PBS. This washing procedure was repeated twice. Packed RBC were resuspended by the addition of 900 ml of ice-cold, sterile PBS (and termed RBC stock). RBC stocks were stored at 4° C. for a maximum of three days. All working suspensions of RBC were prepared fresh daily by diluting 200 ml of RBC stock into 10 ml of ice-cold, sterile PBS and 50 ml added to each well.

Stocks of AAPH were freshly prepared for individual experiments as follows. AAPH (1.22 gm) was dissolved in 7.5 ml of PBS to yield a 4× stock at 600 mM and 50 ml aliquots (final concentration of 150 mM) were then added to each well to initiate the lysis assay. Stock solutions of test compounds (40 mM in 100% DMSO) were diluted in sterile PBS to yield final concentrations of 100, 30 and 10 mM per well. Appropriate controls were included in each experiment. All compound dilutions were adjusted to give final DMSO concentrations in each well of 0.25%. Peroxy-induced RBC lysis assays were performed in 96-flat bottom well microtitre plates with a total volume of 200 ml per well. Turbidity of RBC suspensions were monitored using a Tecan microplate reader at 690 nm (37° C.) with gentle vortexing. Assays were performed in quadruplicate and readings were taken every 5 minutes over 5 hours. RBC lysis curves were constructed by plotting absorbance (mean of 4 readings) against time. Time to half-lysis was calculated by taking the highest absorbance reading (no lysis) and the lowest absorbance reading (maximum lysis). The sum of these two readings divided by two gave the absorbance at half-lysis. Simple regression analysis was used to calculate the time at which half-lysis absorbance occurred.

Results

Compounds (1) and (2) were examined in this assay. Both compounds were found to have antioxidant activity by delaying the AAPH-induced time to half-lysis of red blood cells.

TABLE 8

Time taken to reach half-lysis following incubation with test compounds at 10 µM (min)

| Compound | Time (min) |
| --- | --- |
| Vehicle | 40.0 |
| Compound (1) | 141.6 |
| Compound (2) | 124.3 |

4.0 Anti-Atherogenic Activity 4.1 Effect on Adhesion Molecule Expression in Arterial Cells Methods Inhibition of TNFα-stimulated endothelial cell activation by compounds was assessed by measuring surface expression of cell adhesion molecules with an ELISA method. Human arterial endothelial cells (HAEC) in growth medium (Cell Applications Inc.) were seeded into 96-well plates at a density of 10,000 cells per well. Plates were incubated overnight at 37° C. in a humidified incubator to allow for cells to become confluent. On the morning of the experiment, TNFα (10 µl, 2 ng/ml) was added to each well, which contained 100 µl of medium. Compounds were diluted in DMSO-containing medium (2.5% DMSO) to give a compound concentration of 100 and 300 µM. Compounds were added to wells so that final concentrations were 10 and 30 µM. DMSO-containing medium alone was added to zero concentration control wells. All samples were measured in quadruplicate (4 wells per treatment).

After incubation with compound, medium was removed and cells were probed with either non-specific IgG or specific mouse antibodies against E-selectin, ICAM or VCAM (BD Biosciences—0.1 µg in 100 µL buffered saline with 10% heat-inactivated human serum). Adhesion molecule expression was detected by addition of sheep anti-mouse antibody/horseradish peroxidase conjugate. Plates were allowed to stand for 30 minutes—monolayers were then washed, and sheep anti-mouse antibody/horseradish peroxidase conjugate (1:500 in 100 µL HBSS with 10% heat-inactivated human serum and 0.05% Tween 20) was added and left for 30 minutes. After further washing, 150 µL ABTS substrate (Kirkegaard and Ferry Laboratories) was added to each well and allowed to develop for 15 minutes. Optical density was measured at 405 nm with an ELISA reader (Titertek Multiscan, Flow Laboratories).

Results

Compounds (1) and (2) were examined in this assay. At 100 µM, test compounds markedly affected HAEC viability. For some compounds, HAEC viability was less than 80% at 30 µM. It was thus found that 10 µM was the most appropriate concentration for comparing the activity of compounds in this assay.

Figure 7A:
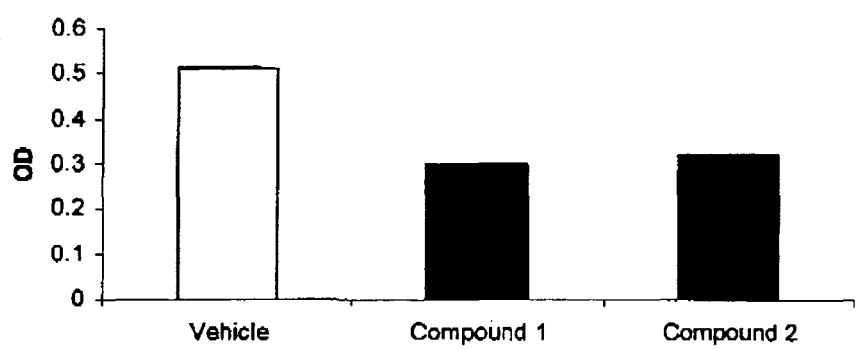
FIGS. 7a, 7b and 7c depict the effect of compounds (1) and (2) on expression of adhesion molecule mRNA with respect to VCAM-1, ICAM-1 and E-selectin.
Figure 7B:
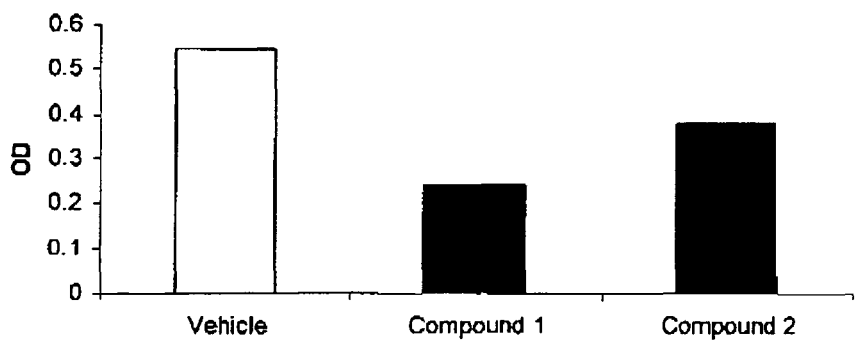
Figure 7C:
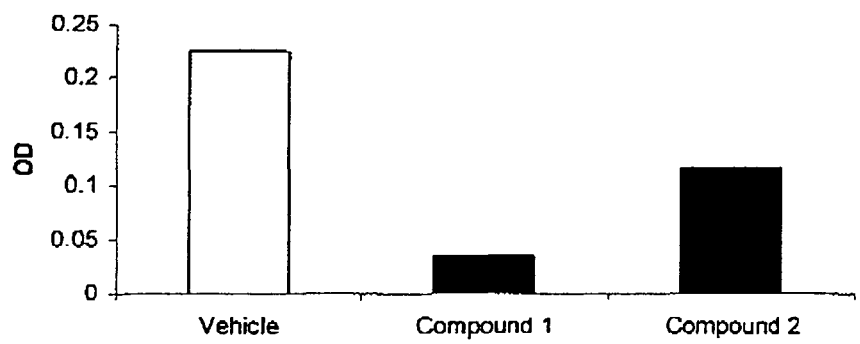

Both compounds had significant ability to inhibit TNFα-induced VCAM, ICAM-1 and E-selectin expression (see FIG. 7).

4.2 Effect on Proliferation of Vascular Smooth Muscle Cells

Methods

The effect of test compounds on human umbilical vein smooth muscle cells (HUVSMC) was examined. Cells were seeded into 96 well plates at a low seeding rate of $1.6 \times 10^3$ cells per well, and allowed to attach for 24 hours. The cells were then washed twice with medium without FCS and incubated in medium without FCS for 20 hours to serum starve them. Analogue was prepared in medium without FCS at 20 µM and added to the plates and incubated for one hour. Final analogue concentration was therefore 10 µM. The cells were then stimulated by adding medium +20% FCS, to give a final FCS concentration of 10%. The cells were incubated until the control cells i.e. those with FCS and no compound, were just confluent (5 days). An MTT assay was performed, and difference in absorbance in analogue treated cells from the control was calculated using the formula:

test/control*100−100.

Results

Figure 8:
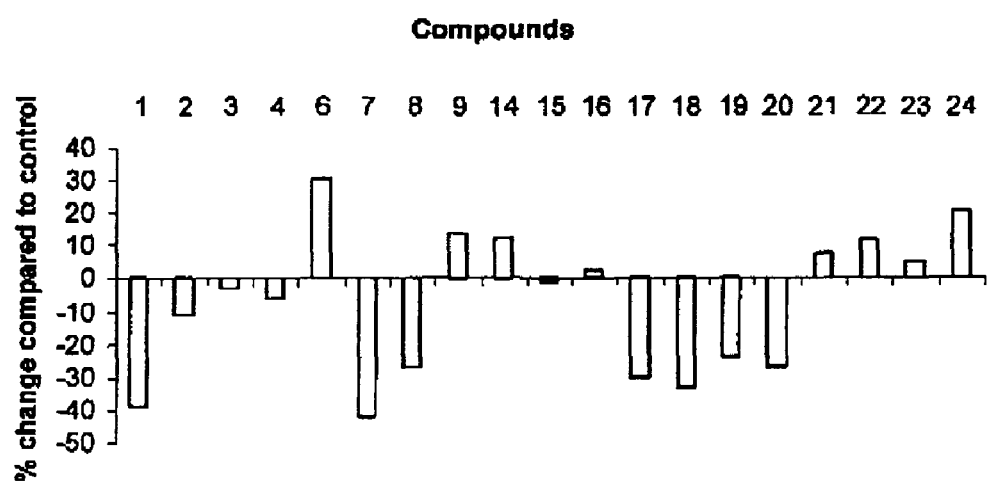
FIG. 8 depicts the effect on the proliferation of HUVSMCs following incubation with 10 μM of test compound.

The effect of test compounds on the proliferation of HUVSMCs showed that at 10 µM, compounds (1), (2), (7), (8), (17), (18), (19) and (20) significantly inhibited the proliferation induced by FCS (see FIG. 8).

5.0 Anti-Inflammatory Activity in Murine Ear Inflammation

Compounds were examined for their ability to inhibit ear swelling in mice induced by the topical application of several inflammogens—arachidonic acid (AA) and 4-β-phorbol 12-myristate 13-acetate (PMA).

The inflammatory response due AA, the immediate precursor of the eicosanoids, is due to formation of AA metabolites via both the cyclooxygenase (COX) and lipoxygenase (LOX) pathways (Young et al. 1984). AA induces an early (10-15 min) increase in both $PGE_2$ and LTC4 synthesis which precedes the increase in ear thickness (Opas et al. 1985; Chang et al. 1986).

Inflammation induced by PMA involves activation of protein kinase C (PKC), a phospholipid-dependent protein enzyme which plays a key role in a range of signal induction processes (Silvan et al. 1996; Bermejo et al. 1998). In other words, PMA is a PKC activator (Kuchera et al. 1993). PKC mediates activation of phospholipase A2, resulting in the release of free AA and the subsequent synthesis of leukotrienes (LTs) and prostaglandins (PGs). The inflammation is primarily mediated by $PGE_2$, as levels of $PGE_2$ but not $LTB_4$ and $LTC_4$ are elevated in the ears of PMA-treated mice (Ashendel and Boutwell 1979; Bermejo et al. 1998; Alexandre-Moreira et al. 1999).

Methods

Groups of 5-6 female BALB/c mice (ARC, WA, Australia), weighing 15-21 g were injected intraperitoneally (i/p) with test compound at 25 mg/kg delivered in polyethylene glycol (PEG) 400: phosphate buffered saline (PBS) 1:1 or ethanol: propanediol: PBS 4:9:7 either 30 min prior to or immediately before the inflammogen was applied to the ears. Mice were anaesthetised using isoflurane and baseline thickness of both ears was measured using a spring micrometer. Each mouse received a total of 20 µL of either AA in ethanol (50 mg/ml or 200 mg/ml) or PMA in either ethanol or acetone (0.2 mg/ml) applied to the inner and outer surfaces of each pinna (i.e. 0.5 mg or 2 mg AA or 2 µg PMA per ear). Mice were anaesthetised again to re-measure the ears at 1 h post-AA application and 5 h after PMA.

The difference in ear swelling pre- and post-application of inflammogen for each ear was calculated, and the average for the two ears of each mouse taken. The difference in mean swelling of each test group compared to the group given vehicle alone was calculated using a general ANOVA using Dunnett's Multiple Comparison test when multiple compounds were tested in the one experiment or a two-tailed impaired t-test when only one compound was tested (Prism 4, Graphpad Software).

The data has been presented graphically as the mean percentage inhibition of oedema, calculated as:

[1-[(mean % change ear thickness test group/mean % change ear thickness control group)×100]].

Results

The relative amount by which treatment with a test compound inhibited AA- and PMA-induced ear oedema are presented in Tables 9 and 10 below.

TABLE 9

Change in ear thickness in response to the application of AA

| Compound | Change in ear thickness (mean ± SD, × 0.01 mm) | % Change compared with vehicle | Significance |
| --- | --- | --- | --- |
| Compound 1 | 20 ± 0.9 | −18 | p < 0.05 |
| Vehicle | 24.3 ± 1.6 | | |
| Compound 2 | 15.9 ± 4.2 | −39 | p < 0.01 |
| Vehicle | 24.9 ± 1.1 | | |

TABLE 10

Change in ear thickness in response to the application of PMA

| Compound | Change in ear thickness (mean ± SD, × 0.01 mm) | % Change compared with vehicle | Significance |
| --- | --- | --- | --- |
| Compound 1 | 28.9 ± 3.1 | −9 | NS |
| Vehicle | 31.8 ± 3.0 | | |
| Compound 2 | 30.9 ± 2.2 | −3 | NS |
| Vehicle | 31.8 ± 3.0 | | |

6.0 Vasodilatory Activity in the Rat Aortic Ring Assay

The vasodilatory capacity of test compounds was examined ex situ using the rat aortic ring assay. The addition of noradrenaline to the test bath causes the rings to contract, and if that vasoconstriction is inhibited by a test agent i.e. it antagonises the effect of noradrenaline, it suggests that that agent may have vasodilatory activity.

Methods

Male Sprague-Dawley rats (250±50 g) were euthanased with 80% $CO_2$ and 20% $O_2$. The thoracic aorta was excised and quickly mounted in organ-baths as described (Chin-Dusting et al. 2001). Full concentration-contractile curves were obtained to noradrenaline (0.1 nM-10 mM) with and without test compounds delivered at a concentration of 1 µg/ml. Experiments were repeated in n=5 different rings from 5 different animals. Only one compound at any one concentration was tested on any one ring from any one animal. Sigmoidal dose response curves were fitted for the data and the log $EC_{50}$ calculated (Prism 4, GraphPad Software). The difference in these values between the presence and absence of test compound was calculated using a two-tailed paired t test. The effects of β-oestradiol and vehicle alone were examined as a positive and negative control respectively.

Results

Figure 9A:
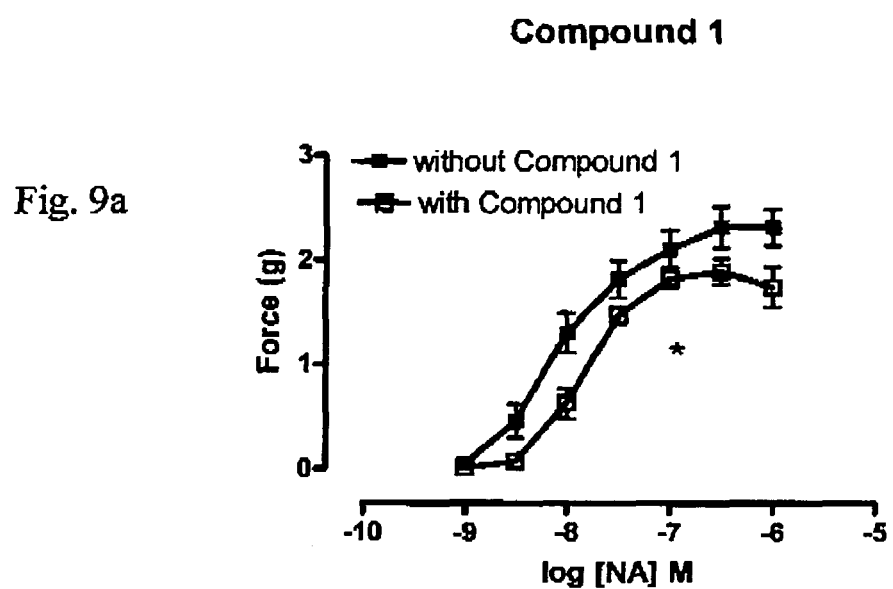
FIGS. 9a and 9b depict the effect of compounds (1) and (2) respectively on the contractile force of noradrenaline.
Figure 9B:
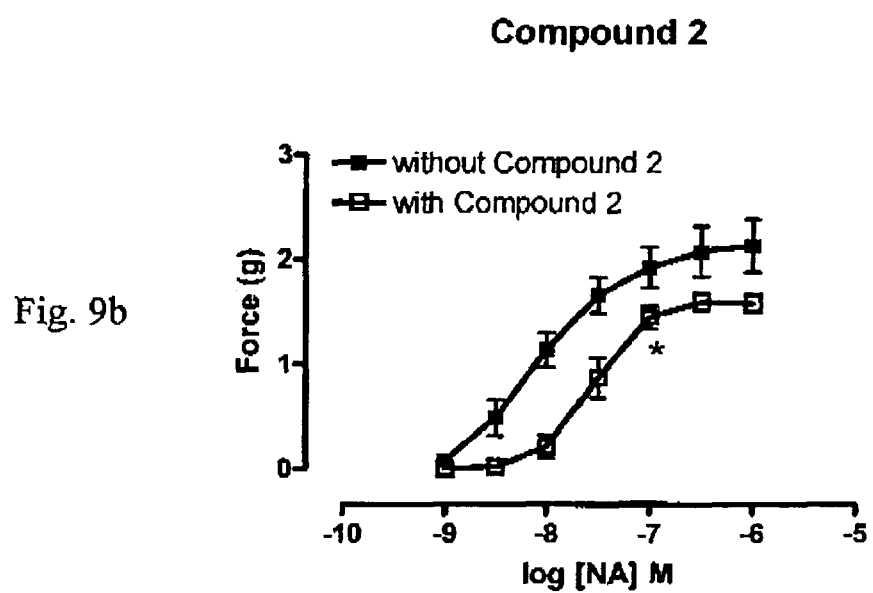

Compounds (1) and (2) were examined in this assay. Both compound (1) (p=0.0252) and compound (2) (p=0.0115) significantly inhibited the contractile response (log $EC_{50}$) of the aortic ring to noradrenaline compared with vehicle alone (see FIG. 9). These data indicate that compounds (1) and (2), in addition to being cardioprotective, are indicated to have cardiovascular activity as well as.

7.0 Immunomodulating Activity

Method

Male Skh-1:HR 1 (hairless) mice, approximately six weeks old were killed by cervical dislocation. Single cell suspensions were made from the spleen and erythrocytes were lysed in buffer (0.14 M $NH_4Cl$, 17 mM Tris, pH 7.2). The remaining splenocytes were cultured in RPMI-1640 (Gibco) supplemented with 10% (v:v) FBS, 200 mM L-glutamine, penicillin/streptomycin and 50 mM 2-mercaptoethanol. Splenocytes were added to quadruplicate wells containing either concanavalin A (ConA, Sigma-Aldrich— 0.4 µg/well), LPS (Sigma-Aldrich—1 µg/well) or no mitogen, as well 10 µM of test compound in DMSO. Samples were analysed after 3 days incubation at 37° C. in 5% $CO_2$ in air. Methylthiazoletetrazolium (MTT) is bioreduced by viable cells into a coloured formazan product that is soluble in DMSO. Thus the quantity of formazan product is directly proportional to the number of living cells in culture, and can be measured using a spectrophotometer at 570 nm. MTT was added to each well, incubated for a further 4 hrs and then colour developed with 0.04 N HCl in isopropanol. Culture supernatants were stored after collection at −80° C. and analysed by ELISA (BD Biosciences) for IFN-γ (a Th-1 cytokine) and for T cells alone, IL-6 (a Th-2 cytokine).

Results

Figure 10:
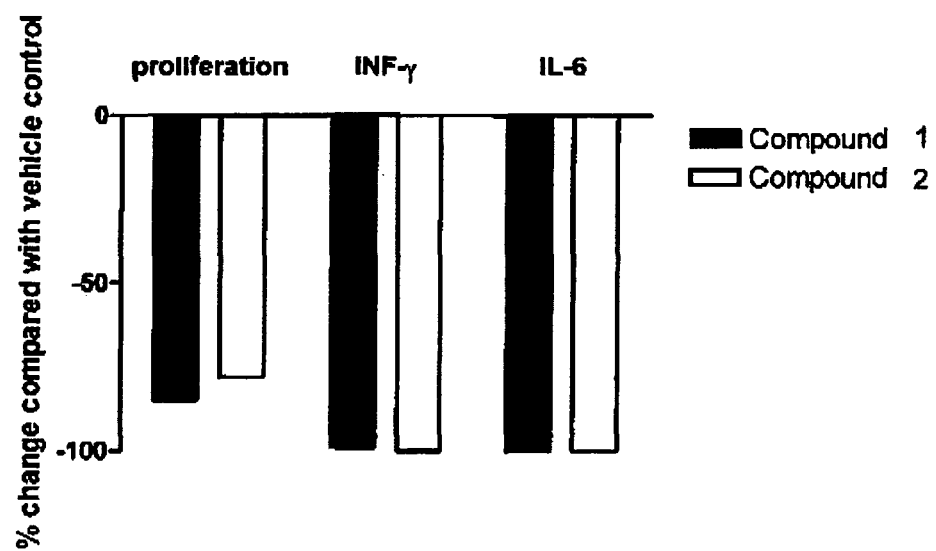
FIG. 10 depicts the effect of incubation with 10 μM of test compound on T cell proliferation and cytokine production.
Figure 11:
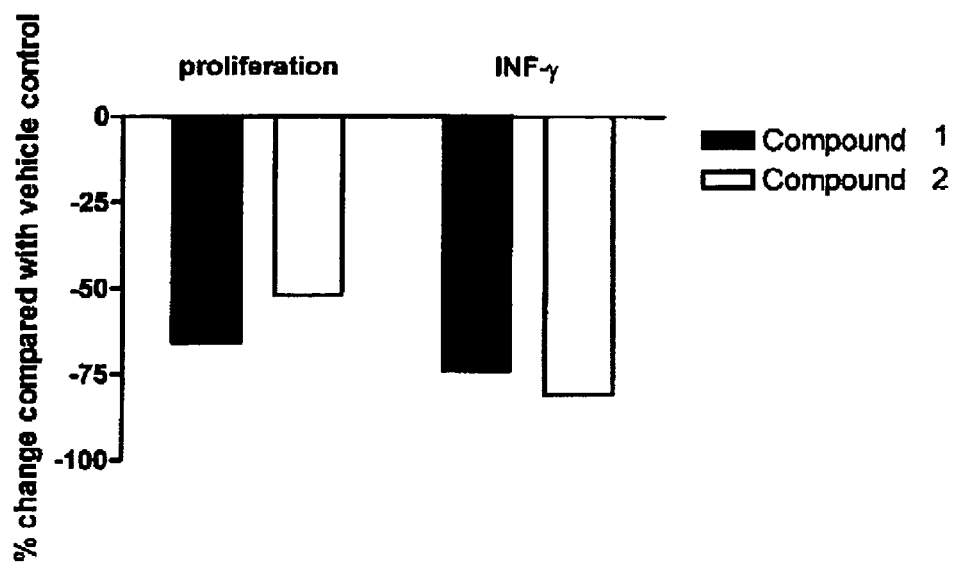
FIG. 11 depicts the effect of incubation with 10 μM of test compound on B cell proliferation and cytokine production.
Figure 12:
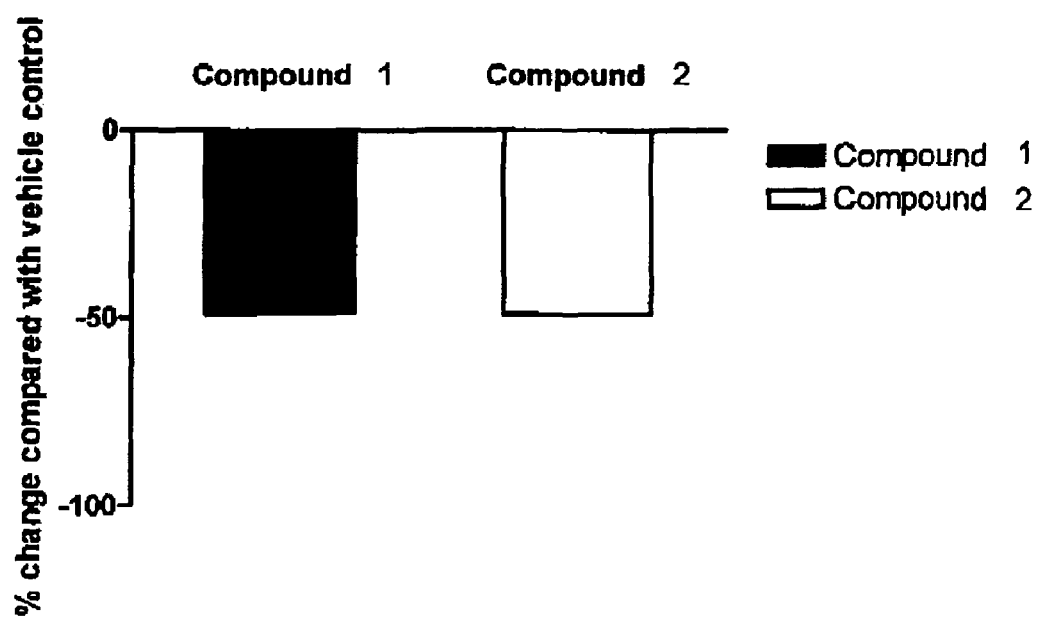
FIG. 12 depicts the effect of incubation with 10 μM of test compound on the proliferation of unstimulated lymphocytes.
Figure 13A:
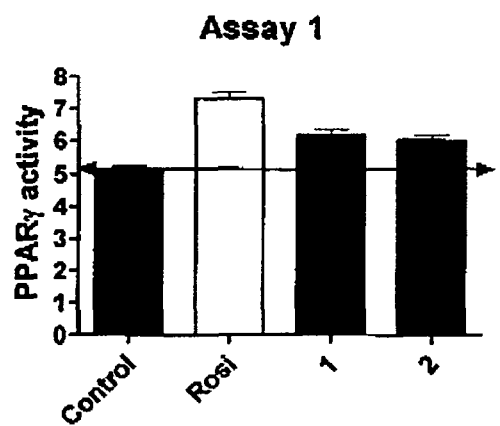
FIGS. 13a, 13b, 13c and 13d depict PPARγ activity of test compounds examined at a concentration of 1 μM. Data are from four separate assays. Rosi=rosiglitazone 0.1 μM.
Figure 13B:
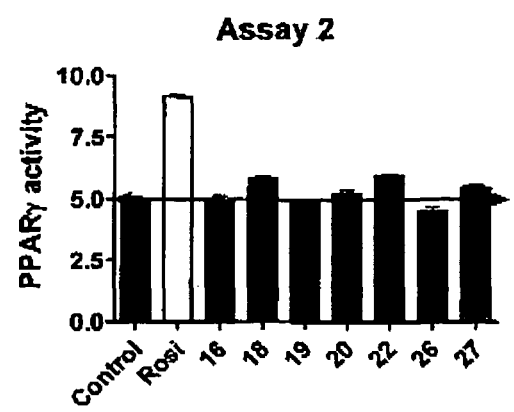
Figure 13C:
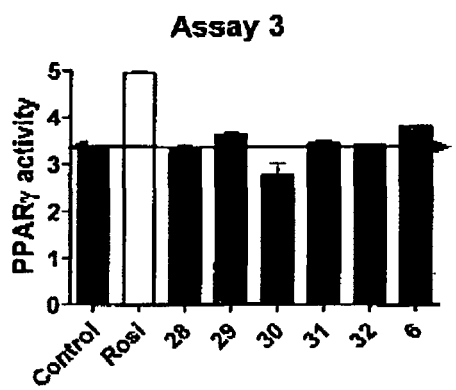
Figure 13D:
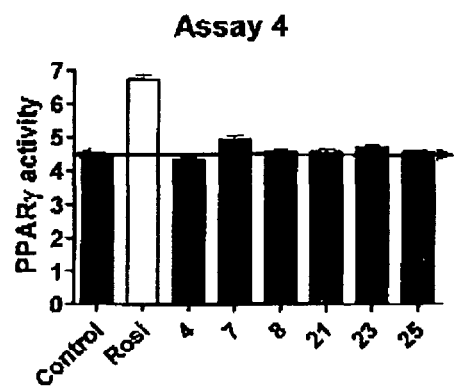

Compounds (1) and (2) were examined in four individual mice. Both compounds were markedly and significantly immunosuppressive to both T cells and B cells. This effect was further evidenced by a concomitant reduction on the synthesis of INF-γ and IL-6 into the supernatant. Some of this immunosuppression is likely to be due to direct cytotoxicity by test compound, as viable cell numbers were reduced by approximately 50% in the absence of mitogenic stimulation. Data from one mouse are presented in FIGS. 10, 11 and 12.

8.0 Peroxisome Proliferator-Activated Receptor Activity

Peroxisome proliferator-activated receptors (PPAR) are transcription factors which is a member of the nuclear hormone receptor super family. Activation of PPARγ by a ligand causes modulation of specific genes, the effects amongst which are inhibition of the production of various inflammatory mediators (eg NO, TNFα, IL-1, IL-2, IL-6 and COX-2) in response to e.g. LPS and cytokine stimulation. Activation of PPARγ is anti-inflammatory (Oates et al. 2002) and appears to exert a vasculoprotective effect by limiting endothelial dysfunction, impairing atherogenesis and preventing restenosis, while simultaneously and favourably modulating adipokine expression and lipid metabolism (Verma and Sztnitko 2006). Accumulating evidence suggests that PPAR agonists possess powerful anti-atherosclerotic properties, by both directly affecting the vascular wall and indirectly affecting systemic inflammation and insulin sensitivity. PPAR agonists are also used to treat metabolic syndrome, dyslipidaemia, insulin-resistance and diabetes (Meerarani et al. 2006).

Methods

Human HEK293 cells, stably transfected with the PPARγ ligand binding domain fused with the DNA binding domain of the GAL4 protein (GAL4-PPARγ fusion protein), produce beta-lactamase when incubated with PPARγ ligands. Transfected human kidney embryonic cells (Invitrogen Inc., Carlsbad, Calif.) were seeded onto matrigel in 96-well plates and allowed to attach overnight. The following day, vehicle alone (DMSO) or test compound at 1, 5 and 10 μM was added at varying concentrations to cells and incubated for 16-18 hours. Cells were then loaded with a FRET-based fluorescent substrate to assess beta-lactamase activity. Cells were protected from light, and incubated at room temperature for 2 h. Plates were read on a fluorescence plate reader with an excitation wavelength of 409 nm and emission wavelengths of 460 nm and 530 nm. Results were expressed as a ratio of these two wavelengths after the background (cell-free control wells) had been subtracted. PPARγ activity was thus determined by measuring beta-lactamase activity as assessed by a fluorescent product to substrate ratio.

Results

PPARγ activation is determined by an increase in beta-lactamase activity over that seen with media only control. This occurred with Compounds (1), (2), (6), (7), (18), (20), (22), (23), (27) and (29), suggesting that these compounds have PPARγ agonist activity. Data are presented in FIG. 13.

The compounds of the invention are demonstrative as being PPARγ agonists. That is, they are shown to exhibit metabolic syndrome, insulin resistance, diabetes, dyslipidaemia and related activities.

9.0 Cytotoxicity

9.1 Anti-Cancer Activity

Methods

The human pancreatic cancer cell line, HPAC (CRL-2119) was routinely cultured in 1:1 mixture DMEM (Sigma) plus Ham's F12 (Sigma) medium containing HEPES (15 mM), insulin (0.002 mg/ml), transferrin (0.005 mg/ml), hydrocortisone, (40 ng/ml), epidermal growth factor (10 ng/ml). The ovarian cancer cell lines; CP70 was obtained as a gift from Dr. Gil Mor (Yale University) and cultured in a 1:1 mixture DMEM plus Ham's F12 medium. The breast cancer cell line MDA-MB-468 cultured in Leibovitz's L-15 medium. The melanoma cell line MM200 was obtained as a gift from Peter Hersey (University of Newcastle) and cultured in DMEM medium. The large cell lung cancer cell line NCI-H460 was cultured in RPMI 1640 medium additionally supplemented with 4.5 g/L glucose and buffered with 10 mM HEPES. The colon adenocarcinoma cell line HT-29 was cultured in McCoy's 5a medium. All cultures were supplemented with 10% FCS(CSL, Australia), penicillin (100 μm % streptomycin (100 mg/ml), L-glutamine (2 mM) and sodium bicarbonate (1.2 g/L), and cultured at 37° C. in a humidified atmosphere of 5% $CO_2$. All cell lines were purchased from ATCC (Maryland, USA) except where noted.

$IC_{50}$ values were determined for each cell line. Cells were seeded in 96-well plates at an appropriate cell density as determined from growth kinetics analysis and cultured for 5 days in the absence and presence of the test compounds. Cell proliferation was assessed after the addition of 20 μl of 3-4,5 dimethylthiazol-2,5-diphenyl tetrazolium bromide (MTT, 2.5 mg/ml in PBS, Sigma) for 3-4 hrs at 37° C. according to manufacturer's instructions. $IC_{50}$ values were calculated from semi-log plots of % of control proliferation on the y-axis against log dose on the x-axis.

Results

Both compound (1) and compound (2) exhibited activity against all cancer cell lines tested ($IC_{50}$ of ~5-20 μM). Although not tested against all cancer cell lines, compounds (6), (15), (17), (24) were active against CP70, HPAC and MM200 cell lines. Compounds (16) and (17) displayed the most potent activity against the respective cell lines tested (~1-5 μM). Where tested, compound (9) also exhibited moderate toxicity against cancer cells. Compound (3) was selectively toxic to the MM200 melanoma cell line.

TABLE 11

Activity of test compounds against various cell lines representative of different cancer indications.

| | Indication (IC$_{50}$ µM) Cancer | | | | | |
|---|---|---|---|---|---|---|
| Compound | CP70 Ovarian | HPAC Pancreatic | HT29 Colorectal | MDA-MB-468 Breast | MM200 Melanoma | NCI-H460 Lung (NSCLC) |
| 1 | 5.51 ± 2.6 | 18.2 ± 8.1 | 20.6 ± 2.1 | 5.25 ± 2.1 | 6.10 ± 1.6 | 4.61 |
| 2 | 8.10 ± 3.0 | 18.3 ± 11 | 11.8 ± 0.7 | 4.87 ± 2.6 | 4.76 ± 1.3 | 8.77 ± 3.7 |
| 3 | 30.7 ± 22 | 32.23 | NT | NT | 8.9 ± 0.1 | NT |
| 6 | 5.08 ± 1.5 | 9.64 ± 3.6 | NT | NT | 11.3 ± 0.2 | NT |
| 7 | 9.98 ± 0.5 | 48.79 | NT | NT | 36.3 ± 6 | NT |
| 15 | 4.41 | 7.89 | NT | NT | 9.4 ± 1.5 | NT |
| 16 | NT | 3.88 | NT | NT | 1.8 | NT |
| 17 | 4.5 | 5.3 | NT | NT | 2.3 | NT |
| 24 | 8.6 | 6.83 | NT | NT | 14.6 | NT |
| 27 | 10.9 ± 1.5 | 12.4 ± 4.0 | 50.8 ± 1.0 | 14.9 ± 1.0 | 23.2 ± 1.1 | 17.8 ± 1.1 |

9.2 Toxicity to Normal Cells

Method

The neonatal foreskin fibroblasts (NFF) were a gift from Dr. Peter Parsons (Queensland Institute of Medical Research). Rabbit kidney (RK-13) cells were obtained from Miller Whalley (Macquarie University). Both cell lines were cultured in RPMI supplemented with 10% FCS(CSL, Australia), penicillin (100 U/ml), streptomycin (100 mg/ml), L-glutamine (2 mM) and sodium bicarbonate (1.2 g/L), and cultured at 37° C. in a humidified atmosphere of 5% $CO_2$. IC$_{50}$ values were determined as described above.

Results

The compounds exhibit from low to moderate toxicity against selected normal, non-transformed cells. Compound (1) showed some toxicity to a normal fibroblast cell line (~15 µM) whilst compound (2) was far less toxic to the NFFs and RK-13 cells (IC$_{50}$>30 µM).

TABLE 12

Activity of test compounds against normal, non-transformed cells.

| | Indication (IC$_{50}$ µM) | |
|---|---|---|
| Compound | NFF Fibroblast | RK Rabbit Kidney |
| 1 | 15.1 | NT |
| 2 | 33.2 | 53.26 |
| 3 | 56.2 ± 12.6 | 4.8 |
| 7 | 48.8 ± 12.2 | 56.6 |
| 17 | 55.9 | 5.5 |
| 27 | 40.3 ± 1.2 | 14.5 ± 1.0 |

10.0 Drug-Muting Stents

Method

A drug delivery stent having an expanded size of about 3 mm×17 mm is loaded with compound (1) in the following manner. The stent is positioned on a mandrel and a fast degrading barrier layer is deposited into the openings in the stent. The barrier layer is low molecular weight PLGA provided on the luminal side to seal the luminal side of the stent opening during filling. The layers described herein are deposited in a dropwise manner and are delivered in liquid form by use of a suitable organic solvent, such as DMSO, NMP, or DMAc. A plurality of layers of compound (1) and low molecular weight PLGA matrix are then deposited into the openings to form an inlay of drug for the reduction of ischemic injury. The compound (1) and polymer matrix are combined and deposited in a manner to achieve a desired drug delivery profile. A cap layer of low molecular weight PLGA, a fast degrading polymer, is deposited over the active agent layers protect the active agent during storage, transport, and delivery to the implantation site. The degradation rate of the cap layer is selected so that the agent is delivered relatively quickly after implantation. The total dosage on the stent is about 10 to about 600 micrograms, and may be more as appropriate. Persons skilled in the art will be able to determine other suitable dosages depending on the active agents used and the desired therapeutic effect.

In a similar method, a drug eluting stents are formed with oxazinyl compounds (2), (3), (7), (8), (16), (17), (18), (19) and (20).

In another method, multi layer drug eluting stents are formed with compound (1) and sirolimus. In yet another method, multi layer drug eluting stents are formed with compound (1) and paclitaxel. In still another method, multi layer drug eluting stents are formed with compound (1) and dehydroequol.

The release profiles of these stents are observed ex vivo by using the Armstrong human saphenous vein model. Coated stents are delivered into the veins, expanded by balloon catheter, and bathed in culture medium. The leaching of the active agent is observed over time by analysis of the culture medium to determine the release profile of the particular stent and polymer/drug matrix coating.

11.0 Comparative Examples

The biological activity of oxazinyl isoflavonoid compounds of the invention were assessed in a number of studies against isoflavonoid compounds genistein and 3',7-dihydroxy-isoflav-3-ene (37-DHE).

11.1 Effect on Apoptosis in Vascular Smooth Muscle Cells

Apoptosis (programmed cell death) plays a critical role in the health and disease of vascular tissue. It is a mode of cell death that occurs under normal physiological conditions where the cell is an active participant in its own demise ('cellular suicide'). Apoptosis is characterised by cytoplasmic shrinkage, nuclear condensation, and DNA fragmentation (Jacobson et al. 1997). It is now evident that the balance between changes in the regulation of VSMC growth and death is an important determinant of vascular integrity and lesion formation (Wang et al. 1999). Induction of VSMC apoptosis is therefore an important therapeutic strategy for the treatment of neointimal proliferative disease, including stent restenosis.

Methods

Activation of the caspase cascade is an integral event in the apoptotic pathway. Caspase-3 is one of the important "executioner" caspase enzymes, triggering the cleavage of numerous proteins that lead to the ordered breakdown of cells. The detection of caspase-3 activation is frequently used as a positive marker for apoptosis. A homogeneous luminescent caspase-3/7 assay, the Caspase-Glo™ 3/7 Assay (Promega Corp.) was used to provide an extremely sensitive measure of caspase activation. VSMC were incubated with different concentrations (0 [vehicle alone], 10, 50 and 100 µM) of test compounds. The assay used a proluminescent substrate containing the DEVD sequence recognized by caspase-3 and -7. The caspase-Glo™ 3/7 Reagent produced luminescence that is directly proportional to the amount of caspase-3/7 activity. The luminescence is linear over four orders of magnitude of caspase concentration and over a broad range of cell densities.

Figure 14:
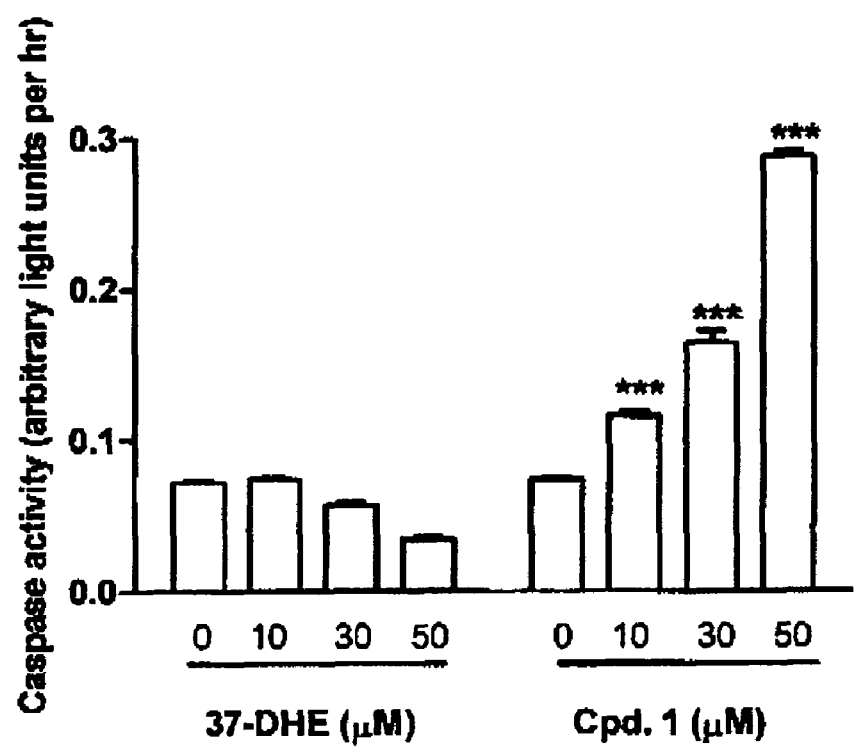
FIG. 14 compares the effect of test compounds on caspase-3/7 activity in rat A7r5 aortic smooth muscle cells.

Results in the A7r5 rat aortic SMC cell line, Compound (1) consistently induced apoptosis, as evidenced by induction of caspase-3/7 activity. Compound 37-DHE had no activity in this assay. Data are presented in FIG. 14.

Genistein was not examined in these assays and there no reports in the literature of genistein inducing apoptosis in vascular smooth muscle cells that could be sourced.

11.2 Human Umbilical Vein Smooth Muscle Cells

Methods

The effect of test compounds on human umbilical vein smooth muscle cells (HUVSMC), was examined. Cells, tissue explants from a male neonate (HRI—passage 2), were seeded into 96 well plates at $1 \times 10^3$ cells per well, and allowed to attach for 24 hours. They were then washed twice and incubated in medium without foetal calf serum (FCS) for 24-48 hours to serum-starve them. Test compounds were prepared in medium without FCS and added to the plates and incubated for one hour. Medium with FCS was added to give a final concentration of 10% and the plates incubated for 4-5 days until the controls were just confluent.

Results

Figure 15A:
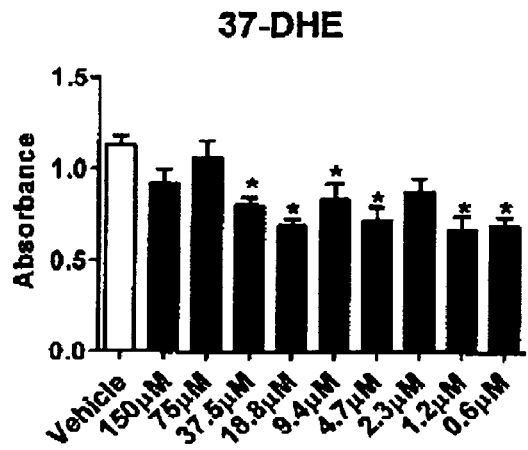
FIGS. 15a, 15b and 15c compare the effect of test compounds on the proliferation of HUVSMC.
Figure 15B:
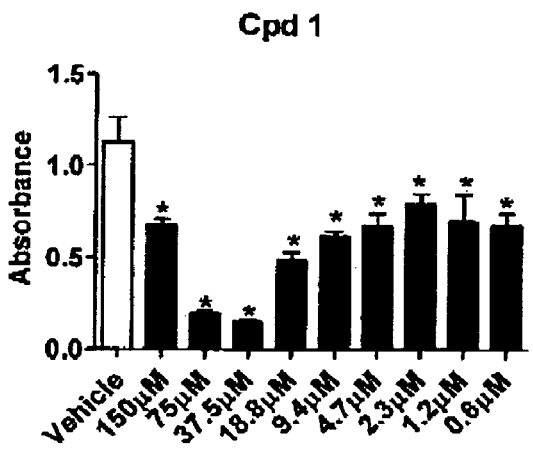
Figure 15C:
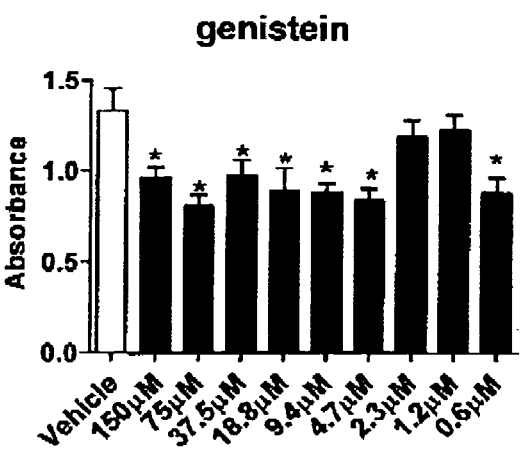

Compound (1) was more effective than either 37-DHE or genistein (which had similar activity) at inhibiting the proliferation of HUVSMC. The average $IC_{50}$ of Compound (1) over three different assays was 15 µM. Data are presented in FIG. 15.

11.3 Rat Aortic Smooth Muscle Cell Lines

The effect of test compounds on rat aortic smooth muscle cell line (A7r5) and another cell line from the media of rat aorta (A10) was examined. The methodology was the same as for HUVSMC, except that the cells were treated with compound for three days.

Results

Figure 16A:
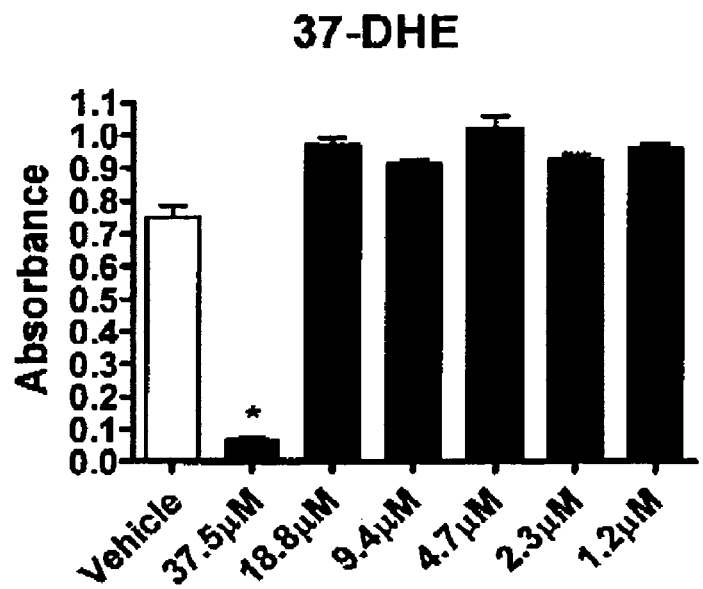
FIGS. 16a and 16b compare the effect of test compounds on the proliferation of A7r5 rat aortic smooth muscle cells.
Figure 16B:
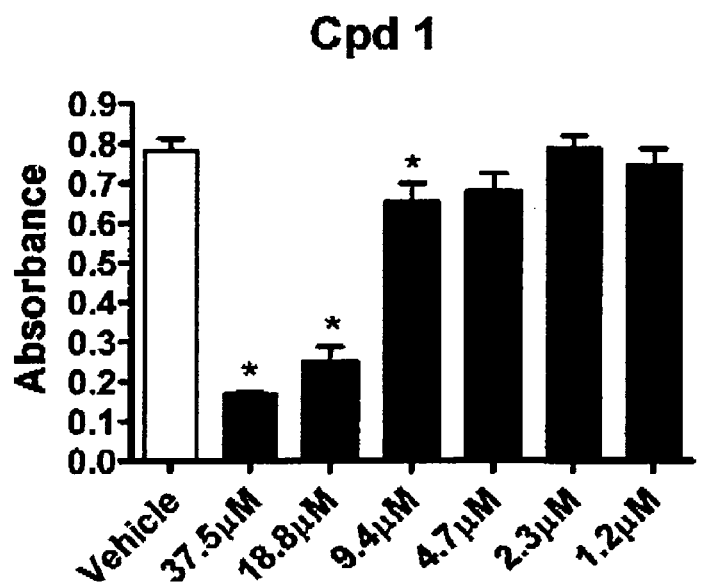
Figure 17A:
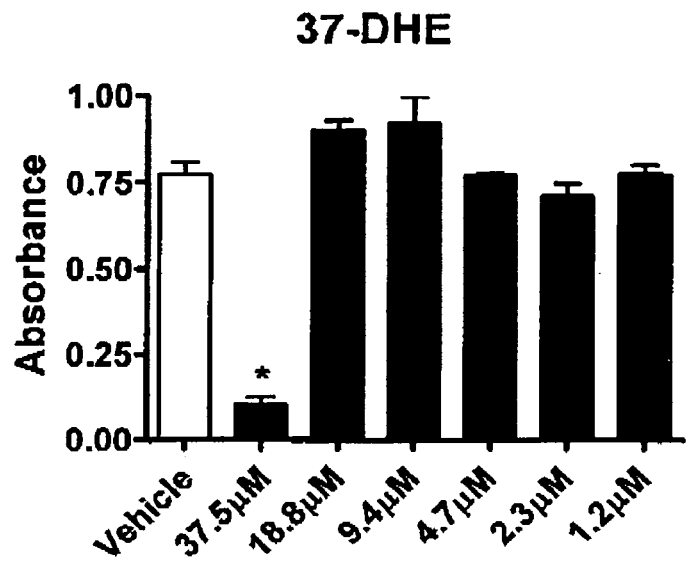
FIGS. 17a and 17b compare the effect of test compounds on the proliferation of A10 smooth muscle cells from the media of rat aorta.
Figure 17B:
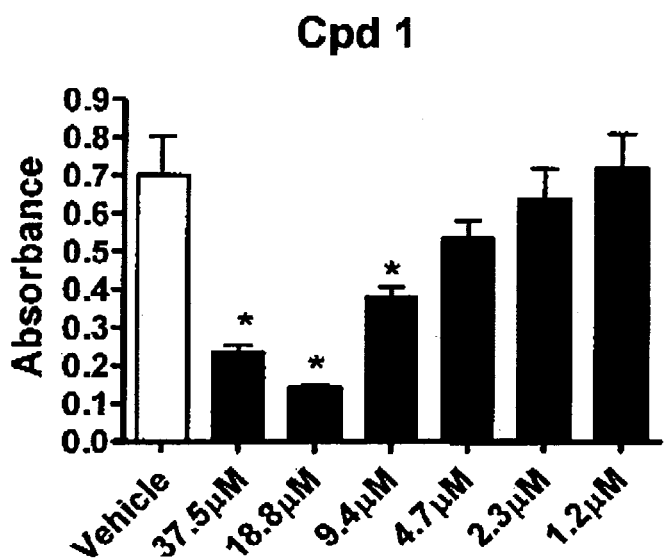

Compound (1) and 37-DHE were effective at inhibiting proliferation, with Compound (1) being more potent. The $IC_{50}$s in A7r5 cells were 23 µM and 45 µM respectively, and in A10 cells, 11 µM and 31 µM respectively. Genistein was not examined. Data are presented in FIGS. 16 and 17.

11.4 Effect on Adhesion Molecule Expression in Arterial Cells

Restenosis involves the recruitment of inflammatory cells from the circulation and their transendothelial migration. This process is predominantly mediated by cellular adhesion molecules, which are expressed on the vascular endothelium and on circulating leukocytes in response to several inflammatory stimuli. Selectins (P, E and L) are involved in the rolling and tethering of leukocytes on the vascular wall. Intercellular adhesion molecules (ICAMs) and vascular cell adhesion molecules (VCAM-1), as well as some of the integrins, induce firm adhesion of inflammatory cells at the vascular surface. VCAM-1 expression is restricted to lesions and lesion-predisposed regions whilst ICAM-1 expression is broader and extends into uninvolved aorta and lesion-protected regions. Increased adhesion molecule expression plays a part in restenosis. In a prospective study of 46 patients who underwent elective percutaneous transluminal coronary angioplasty (PCTA), those with coronary restenosis at 6-months follow-up showed a significant increase in adhesion molecules on the surface of their circulating monocytes, compared with patients without restenosis (Navarro-Lopez et al. 2003).

Methods

Human arterial endothelial cells (HAECs) in growth medium (Cell Applications Inc) were seeded into 96-well plates at a density of 10,000 cells per well. Plates were incubated overnight at 37° C. to achieve confluence. TNFα (10 µl, 2 ng/ml) was added to each well, which contained 100 µl of medium, after which compounds at 10 and 30 µM were added. All samples were measured in quadruplicate (4 wells per treatment).

After incubation with compound for 4 hrs, medium was removed and cells were probed with either non-specific IgG or specific mouse antibodies against VCAM, ICAM or E-selectin (BD Biosciences). Plates were allowed to stand for 30 minutes—monolayers were then washed, and sheep anti-mouse antibody/horseradish peroxidase conjugate (1:500 in 100 µL HBSS with 10% heat-inactivated human serum and 0.05% Tweet 20) was added and left for 30 minutes. After further washing, 150 µL ABTS substrate (Kirkegaard and Perry Laboratories) was added to each well and allowed to develop for 15 minutes. Optical density was measured at 405 nm with an ELISA reader (Titertek Multiscan, Flow Laboratories).

Results

At 100 µM, test compounds significantly affected HAEC viability. For some compounds, HAEC viability was less than 80% at 30 µM. It was thus found that 10 µM was the most appropriate concentration for comparing the activity of compounds in this assay.

Figure 18A:
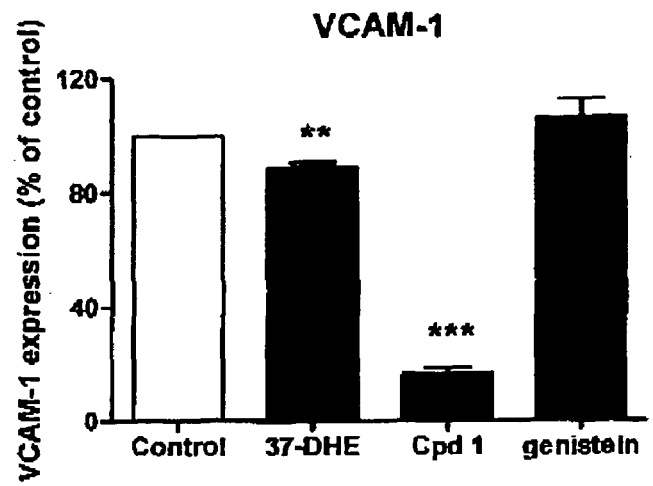
FIGS. 18a, 18b and 18c compare the effect of test compounds on the expression of VCAM-1, ICAM-1 and E-selectin respectively.
Figure 18B:
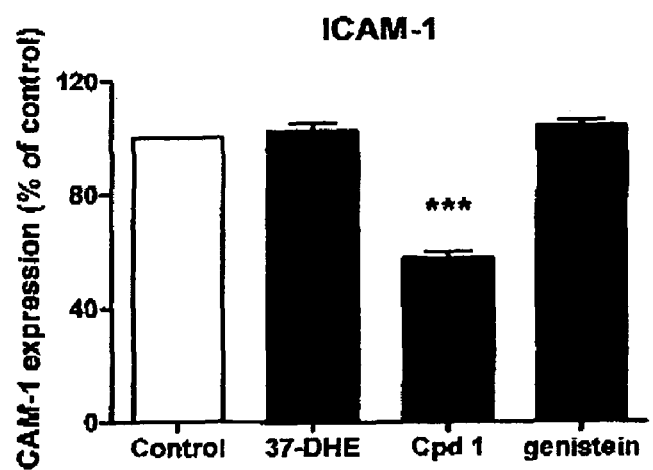
Figure 18C:
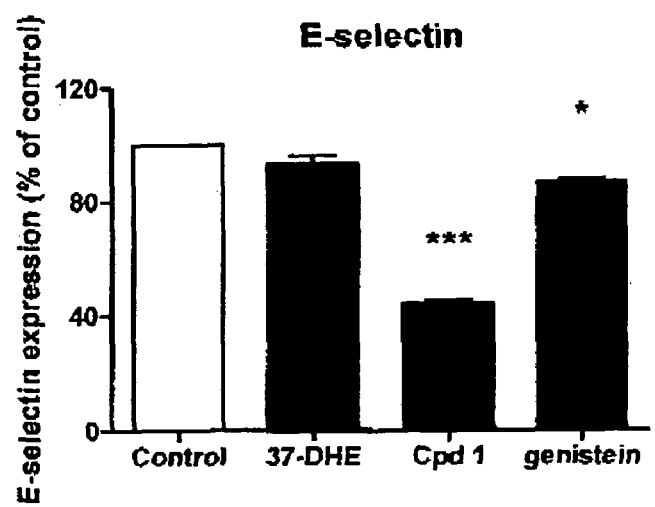
Figure 19:
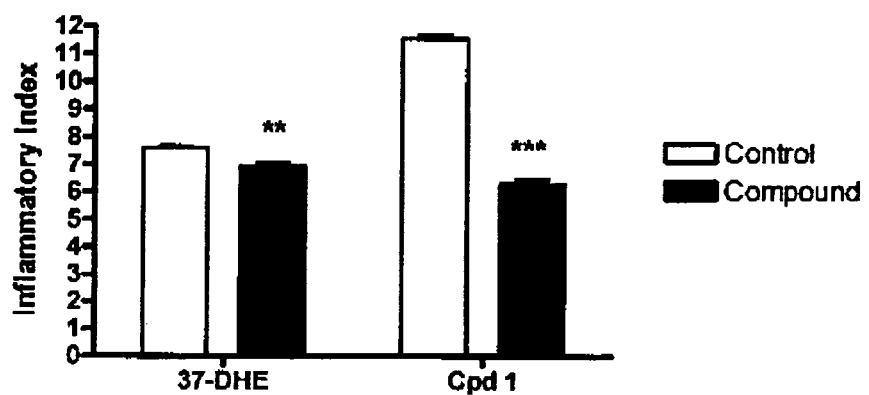
FIG. 19 compares the effect of test compounds at 30 μM on NFκB-promoter activity in TNFa-stimulated THP-1 monocyte/macrophages.

Compound (1) markedly inhibited VCAM expression, as well as E-selectin expression by in excess of 50%. Its effect on ICAM expression was between 10-50% inhibition. The effect of 37-DHE was less pronounced, and similar to that of genistein. Data are presented in FIG. 18.

11.5 Effect on NFκB Production

Methods

This comparative study was conducted according to the assay method set out in the example at Section 2.4 above.

Results

It was found that 30 µM was the optimal concentration at which to compare the NFκB-inhibitory activity of test compounds. At 50 µM and 100 µM, compounds reduced cell viability.

Figure 20:
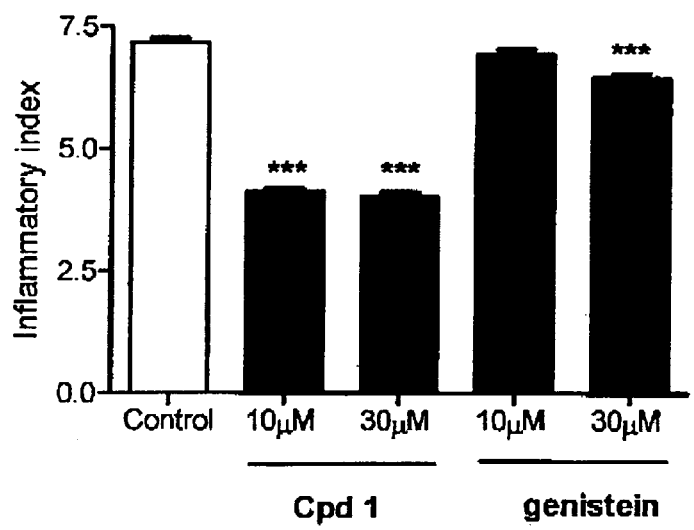
FIG. 20 compares the effect of test compounds on NFκB-promoter activity in TNFa-stimulated THP-1 monocyte/macrophages.
Figure 21:
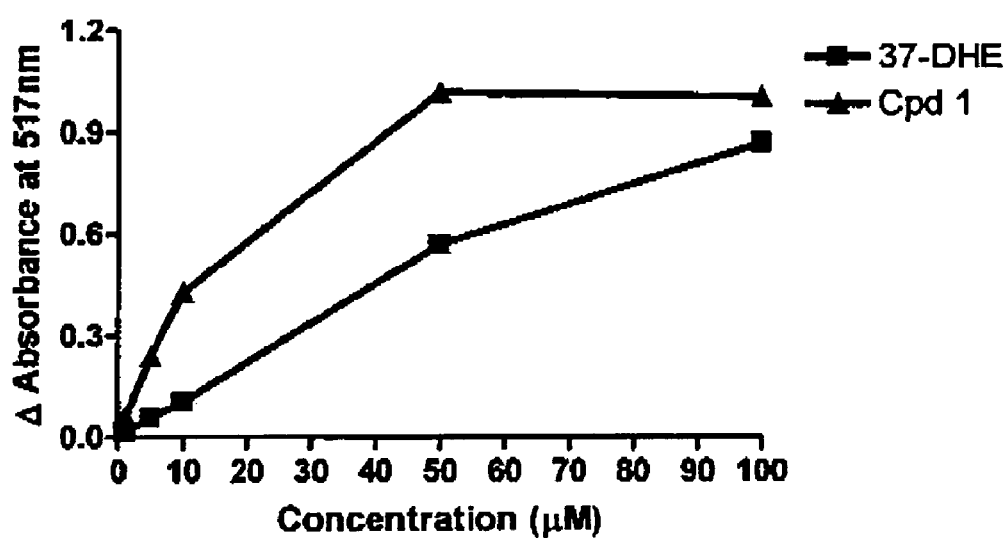
FIG. 21 compares the activity of test compounds as free radical scavengers with 2,2-diphenyl-1-picrylhidrazyl (DPPH).

Compound (1), 37-DHE and genistein all inhibited NFκB. Compound (1) did so more potently than either 37-DHE or genistein. Compound (1) was also compared with genistein at 10 µM and 30 µM in one assay. Data is shown in FIGS. 39 and 20.

11.6 Effect on Free Radical Scavenging

The antioxidant (free radical trapping) activity of test compounds was assessed using the stable free radical compound 2,2-diphenyl-1-picrylhydrazyl (DPPH). A stock solution of DPPH was prepared at a concentration of 0.1 µM in ethanol and mixed for 10 minutes prior to use. Initial screening of test compound at a concentration of 100 µM was reacted with DPPH for 20 minutes, after which time the absorbance at 517 nm was determined. The change in absorbance was compared to a reagent blank (DPPH with ethanol alone). 37-DHE and Compound (1), but not genistein, were found to have free radical scavenging activity (Δbs>0.3) at 100 µM and a dose response curve was produced. The $IC_{50}$ value was estimated as the concentration of test compound that causes a 0.6 change in absorbance (with 1.2 absorbance units representing total scavenging of the DPPH radical).

Genistein had no antioxidant activity in this assay, and was not tested at concentrations lower than 100 µM. However, both Compound (1) and 37-DHE and Compound (1) demonstrated potent free radical scavenging ability (see Table 13).

TABLE 13

Free radical scavenging ability of test compounds - $EC_{50}$ (µM)

| Compound | $EC_{50}$ (µM) |
| --- | --- |
| 37-DHE | 55 |
| Cpd. (1) | 19 |
| genistein | >100 µM |

11.7 Effect on Peroxyl Radical-Induced Red Blood Cell (RBC) Lysis

Methods

This comparative study was conducted according to the assay method set out in the example at Section 3.3 above.

Results

Both compound (1) and 37-DHE, as well as genistein demonstrated antioxidant activity by delaying the AAPH-induced time to half-lysis of red blood cells. Compound (1) was the most active free radical scavenger as evidenced by the greater delay to reach half-lysis absorbance (see Table 14).

TABLE 14

Time taken to reach half-lysis following incubation with test compounds at 10 µM (min)

| Compound | time (min) |
| --- | --- |
| vehicle | 40.0 |
| 37-DHE | 126.6 |
| Cpd. (1) | 141.6 |
| genistein | 93.8 |

The invention has been described herein, with reference to certain preferred embodiments, in order to enable the reader to practice the invention without undue experimentation. However, a person having ordinary skill in the art will readily recognise that many of the components and parameters may be varied or modified to a certain extent without departing from the scope of the invention. Furthermore, titles, headings, or the like are provided to enhance the reader's comprehension of this document, and should not be read as limiting the scope of the present invention.

The entire disclosures of all applications, patents and publications, cited herein, if any, are hereby incorporated by reference.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification individually or collectively, and any and all combinations of any two or more of said steps or features.

The reference to any prior art in this specification is not, and should not be taken as, an acknowledgment or any form of suggestion that that prior art forms part of the common general knowledge in the field of endeavour.

SELECTED REFERENCE ARTICLES

Alexandre-Moreira, M. S., et al. (1999). "Studies on the anti-inflammatory and analgesic activity of Curatella americana L." Journal of Ethnopharmacology 67(2): 171-7.

Amar, J., J. Fauvel, et al. (2006). "Interleukin 6 is associated with subclinical atherosclerosis: a link with soluble intercellular adhesion molecule 1." J Hypertens 24(6): 1083-8.

Ashendel, C. L. and R. K. Boutwell (1979). "Prostaglandin E and F levels in mouse epidermis are increased by tumor-promoting phorbol esters." Biochem Biophys Res Commun 90(2): 623-7.

Bennett, J. V., et al. (1966). "Simplified, accurate method for antibiotic assay of clinical specimens." Appl Microbiol 14(2): 170-7.

Bermejo, B. P., et al. (1998) "In vivo and in vitro antiinflammatory activity of saikosaponins." Life Sciences 63(13): 1147-56.

Chang, J., et al. (1986). "Correlation between mouse skin inflammation induced by arachidonic acid and eicosanoid synthesis." Inflammation 10(3): 205-14.

Chin-Dusting, J. P., et al. (2001). "The vascular activity of some isoflavone metabolites: implications for a cardioprotective role." British Journal of Pharmacology. 133(4): 595-605.

Demasi, M., et al. (2000). "Assay of cyclooxygenase-1 and 2 in human monocytes." Inflammation Research 49(12): 737-43.

Demasi, M., et al. (2003). "Effects of hypoxia on monocyte inflammatory mediator production: Dissociation between changes in cyclooxygenase-2 expression and eicosanoid synthesis." Journal of Biological Chemistry 278(40): 38607-16.

Erbel, R., C. Di Mario, et al. (2007). "Temporary scaffolding of coronary arteries with bioabsorbable magnesium stents: a prospective, non-randomised multicentre trial." Lancet 369(9576): 1869-75.

Fuke, S., K. Maekawa, et al. (2007). "Impaired endothelial vasomotor function after sirolimus-eluting stent implantation." Circ J 71(2): 220-5.

Funayania, H., S. E. Ishikawa, et al. (2006). "Close association of regional interleukin-6 levels in the infarct-related culprit coronary artery with restenosis in acute myocardial infarction." Circ J 70(4): 426-9.

Getz, G. S. (2005). "Thematic review series: the immune system and atherogenesis. Immune function in atherogenesis." 3 Lipid Res 46(1): 1-10.

Jacobson, M. D., M. Weil, et al. (1997). "Programmed cell death in animal development." Cell 88(3): 347-54.

Hansson, G. K., P. Libby, et al. (2002). "Innate and adaptive immunity in the pathogenesis of atherosclerosis." Circ Res 91(4): 281-91.

Hansson, G. K. and P. Libby (2006). "The immune response in atherosclerosis: a double-edged sword." Nat Rev Immunol 6(7): 508-519.

Hofma, S. H., W. J. van der Giessen, et al. (2006). "Indication of long-term endothelial dysfunction after sirolimus-eluting stent implantation." Eur Heart J 27(2): 166-70.

Hojo, Y., U. Ikeda, et al. (2000). "Interleukin 6 expression in coronary circulation after coronary angioplasty as a risk factor for restenosis." Heart 84(1): 83-7.

Kuchera, S., et al. (1993). "Anti-inflammatory properties of the protein kinase C inhibitor, 3-[1-[3-(dimethylamino) propyl]-1H-indol-3-yl]-4-(1H-indol-3-yl)-1H-pyrrole-2, 5-dione monohydrochloride (GF109203X) in the PMA-mouse ear edema model." Agents & Actions 39(Spec No): C169-73.

Libby, P. and P. Ganz (1997). "Restenosis revisited—new targets, new therapies." N Engl J Med 337(6): 418-9.

McNamara, C. A., I. J. Sarembock, et al. (1996). "Thrombin and vascular smooth muscle cell proliferation: implications for atherosclerosis and restenosis." Seminars in Thrombosis & Hemostasis 22(2): 139-44.

Meerarani, P., J. J. Badimon, et al. (2006). "Metabolic syndrome and diabetic atherothrombosis: implications in vascular complications." Curr Mol Med 6(5): 501-14.

Nabel, E. G. (1991). "Biology of the impaired endothelium." Am J Cardiol 68(12): 6C-8C.

Navarro-Lopez, F., A. Francino, et al. (2003). "[Late T-lymphocyte and monocyte activation in coronary restenosis. Evidence for a persistent inflammatory/immune mechanism?]." Rev Esp Cardiol 56(5): 465-72.

Oates, J. C., C. M. Reilly, et al. (2002). "Peroxisome proliferator-activated receptor gamma agonists: potential use for treating chronic inflammatory diseases." Arthritis & Rheumatism. 46(3): 598-605.

Opas, E. E., et al. (1985). "Prostaglandin and leukotriene synthesis in mouse ears inflamed by arachidonic acid." Journal of Investigative Dermatology 84(4): 253-6.

Ormiston, J. A., M. W. Webster, et al. (2007). "First-in-human implantation of a fully bioabsorbable drug-eluting stent: the BVS poly-L-lactic acid everolimus-eluting coronary stent." Catheter Cardiovasc Interv 69(1): 128-31.

Patti, G., R. Melfi, et al. (2005). "[The role of endothelial dysfunction in the pathogenesis and in clinical practice of atherosclerosis. Current evidences]." Recenti Prog Med 96(10): 499-507.

Rivard, A. and V. Andres (2000). "Vascular smooth muscle cell proliferation in the pathogenesis of atherosclerotic cardiovascular diseases." Histology & Histopathology 15(2): 557-71.

Rosenson, R. S. (2004). "Stains in atherosclerosis: lipid-lowering agents with antioxidant capabilities. [see comment]." Atherosclerosis 173(1): 1-12.

Schiele, T. M. (2005). "Current understanding of coronary in-stent restenosis. Pathophysiology, clinical presentation, diagnostic work-up, and management" Z Kardiol 94(11): 772-90.

Schober, A. and C. Weber (2005). "Mechanisms of monocyte recruitment in vascular repair after injury." Antioxid Redox Signal 7(9-10): 1249-57.

Silvan, A. M., et al. (1996). "Inhibition by hydroxyachillin, sesquiterpene lactone from Tanacetum microphyllum, of PMA-induced mouse ear oedema." Inflammation Research 45(6): 289-92.

Tardif, J. C., J. Gregoire, et al. (2002). "Prevention of restenosis with antioxidants: mechanisms and implications." Am J Cardiovasc Drugs 2(5): 323-34.

Tardif, J. C. (2005). "Antioxidants and atherosclerosis: emerging drug therapies." Curr Atheroscler Rep 7(1): 71-7.

Vanderlaan, P. A. and C. A. Reardon (2005). "Thematic review series: the immune system and atherogenesis. The unusual suspects: an overview of the minor leukocyte populations in atherosclerosis." J Lipid Res 46(5): 829-38.

Verma, S, and P. E. Szmitko (2006). "The vascular biology of peroxisome proliferator-activated receptors: Modulation of atherosclerosis." *Can J Cardiol* 22 Suppl B: 12B-7B.

Wang, B. Y., H. K. Ho, et al. (1999). "Regression of atherosclerosis: role of nitric oxide and apoptosis." Circulation 99(9): 1236-41.

Weber, C. and W. Erl (2000). "Modulation of vascular cell activation, function, and apoptosis: role of antioxidants and nuclear factor-kappa B." Curr Top Cell Regul 36: 217-35.

Young, J. M., et al. (1984). "The mouse ear inflammatory response to topical arachidonic acid." Journal of Investigative Dermatology. 82(4): 367-71.

The invention claimed is:

1. An oxazinyl isoflavonoid compound of the general formula (I):

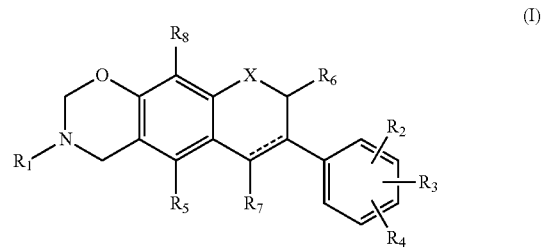

wherein $R_1$ is alkyl, cycloalkyl, arylalkyl, alkenyl, alkynyl, aryl or alkylaryl, $R_2$, $R_3$ and $R_4$ are independently hydrogen, hydroxy, $OR_9$, $OC(O)R_9$, $OSi(R_{10})_3$, alkyl, cycloalkyl, aryl, arylalkyl, thiol, alkylthio, nitro, cyano or halo, $R_5$ is hydrogen, alkyl, cycloalkyl, aryl, arylalkyl, nitro, cyano or halo, $R_6$ is hydrogen, alkyl, cycloalkyl, aryl, arylalkyl, nitro, cyano or halo, $R_7$ is hydrogen, alkyl, cycloalkyl, aryl or arylalkyl, $R_8$ is hydrogen, alkyl, cycloalkyl, aryl, arylalkyl, nitro, cyano or halo, $R_9$ is alkyl, aryl or arylalkyl, $R_{10}$ is independently alkyl or aryl, X is O, $N_{12}$ where $R_{12}$ is alkyl, aryl or arylalkyl, or S, and the drawing "---" represents either a single bond or a double bond, which hydrocarbon substituents can be optionally substituted by one or more of alkyl, halo, acyloxy, hydroxy, alkoxy, silyloxy, nitro and cyano, and which compounds include pharmaceutically acceptable salts thereof.

2. An oxazinyl isoflavonoid compound of claim 1 of the formula (I-I):

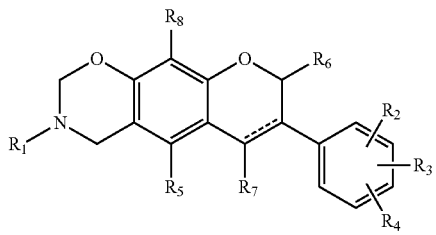

wherein
$R_1$ is alkyl, cycloalkyl, arylalkyl, alkenyl, alkynyl, aryl or alkylaryl,
$R_2$, $R_3$ and $R_4$ are independently hydrogen, hydroxy, $OR_9$, $OC(O)R_9$, $OSi(R_{10})_3$, alkyl, cycloalkyl, aryl, arylalkyl, thiol, alkylthio, nitro, cyano or halo,
$R_5$ is hydrogen, alkyl, cycloalkyl, aryl, arylalkyl, nitro, cyano or halo,
$R_6$ is hydrogen, alkyl, cycloalkyl, aryl, arylalkyl, nitro, cyano or halo,
$R_7$ is hydrogen, alkyl, cycloalkyl, aryl or arylalkyl,
$R_8$ is hydrogen, alkyl, cycloalkyl, aryl, arylalkyl, nitro, cyano or halo,
$R_9$ is alkyl, aryl or arylalkyl,
$R_{10}$ is independently alkyl or aryl, and
the drawing "═" represents either a single bond or a double bond,
which hydrocarbon substituents can be optionally substituted by one or more of alkyl, halo, acyloxy, hydroxy, alkoxy, silyloxy, nitro and cyano, and which compounds include pharmaceutically acceptable salts thereof.

3. The oxazinyl isoflavonoid compound of claim 2 of the formula (I-II):

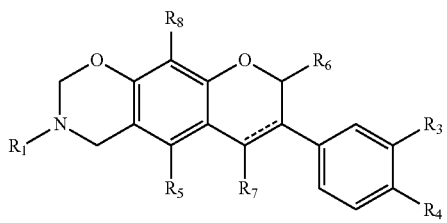

wherein
$R_1$ is alkyl, arylalkyl, aryl or alkylaryl,
$R_3$ and $R_4$ are independently hydrogen, hydroxy, $OR_9$, $OC(O)R_9$, $OSi(R_{10})_3$, alkyl, arylalkyl, nitro, cyano or halo,
$R_5$ is hydrogen, alkyl or halo,
$R_6$ is hydrogen or halo,
$R_7$ is hydrogen, alkyl or aryl,
$R_8$ is hydrogen, alkyl or halo,
$R_9$ is alkyl or arylalkyl,
$R_{10}$ is independently alkyl, and
the drawing "═" represents either a single bond or a double bond,
which hydrocarbon substituents can be optionally substituted by one or more of alkyl, halo, acyloxy, hydroxy, alkoxy, silyloxy, nitro and cyano, and which compounds include pharmaceutically acceptable salts thereof.

4. The oxazinyl isoflavonoid compound of claim 3, wherein
$R_1$ is alkyl, phenylalkyl, phenyl, naphthylalkyl, naphthyl or alkylphenyl,
$R_3$ and $R_4$ are independently hydrogen, hydroxy, $OR_9$, $OC(O)R_9$, alkyl, nitro, cyano or halo, and where at least one of $R_3$ and $R_4$ is not hydrogen,
$R_7$ is hydrogen or phenyl,
$R_9$ is alkyl, and
which hydrocarbon substituents can be optionally substituted by one or more of alkyl, halo, acyloxy, hydroxy, alkoxy, nitro and cyano.

5. The oxazinyl isoflavonoid compound of claim 4, wherein
$R_1$ is methyl, ethyl, propyl, isopropyl, butyl, phenylmethyl, 1-phenylethyl, phenyl, naphthylmethyl, naphthyl or alkylphenyl optionally substituted by alkyl, halo, hydroxy, acetyloxy, methoxy, ethoxy, nitro or cyano,
$R_3$ and $R_4$ are independently hydrogen, hydroxy and methoxy, and where at least one of $R_3$ and $R_4$ is not hydrogen,
$R_5$ is hydrogen, methyl or halo,
$R_6$ is hydrogen, methyl or ethyl,
$R_7$ is hydrogen or phenyl optionally substituted by alkyl, halo, hydroxy, methoxy, nitro or cyano, and
$R_8$ is hydrogen, methyl or halo.

6. The oxazinyl isoflavonoid compound of claim 5, wherein
$R_1$ is methyl, ethyl, propyl, phenylmethyl, 1-phenylethyl, phenyl, naphthylmethyl or methylphenyl optionally substituted by methyl, halo, hydroxy, methoxy, nitro or cyano,
$R_5$ is hydrogen,
$R_6$ is hydrogen,
$R_7$ is hydrogen or phenyl optionally substituted by methoxy, and
$R_8$ is hydrogen.

7. The oxazinyl isoflavonoid compound of claim 1, wherein $R_1$ is phenyl, phenylmethyl, 1-phenylethyl, naphth-1-yl, naphtha-1-ylmethyl, 4-methoxyphenylmethyl, 4-hydroxyphenyl, 4-cholorphenylmethyl, 4-methylphenyl, 4-cyanophenyl, 3-methylphenyl, 3-nitrophenyl, 4-tert-butylphenyl, 4-tert-butylphenylmethyl, 3,4-dimethylphenyl, 4-methoxyphenyl or 4-methoxyphenylmethyl.

8. The oxazinyl isoflavonoid compound of claim 1, wherein $R_1$ is methyl, propyl or 3-methoxypropyl.

9. The oxazinyl isoflavonoid compound of claim 1, wherein $R_3$ or $R_4$ is hydroxy.

10. The oxazinyl isoflavonoid compound of claim 1, wherein $R_3$ and $R_4$ are methoxy or hydroxy.

11. The oxazinyl isoflavonoid compound of claim 1, wherein $R_7$ is hydrogen or 4-methoxyphenyl.

12. The oxazinyl isoflavonoid compound of claim 1, wherein halo is chloro or bromo.

13. The oxazinyl isoflavonoid compound of claim 1, wherein the drawing "═" represents a double bond.

14. The oxazinyl isoflavonoid compound of claim 1 selected from compounds (1) to (32):
4-(3-Benzyl-2,3,4,8-tetrahydrochromeno[6,7-e][1,3]oxazin-7-yl)phenol (1);
4-(3-(1-Phenylethyl)-2,3,4,8-tetrahydrochromeno[6,7-e][1,3]oxazin-7-yl)phenol (2);
4-(3-Propyl-2,3,4,8-tetrahydrochromeno[6,7-e][1,3]oxazin-7-yl)phenol (3);
4-(3-methyl-2,3,4,8-tetrahydrochromeno[6,7-e][1,3]oxazin-7-yl)phenol (4);

7-(3,4-Dimethoxyphenyl)-3-propyl-2,3,4,8-tetrahydro-chromeno[6,7-e][1,3]oxazine (5);

4-(3-(4-Methoxybenzyl)-2,3,4,8-tetrahydrochromeno[6,7-e][1,3]oxazin-7-yl)phenol (6);

4-(3-Phenyl-2,3,4,8-tetrahydrochromeno[6,7-e][1,3]oxazin-7-yl)phenol (7);

4,4'-(Chromeno[6,7-e][1,3]oxazine-3,7 (2H,4H,8H)-diyl)diphenol (8);

7-(3,4-Dimethoxyphenyl)-3-(4-methoxybenzyl)-2,3,4,8-tetrahydrochromeno[6,7-e][1,3]oxazine (9);

3-(3-Benzyl-2,3,4,8-tetrahydrochromeno[6,7-e][1,3]oxazin-7-yl)phenol (10);

3-(3-Phenyl-2,3,4,8-tetrahydrochromeno[6,7-e][1,3]oxazin-7-yl)phenol (11);

7-(3,4-Dimethoxyphenyl)-3-phenyl-2,3,4,8-tetrahydro-chromeno[6,7-e][1,3]oxazine (12);

3-Benzyl-7-(3,4-dimethoxyphenyl)-10-methyl-2,3,4,8-tetrahydrochromeno[6,7-e][1,3]oxazine (13);

7-(3,4-Dimethoxyphenyl)-10-methyl-3-propyl-2,3,4,8-tetrahydrochromeno[6,7-e][1,3]oxazine (14);

4-(3-(4-Chlorobenzyl)-2,3,4,8-tetrahydrochromeno[6,7-e][1,3]oxazin-7-yl)phenol (15);

4-(3-(3-Methoxypropyl)-2,3,4,8-tetrahydrochromeno[6,7-e][1,3]oxazin-7-yl)phenol (16);

3-(3-(3-Methoxypropyl)-2,3,4,8-tetrahydrochromeno[6,7-e][1,3]oxazin-7-yl)phenol (17);

4-(3-p-Tolyl-2,3,4,8-tetrahydrochromeno[6,7-e][1,3]oxazin-7-yl)phenol (18);

7-(3,4-Dimethoxyphenyl)-10-methyl-3-p-tolyl-2,3,4,8-tetrahydrochromeno[6,7-e][1,3]oxazine (19);

3-p-Tolyl-2,3,4,8-tetrahydrochromeno[6,7-e][1,3]oxazin-7-yl)phenol (20);

4-(7-(3-Hydroxyphenyl)chromeno[6,7-e][1,3]oxazin-3 (2H,4H,8H)-yl)benzonitrile (21);

4-(3-m-Tolyl-2,3,4,8-tetrahydrochromeno[6,7-e][1,3]oxazin-7-yl)phenol (22);

4-(3-(3-Nitrophenyl)-2,3,4,8-tetrahydrochromeno[6,7-e][1,3]oxazin-7-yl)phenol (23);

4-(3-(4-Chlorobenzyl)-6-(4-methoxyphenyl)-2,3,4,8-tetrahydrochromeno[6,7-e][1,3]oxazin-7-yl)-phenol (24);

4-(10-Bromo-3-propyl-2,3,4,8-tetrahydrochromeno[6,7-e][1,3]oxazin-7-yl)phenol (25);

3,4'-(10-Methyl-chromeno[6,7-e][1,3]oxazine-3,7(2H,4H,8H)-diyl)diphenol (26);

4-(8-Ethyl-3-propyl-2,3,4,8-tetrahydrochromeno[6,7-e][1,3]oxazin-7-yl)phenol (27);

4-(3-(4-tert-Butylphenyl)-2,3,4,8-tetrahydrochromeno[6,7-e][1,3]oxazin-7-yl)phenol (28);

4-(3-(4-tert-Butylbenzyl)-2,3,4,8-tetrahydrochromeno[6,7-e][1,3]oxazin-7-yl)phenol (29);

4-(3-(Naphth-1-yl-methyl)-2,3,4,8-tetrahydrochromeno[6,7-e][1,3]oxazin-7-yl)phenol (30);

4-(3-(3,4-Dimethylphenyl)-2,3,4,8-tetrahydrochromeno[6,7-e][1,3]oxazin-7-yl)phenol (31);

4-(3-(4-Methoxyphenyl)-2,3,4,8-tetrahydrochromeno[6,7-e][1,3]oxazin-7-yl)phenol (32);

or a pharmaceutically acceptable salt thereof.

15. A process for the preparation of a compound of formula (I):

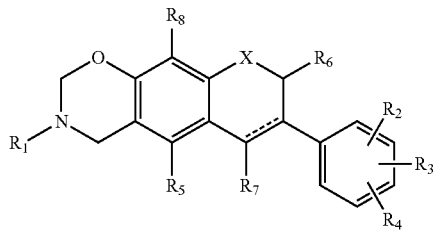

wherein $R_1$ is alkyl, cycloalkyl, arylalkyl, alkenyl, alkynyl, aryl or alkylaryl, $R_2$, $R_3$ and $R_4$ are independently hydrogen, hydroxy, $OR_9$, $OC(O)R_9$, $OSi(R_{10})_3$, alkyl, cycloalkyl, aryl, arylalkyl, thiol, alkylthio, nitro, cyano or halo, $R_5$ is hydrogen, alkyl, cycloalkyl, aryl, arylalkyl, nitro, cyano or halo, $R_6$ is hydrogen, alkyl, cycloalkyl, aryl, arylalkyl, nitro, cyano or halo, $R_7$ is hydrogen, alkyl, cycloalkyl, aryl or arylalkyl, $R_8$ is hydrogen, alkyl, cycloalkyl, aryl, arylalkyl, nitro, cyano or halo, $R_9$ is alkyl, aryl or arylalkyl, $R_{10}$ is independently alkyl or aryl, X is O, $N_{12}$ where $R_{12}$ is alkyl, aryl or arylalkyl, or S, and the drawing "---" represents either a single bond or a double bond, which hydrocarbon substituents can be optionally substituted by one or more of alkyl, halo, acyloxy, hydroxy, alkoxy, silyloxy, nitro and cyano, comprising the step of reacting an isoflavonoid compound of formula (II):

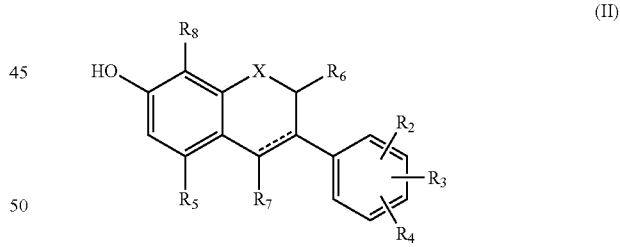

wherein $R_2$, $R_3$, $R_4$, $R_5$, $R_6$, $R_7$, $R_8$ and X are as defined above and the drawing "---" represents either a single bond or a double bond, with formaldehyde and a primary amine, $R_1$—$NH_2$, wherein $R_1$ is alkyl, cycloalkyl, arylalkyl, alkenyl, alkynyl, aryl or alkylaryl which can be optionally substituted, to form a compound of the general formula (I).

16. A pharmaceutical composition which comprises one or more compounds of formula (I) as defined in claim 1 in association with one or more pharmaceutical carriers, excipients, auxiliaries and/or diluents.

17. A pharmaceutical composition according to claim 16, wherein the agent is a cardioprotective, anti-inflammatory, anti-oxidant or chemotherapeutic agent.

18. An implantable medical device for delivering an active agent wherein said device comprises one or more compounds of formula (I) as defined in claim 1 optionally in association with one or more additional active agents.

19. An implantable medical device of claim 18, wherein the device is a stent.

20. The compound of claim 1, wherein the compound is 4-(3-Benzyl-2,3,4,8-tetrahydrochromeno[6,7-e][1,3]oxazin-7-yl)phenol (1).

21. The compound of claim 1, wherein the compound is 4-(3-(1-Phenylethyl)-2,3,4,8-tetrahydrochromeno[6,7-e][1,3]oxazin-7-yl)phenol (2).

* * * * *

UNITED STATES PATENT AND TRADEMARK OFFICE
CERTIFICATE OF CORRECTION

PATENT NO.        : 8,367,659 B2
APPLICATION NO. : 12/528208
DATED             : February 5, 2013
INVENTOR(S)       : Heaton et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 816 days.

Signed and Sealed this
First Day of September, 2015

Michelle K. Lee
*Director of the United States Patent and Trademark Office*